(12) United States Patent
Takihana et al.

(10) Patent No.: US 8,993,212 B2
(45) Date of Patent: Mar. 31, 2015

(54) FLUORINE-CONTAINING SULFONIC ACID SALTS, PHOTO-ACID GENERATOR AND RESIST COMPOSITION AND PATTERN FORMATION METHOD UTILIZING SAME

(75) Inventors: Ryozo Takihana, Kawagoe (JP); Satoru Narizuka, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 13/879,989

(22) PCT Filed: Oct. 14, 2011

(86) PCT No.: PCT/JP2011/073615
§ 371 (c)(1),
(2), (4) Date: Apr. 17, 2013

(87) PCT Pub. No.: WO2012/056901
PCT Pub. Date: May 3, 2012

(65) Prior Publication Data
US 2013/0209938 A1    Aug. 15, 2013

(30) Foreign Application Priority Data

Oct. 27, 2010 (JP) ................................. 2010-240951

(51) Int. Cl.

| | | |
|---|---|---|
| G03F 7/004 | (2006.01) | |
| G03F 7/38 | (2006.01) | |
| C07C 303/32 | (2006.01) | |
| C07C 309/06 | (2006.01) | |
| C07C 309/16 | (2006.01) | |
| C07C 309/19 | (2006.01) | |
| G03F 7/027 | (2006.01) | |
| C07C 309/12 | (2006.01) | |
| C07C 309/10 | (2006.01) | |
| C07C 381/12 | (2006.01) | |

(Continued)

(52) U.S. Cl.
CPC .............. *G03F 7/027* (2013.01); *C07C 303/32* (2013.01); *C07C 309/06* (2013.01); *C07C 309/12* (2013.01); *C07C 309/16* (2013.01); *C07C 309/19* (2013.01); *C07C 309/10* (2013.01); *C07C 381/12* (2013.01); *C07C 2101/14* (2013.01); *C07C 2103/74* (2013.01); *G03F 7/0045* (2013.01); *G03F 7/0046* (2013.01); *G03F 7/0382* (2013.01); *G03F 7/0392* (2013.01); *G03F 7/2041* (2013.01); *Y10S 430/111* (2013.01); *Y10S 430/122* (2013.1); *Y10S 430/123* (2013.01)
USPC ........ 430/270.1; 430/326; 430/910; 430/921; 430/922; 562/100; 562/109; 562/113

(58) Field of Classification Search
CPC ....... G03F 7/0045; G03F 7/0397; G03F 7/38; C07C 303/32; C07C 309/06; C07C 309/12; C07C 309/19; C07C 2101/14; C07C 2103/74

USPC ...................... 430/270.1, 910, 921, 922, 326; 562/109, 113
See application file for complete search history.

(56) References Cited

U.S. PATENT DOCUMENTS

| | | |
|---|---|---|
| 7,569,324 B2 | 8/2009 | Kobayashi et al. |
| 7,812,105 B2 | 10/2010 | Nagai et al. |

(Continued)

FOREIGN PATENT DOCUMENTS

| | | |
|---|---|---|
| CA | 2 049 772 A1 | 2/1992 |
| JP | 4-230645 A | 8/1992 |

(Continued)

OTHER PUBLICATIONS

Corresponding International Search Report with English Translation dated Nov. 8, 2011 (five (5) pages).

(Continued)

*Primary Examiner* — John Chu
(74) *Attorney, Agent, or Firm* — Crowell & Moring LLP

(57) ABSTRACT

A resist composition according to the present invention includes at least a base resin, a photoacid generator and a solvent, wherein the photoacid generator comprises a fluorine-containing sulfonic acid salt of the following general formula (4).

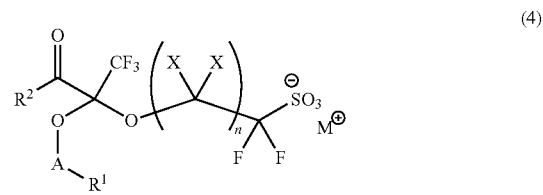

(4)

In the formula, X independently represents a hydrogen atom or a fluorine atom; n represents an integer of 1 to 6; $R^1$ represents a hydrogen atom, or an alkyl, alkenyl, oxoalkyl, aryl or aralkyl group; any of hydrogen atoms on carbons in $R^1$ may be substituted with a substituent; $R^2$ represents $R^4O$ or $R^B R^C N$; and A represents a divalent group. This fluorine-containing sulfonic acid salt can serve as a photoacid generator having high solubility in a resist solvent and thus can suitably be used for a resist composition such that the resist composition shows high resolution, wide DOF, small LER and high sensitivity to form a good pattern shape in lithographic processes.

14 Claims, No Drawings

(51) Int. Cl.
  *G03F 7/038* (2006.01)
  *G03F 7/039* (2006.01)
  *G03F 7/20* (2006.01)

(56) References Cited

U.S. PATENT DOCUMENTS

| | | | |
|---|---|---|---|
| 7,897,821 B2 | 3/2011 | Nagai et al. | |
| 7,928,262 B2 | 4/2011 | Kobayashi et al. | |
| 7,956,142 B2 | 6/2011 | Nagai et al. | |
| 8,030,515 B2 | 10/2011 | Kobayashi et al. | |
| 8,110,711 B2 | 2/2012 | Jodry et al. | |
| 8,222,448 B2 | 7/2012 | Jodry et al. | |
| 8,435,717 B2 * | 5/2013 | Hagiwara et al. | 430/270.1 |
| 2006/0228648 A1 | 10/2006 | Ohsawa et al. | |
| 2007/0099113 A1 | 5/2007 | Kobayashi et al. | |
| 2008/0318160 A1 | 12/2008 | Ohsawa et al. | |
| 2009/0317745 A1 * | 12/2009 | Mimura et al. | 430/281.1 |
| 2010/0035185 A1 | 2/2010 | Hagiwara et al. | |
| 2010/0304303 A1 | 12/2010 | Maeda | |
| 2011/0003247 A1 * | 1/2011 | Ohashi et al. | 430/270.1 |
| 2011/0034721 A1 | 2/2011 | Hagiwara et al. | |
| 2011/0112306 A1 | 5/2011 | Nagamori et al. | |
| 2011/0177453 A1 * | 7/2011 | Masubuchi et al. | 430/270.1 |

FOREIGN PATENT DOCUMENTS

| | | |
|---|---|---|
| JP | 2002-214774 A | 7/2002 |
| JP | 2004-4561 A | 1/2004 |
| JP | 2004-117959 A | 4/2004 |
| JP | 2005-84365 A | 3/2005 |
| JP | 2007-145797 A | 6/2007 |
| JP | 2007-145804 A | 6/2007 |
| JP | 2008-7409 A | 1/2008 |
| JP | 2008-7410 A | 1/2008 |
| JP | 2009-7327 A | 1/2009 |
| JP | 2009-91351 A | 4/2009 |
| JP | 2010-18573 A | 1/2010 |
| JP | 2010-72273 A | 4/2010 |
| JP | 2010-132560 A | 6/2010 |
| WO | WO 2006/121096 A1 | 11/2006 |
| WO | WO 2008/056795 A1 | 5/2008 |

OTHER PUBLICATIONS

Japanese-language Written Opinion dated Nov. 8, 2011(PCT/ISA/237) (five (5) pages).

* cited by examiner

FLUORINE-CONTAINING SULFONIC ACID SALTS, PHOTO-ACID GENERATOR AND RESIST COMPOSITION AND PATTERN FORMATION METHOD UTILIZING SAME

TECHNICAL FIELD

The present invention relates to a novel fluorine-containing sulfonic acid salt, a photoacid generator, a resist composition and a pattern formation method using the same. More particularly, the present invention relates to a resist composition suitable as a chemically amplified resist material for fine processing by high-energy radiation, a novel photoacid generator for use in the resist composition and a novel fluorine-containing sulfonic acid salt for use in the photoacid generator.

BACKGROUND ART

For lithographic fine patterning in semiconductor manufacturing processes, there has been a demand for resist compositions that can be exposed at shorter wavelengths and show a wide depth of focus tolerance (abbreviated as "DOF"), a small line edge roughness (abbreviated as "LED"), high resolution, high sensitivity, good substrate adhesion and good etching resistance.

"Chemically amplified resist compositions" have been used for the reduction of the exposure wavelength. The chemically amplified resist composition is a pattern forming material that contains an acid generator (called "photoacid generator") capable of generating an acid by exposure and forms a pattern by changing the structure of the resist resin by the action of the acid generated from the acid generator as a catalyst and thereby causing a difference in developer solubility between exposed and unexposed portions of the resist film.

As photoacid generators of chemically amplified resist composition for exposure at 248 nm wavelength (KrF laser radiation), there are generally used those capable of generating perfluoroalkanesulfonic acids of long chain and high acidity. However, the perfluorooctanesulfonic acid and derivatives thereof (PFOS) have the problems concerning the stability (non-degradability) due to C—F bonds and the biological concentration and accumulation due to hydrophobic and lipophilic natures. The same problems are also being raised against the perfluoroalkanesulfonic acids of 5 or more carbon atoms and their derivatives. For such a reason, the U.S. Environmental Protection Agency has proposed a rule to regulate the use of these compounds.

Under the above circumstances, alkoxycarbonylfluoroalkanesulfonic acid onium salts such triphenylsulfonium methoxycarbonyldifluoromethanesulfonate (Patent Document 1), (4-methylphenyl)diphenylsulfonyl t-butoxycarbonyldifluoromethanesulfonate (Patent Document 2) and triphenylsulfonium (adamantane-1-ylmethyl)oxycarbonyldifluoromethanesulfonate (Patent Document 3) have been developed as acid generators, each of which is capable of generating a partially- or fully-fluorinated, lower-carbon-number alkanesulfonic acid of sufficient acidity and less environmental load.

However, the alkoxycarbonylfluoroalkanesulfonic acid onium salts developed as the photoacid generators have significantly low solubility in ordinary resist solvents (such as propylene glycol monomethylether acetate). There thus remains a problem that it is difficult to introduce a large amount of such onium salt acid generators in the resist compositions so that the resist compositions cannot exhibit adequate performance (DOF, LER, resolution etc.).

PRIOR ART DOCUMENTS

Patent Documents

Patent Document 1: Japanese Laid-Open Patent Publication No. 2004-117959
Patent Document 2: Japanese Laid-Open Patent Publication No. 2002-214774
Patent Document 3: Japanese Laid-Open Patent Publication No. 2004-4561

DISCLOSURE OF THE INVENTION

Problems to be Solved by the Invention

As mentioned above, there have been proposed photoacid generators each capable of generating a partially- or fully-fluorinated, lower-carbon-number alkanesulfonic acid in order for the resulting resist compositions to show high resolution, wide DOF, small LER, high sensitivity and form a good pattern shape in lithographic processes for semiconductor manufacturing. These photoacid generators however have low solubility in ordinary resist solvents (such as propylene glycol monomethylether acetate) and cannot be introduced to the resist compositions in such amounts as to generate sufficient acids.

Means for Solvent the Problems

As a result of extensive researches made to solve the above problems, the present inventors have found that: a fluorine-containing sulfonic acid salt of specific structure have very high solubility in propylene glycol monomethylether acetate; and that a positive or negative resist composition prepared using such a fluorine-containing sulfonic acid salt as a photoacid generator can form a pattern with high resolution, wide DOF and small LER. The present invention is based on these findings.

Namely, the present invention includes the following aspects.

[Inventive Aspect 1]

A resist composition comprising at least a base resin, a photoacid generator and a solvent, wherein the photoacid generator comprises a fluorine-containing sulfonic acid salt of the following general formula (4):

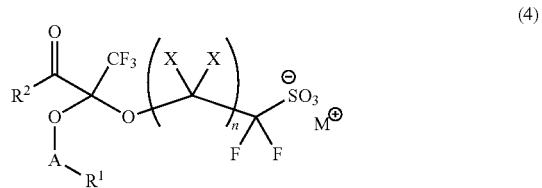

(4)

where X each independently represents a hydrogen atom or a fluorine atom; n represents an integer of 1 to 10; $R^1$ represents a hydrogen atom, a $C_1$-$C_{20}$ alkyl group, a $C_2$-$C_{20}$ alkenyl group or oxoalkyl group, or a $C_6$-$C_{18}$ aryl group or aralkyl group; any of hydrogen atoms on carbons in $R^1$ may be substituted with a substituent; $R^2$ represents either $R^4O$ or $R^BR^CN$; $R^A$, $R^B$ and $R^C$ each independently represents a hydrogen atom, a $C_1$-$C_{20}$ alkyl group, a $C_2$-$C_{20}$ alkenyl group or oxoalkyl group, a $C_6$-$C_{18}$ aryl group or aralkyl group, or a $C_3$-$C_{30}$ lactone group; $R^B$ and $R^C$ may form a 3- to 18-membered heterocyclic ring; any of hydrogen atoms on carbons in $R^A$, $R^B$ and $R^C$ may be substituted with a substituent; A represents any one of groups of the following formulas:

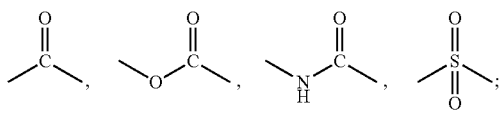

and $M^+$ represents a monovalent cation.

[Inventive Aspect 2]

The resist composition according to Inventive Aspect 1, wherein the photoacid generator comprises a fluorine-containing sulfonic acid onium salt of the following general formula (2):

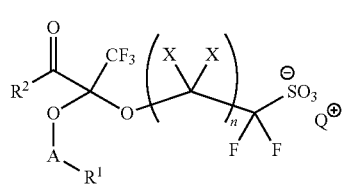

(2)

where X, n, A, $R^1$ and $R^2$ have the same meanings as in the general formula (4); and $Q^+$ represents a sulfonium cation of the following general formula (a) or an iodonium cation of the following general formula (b):

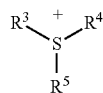

(a)

where $R^3$, $R^4$ and $R^5$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^3$, $R^4$ and $R^5$ may be bonded together to form a ring with a sulfur atom in the formula,

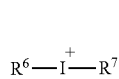

(b)

where $R^6$ and $R^7$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^6$ and $R^7$ may be bonded together to form a ring with an iodine atom in the formula.

[Inventive Aspect 3]

The resist composition according to Inventive Aspect 2, wherein, in the general formula (2), —$(CX_2)_n$— is a repeating unit represented by —$(CH_2)_p$—$(CF_2)_q$— where p is an integer of 0 to 10; and q is an integer of 0 to 8.

[Inventive Aspect 4]

The resist composition according to Inventive Aspect 2 or 3, wherein, in the general formula (2), —$(CX_2)_n$— is a repeating unit represented by —$(CH_2)_p$—$(CF_2)_q$— where p is an integer of 0 to 4; and q is 0 or 1.

[Inventive Aspect 5]

The resist composition according to any one of Inventive Aspects 2 to 4, wherein the base resin is a homopolymer of one kind of monomer, or a copolymer of two or more kinds of monomers, selected from the group consisting of acrylic esters, fluorine-containing acrylic esters, methacrylic esters, fluorine-containing methacrylic esters, styrenic compounds, fluorine-containing styrenic compounds, vinyl ethers, fluorine-containing vinyl ethers, allyl ethers, fluorine-containing allyl ethers, acrylamides, methacrylamides, vinyl esters, allyl esters, olefins, fluorine-containing olefins, norbornene compounds and fluorine-containing norbornene compounds.

[Inventive Aspect 6]

The resist composition according to any one of Inventive Aspects 2 to 5, wherein the base resin is insoluble or difficult to dissolve in a developer before exposure to high-energy radiation and is made soluble in a developer by the action of the photoacid generator as a result of exposure to high-energy radiation.

[Inventive Aspect 7]

The resist composition according to any one of Inventive Aspects 2 to 5, wherein the base resin is soluble in a developer before exposure to high-energy radiation and is made insoluble or difficult to dissolve in a developer by the action of the photoacid generator as a result of exposure to high-energy radiation.

[Inventive Aspect 8]

A pattern formation method comprising: applying the resist composition according to any one of Inventive Aspects 1 to 7 to a substrate; after heat treating the applied resist composition, exposing the applied resist composition to high-energy radiation of 300 nm or less wavelength through a photomask; and after heat treating the exposed resist composition as needed, developing the exposed resist composition with a developer.

[Inventive Aspect 9]

The pattern formation method according to Inventive Aspect 8, wherein the exposing is performed by liquid immersion lithography using ArF excimer laser radiation of 193 nm wavelength and allowing insertion of water or any other liquid of higher refractive index than that of the air between the substrate to which the resist composition has been applied and projector lens.

[Inventive Aspect 10]

A fluorine-containing sulfonic acid salt of the following general formula (4):

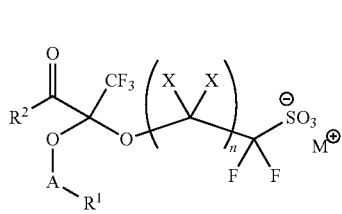

(4)

where X each independently represents a hydrogen atom or a fluorine atom; n represents an integer of 1 to 10; $R^1$ represents a hydrogen atom, a $C_1$-$C_{20}$ alkyl group, a $C_2$-$C_{20}$ alkenyl group or oxoalkyl group, or a $C_6$-$C_{18}$ aryl group or aralkyl group; any of hydrogen atoms on carbons in $R^1$ may be substituted with a substituent; $R^2$ represents either $R^4O$ or $R^BR^CN$; $R^A$, $R^B$ and $R^C$ each independently represents a hydrogen atom, a $C_1$-$C_{20}$ alkyl group, a $C_2$-$C_{20}$ alkenyl group or oxoalkyl group, a $C_6$-$C_{18}$ aryl group or aralkyl group, or a $C_3$-$C_{30}$ lactone group; $R^B$ and $R^C$ may form a 3- to 18-membered heterocyclic ring; any of hydrogen atoms on carbons in $R^A$, $R^B$ and $R^C$ may be substituted with a substituent; A represents any one of groups of the following formulas:

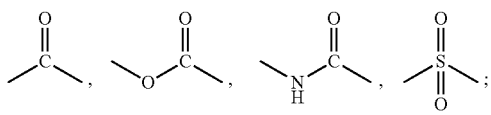

and $M^+$ represents a monovalent cation.

[Inventive Aspect 11]

The fluorine-containing sulfonic acid salt according to Inventive Aspect 10, wherein the fluorine-containing sulfonic acid salt is a fluorine-containing sulfonic acid onium salt of the following general formula (5):

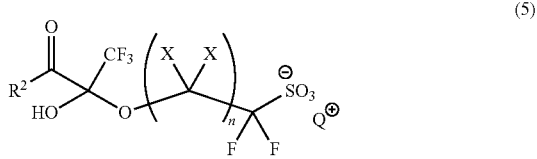

(5)

where X, n, A, $R^1$ and $R^2$ have the same meanings as in the general formula (4); and $Q^+$ represents a sulfonium cation of the following general formula (a) or an iodonium cation of the following general formula (b):

(a)

where $R^3$, $R^4$ and $R^5$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^3$, $R^4$ and $R^5$ may be bonded together to form a ring with a sulfur atom in the formula,

(b)

where $R^6$ and $R^7$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^6$ and $R^7$ may be bonded together to form a ring with an iodine atom in the formula.

[Inventive Aspect 12]

The fluorine-containing sulfonic acid salt according to Inventive Aspect 10 or 11, wherein, in the general formula (4) or (5), —$(CX_2)_n$— is a repeating unit represented by —$(CH_2)_p$—$(CF_2)_q$— where p is an integer of 0 to 10; and q is an integer of 0 to 8.

[Inventive Aspect 13]

The fluorine-containing sulfonic acid salt according to Inventive Aspect 10 or 11, wherein, in the general formula (4) or (5), —$(CX_2)_n$— is a repeating unit represented by —$(CH_2)_p$—$(CF_2)_q$— where p is an integer of 0 to 4; and q is 0 or 1.

[Inventive Aspect 14]

A photoacid generator comprising the fluorine-containing sulfonic acid salt according to Inventive Aspect 11.

It is possible to obtain the effects that: the fluorine-containing sulfonic acid salt used as the photoacid generator according to the present invention shows high solubility in propylene glycol monomethylether acetate; and the positive or negative resist composition using this photoacid generator has high resolution, wide DOF, small LED and high sensitivity and can form a good pattern shape.

DETAILED DESCRIPTION OF EMBODIMENTS

Hereinafter, exemplary embodiments of the present invention will be described below in detail. It is to be understood that: the following embodiments are illustrative and are not intended to limit the present invention thereto; and various changes and modifications can be made to the following embodiments, without departing from the scope of the present invention, based on the ordinary knowledge of one skilled in the art.

In the present specification, the following terms have the following meanings. The term "base resin" refers to a resin capable of changing its solubility in a developer by exposure. The term "positive resist" refers to a resist whose exposed area is more soluble in a developer, whereas the term "negative resist" refers to a resist whose exposed area is less soluble in a developer. The term "high-energy radiation" refers to an electromagnetic wave or particle beam by which a resist composition is acted on to generate an acid. In general, the high-energy radiation is an electromagnetic wave classified as near-ultraviolet radiation (wavelength: 380 to 200 nm), vacuum-ultraviolet radiation (far-ultraviolet radiation, VUV, wavelength: 200 to 10 nm), extreme-ultraviolet radiation (EUV, wavelength: 10 nm or shorter), soft X-ray, X-ray, γ-ray or the like, or a particle beam classified as electron beam or the like. The names of the above electromagnetic waves are only for the sake of convenience. For example, a radiation of 10 to 14 nm wavelength may sometimes be called EUV, soft X-ray etc.

Unless otherwise specified, the term "salt" includes the case where the cation of the salt is $H^+$.

A material relationship of the present invention is indicated in Scheme (1).

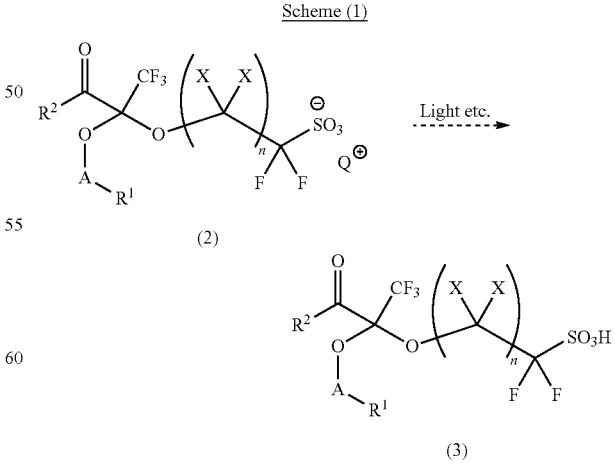

A fluorine-containing sulfonic acid onium salt of the general formula (2) is converted to a fluorine-containing sulfonic acid of the general formula (3) by the action of high-energy radiation, heat etc. This fluorine-containing sulfonic acid serves as an acid catalyst.

[Fluorine-Containing Sulfonic Acid or Sulfonic Acid Salt]

A fluorine-containing sulfonic acid or sulfonic acid salt according to the present invention, which has an anion structure of the general formula (1), will be first described below.

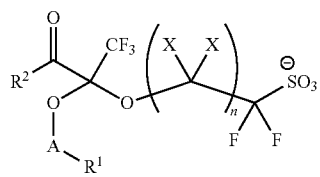
(1)

The fluorine-containing sulfonic acid or sulfonic acid salt having the structure of the general formula (1) is a fluorine-containing sulfonic acid or sulfonic acid salt of the general formula (4) where $M^+$ represents a monovalent cation.

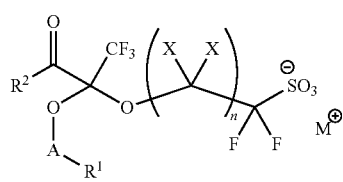
(4)

In the general formula (4), the monovalent cation is either a proton ($H^+$), a metal cation such as lithium ion, sodium ion or potassium ion, or an onium ion such as ammonium ion, sulfonium ion, iodonium ion or phosphonium ion.

In the general formula (1) and in the general formula (4), X each independently represents a hydrogen atom or a fluorine atom; and n represents an integer of 1 to 10, preferably 1 to 6.

The structure represented by $-(CX_2)_n-$ in the general formula (1) and in the general formula (4) is thus a $C_1$-$C_{10}$ straight alkylene group in which any number of hydrogen atoms may be substituted with a fluorine atom. Among others, preferred are those represented by $-(CH_2)_p-(CF_2)_q-$ where p is an integer of 0 to 10 and q is an integer of 0 to 8. Preferably, p is an integer of 1 to 6; and q is an integer of 0 to 5. It is more preferable that: p is an integer of 1 to 4; and q is 0 or 1.

Further, A represents any one of groups of the following formulas.

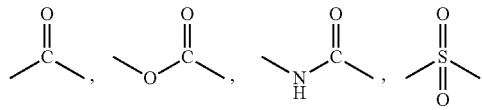

$R^1$ represents a hydrogen atom, a $C_1$-$C_{20}$ alkyl group, a $C_2$-$C_{20}$ alkenyl group or oxoalkyl group, or a $C_6$-$C_{18}$ aryl group or aralkyl group. Any of hydrogen atoms on carbons in $R^1$ may be substituted with a substituent.

More specifically, $R^1$ is exemplified as follows. Examples of the $C_1$-$C_{20}$ straight alkyl group are: methyl; ethyl; n-propyl; n-butyl; n-pentyl; n-hexyl; n-heptyl; n-octyl; n-nonyl; n-decyl; and straight alkyl groups substituted with cyclic alkyl groups, such as cyclopentylmethyl, cyclopentylethyl, cyclohexylmethyl, cyclohexylethyl, adamantylmethyl, adamantylethyl, norbornylmethyl, norbornylethyl, camphoroylmethyl and camphoroylethyl.

Examples of the $C_3$-$C_{20}$ branched alkyl group are: i-propyl; sec-butyl; i-butyl; and t-butyl.

Examples of the $C_3$-$C_{20}$ cyclic alkyl group are: cyclopentyl; cyclohexyl; adamantyl; methylcyclopentyl; methylcyclohexyl; methyladamantyl; ethylcyclopentyl; ethylcyclohexyl; ethyladamantyl; norbornyl; and camphoroyl.

Examples of the $C_2$-$C_{20}$ alkenyl group are: vinyl; 1-methylethenyl; allyl; 3-butenyl; 1-methylallyl; 2-methylallyl; 4-pentenyl; and 5-hexenyl.

Examples of the $C_2$-$C_{20}$ oxoalkyl group are: 2-oxo-propyl; 2-oxo-butyl; 2-oxo-3-methylbutyl; 2-oxo-pentyl; 2-oxo-3-methylpentyl; 2-oxo-4-methylpentyl; 2-oxo-3-ethylpentyl; 2-oxo-hexyl; 2-oxo-3-methylhexyl; 2-oxo-4-methylhexyl; 2-oxo-5-methylhexyl; 2-oxo-3-ethylhexyl; 2-oxo-4-ethylhexyl; 2-oxo-heptyl; 2-oxo-3-methylheptyl; 2-oxo-4-methylheptyl; 2-oxo-5-methylheptyl; 2-oxo-6-methylheptyl; 2-oxo-3-ethylheptyl; 2-oxo-4-ethylheptyl; 2-oxo-5-ethylheptyl; 2-oxo-3-propylheptyl; 2-oxo-4-propylheptyl; 2-oxo-octyl; 2-oxo-3-methyloctyl; 2-oxo-4-methyloctyl; 2-oxo-5-methyloctyl; 2-oxo-6-methyloctyl; 2-oxo-7-methyloctyl; 2-oxo-3-ethyloctyl; 2-oxo-4-ethyloctyl; 2-oxo-5-ethyloctyl; 2-oxo-cyclopentyl; 2-oxo-cyclohexyl; 2-oxo-cycloheptyl; 2-oxo-cyclopropylmethyl; 2-oxo-methylcyclohexyl; 2-oxo-cyclohexylmethyl; 2-oxo-norbornyl; 2-oxo-tricyclo[5.2.1.0$^{2,6}$]decyl; 2-cyclo-oxotetracyclo[4.4.0.1$^{2,5}$.1$^{7,10}$] dodecyl; and 2-oxo-bornyl.

Examples of the $C_6$-$C_{18}$ aryl group are: phenyl; o-tolyl; m-tolyl; p-tolyl; p-hydroxyphenyl; p-trifluoromethylphenyl; 1-naphthyl; and anthracenyl.

Examples of the $C_6$-$C_{18}$ aralkyl group are: benzyl; 1-phenylethyl; 2-phenylethyl; 1-phenylpropyl; 2-phenylpropyl; 3-phenylpropyl; 1-naphthylmethyl; and 2-naphthylmethyl.

Any of hydrogen atoms on carbons in $R^1$ may be substituted with a substituent. Examples of such a substituent are: a halogen atom such as fluorine, chlorine, bromine or iodine; a hydroxyl group; a thiol group; an aryl group; and an organic group having a hetero atom such as halogen, oxygen, nitrogen, sulfur, phosphorus or silicon. Two hydrogen atoms on the same carbon in $R^1$ may be replaced by one oxygen atom to thereby form a ketone group. These substituents can exist in any number as long as structurally possible.

$R^1$ is preferably a bulky functional group such as cyclopentyl, cyclohexyl, adamantyl, methylcyclopentyl, methylcyclohexyl, methyladamantyl, ethylcyclopentyl, ethylcyclohexyl, ethyladamantyl, norbornyl, camphoroyl, cyclopentylmethyl, cyclopentylethyl, cyclohexylmethyl, cyclohexylethyl, adamantylmethyl, adamantylethyl, norbornylmethyl, norbornylethyl, camphoroylmethyl or camphoroylethyl. Among others, cyclohexyl and adamantyl are particularly preferred.

$R^2$ represents either $R^AO$ or $R^BR^CN$. $R^A$, $R^B$ and $R^C$ each independently represents a hydrogen atom, a $C_1$-$C_{20}$ alkyl group, a $C_2$-$C_{20}$ alkenyl group or oxoalkyl group, a $C_6$-$C_{18}$ aryl group or aralkyl group, or a $C_3$-$C_{30}$ lactone group. The $C_1$-$C_{20}$ alkyl group is either a $C_1$-$C_{20}$ straight alkyl group, a $C_3$-$C_{20}$ branched alkyl group or a $C_3$-$C_{20}$ cyclic alkyl group. The $C_3$-$C_{30}$ lactone group is a $C_3$-$C_{30}$ monocyclic or polycyclic lactone group. $R^B$ and $R^C$ may be bonded to each other to form a 3- to 18-membered heterocyclic ring with a nitrogen atom (N) in $R^BR^CN$. Any of hydrogen atoms on carbons in $R^A$, $R^B$ and $R^C$ may be substituted with a substituent.

$R^A$, $R^B$ and $R^C$ are exemplified as follows. Examples of the $C_1$-$C_{20}$ alkyl group, the $C_2$-$C_{20}$ alkenyl group or oxoalkyl group and the $C_6$-$C_{18}$ aryl group or aralkyl group as $R^A$, $R^B$ and $R^C$ are the same as the functional groups (substituent groups) exemplified as above as $R^1$.

Examples of the $C_3$-$C_{30}$ lactone group are monovalent groups obtained by elimination of one hydrogen atom from corresponding monocyclic or polycyclic lactones such as γ-butyrolactone, γ-valerolactone, Angelica lactone, γ-hexalactone, γ-heptalactone, γ-octalactone, γ-nonalactone, 3-methyl-4-octanolide (Whisky lactone), γ-decalactone, γ-undecalactone, γ-dodecalactone, γ-jasmolactone (7-decenolactone), δ-hexalactone, 4,6,6(4,4,6)-trimethyltetrahydropyrane-2-one, δ-octalactone, δ-nonalactone, δ-decalactone, δ-2-decenolactone, δ-undecalactone, δ-dodecalactone, δ-tridecalactone, δ-tetradecalactone, Lactoscatone, ε-decalactone, ε-dodecalactone, cyclohexyllactone, jasmine lactone, cis-jasmone lactone and methyl-δ-decalactone. There can also be used the following lactone groups. In the respective formulas, the dotted lines each indicate a bonding position.

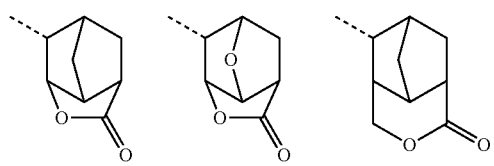
(E-1)

Examples of the 3- to 18-membered heterocyclic ring formed by $R^B$ and $R^C$ are those indicated below. In the respective formulas, the dotted lines each indicate a bonding position.

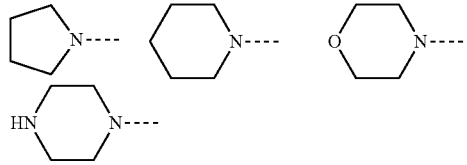
(E-2)

As mentioned above, any number of hydrogen atoms on carbons in $R^A$, $R^B$, $R^C$ may be substituted with a substituent. Examples of such a substituent are the same as those exemplified above as the substituent on $R^1$.

Preferred examples of $R^2$ are those indicated below. In the respective formulas, the dotted lines each indicate a bonding position.

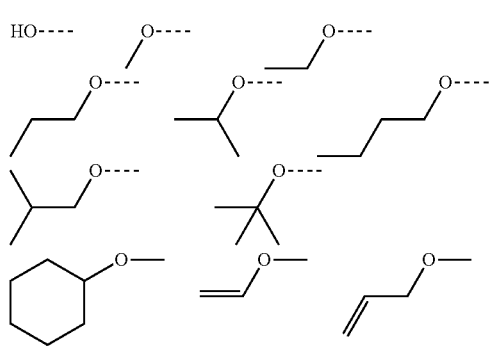
(E-3)

(E-4)

The anion structure of the general formula (1) is thus exemplified as follows. The fluorine-containing sulfonic acid salt of the general formula (4) corresponds to those in which a cation $M^+$ is bonded to any of the following anion structures. The fluorine-containing sulfonic acid onium salt of the general formula (2) corresponds to those in which a cation $Q^+$ is bonded to any of the following anion structures. The following anion structures are examples where the linking group A is a carbonyl group (—C(=O)—) in the general formula (1), the general formula (4) and the general formula (2). There are also preferred those where the linking group A is a carbonyloxy group (—C(=O)O—), an amide group (—NHC(=O)—) or a sulfonyl group (—S(=O)$_2$—) as mentioned above. Among others, carbonyl group is particularly preferred as the linking group A.
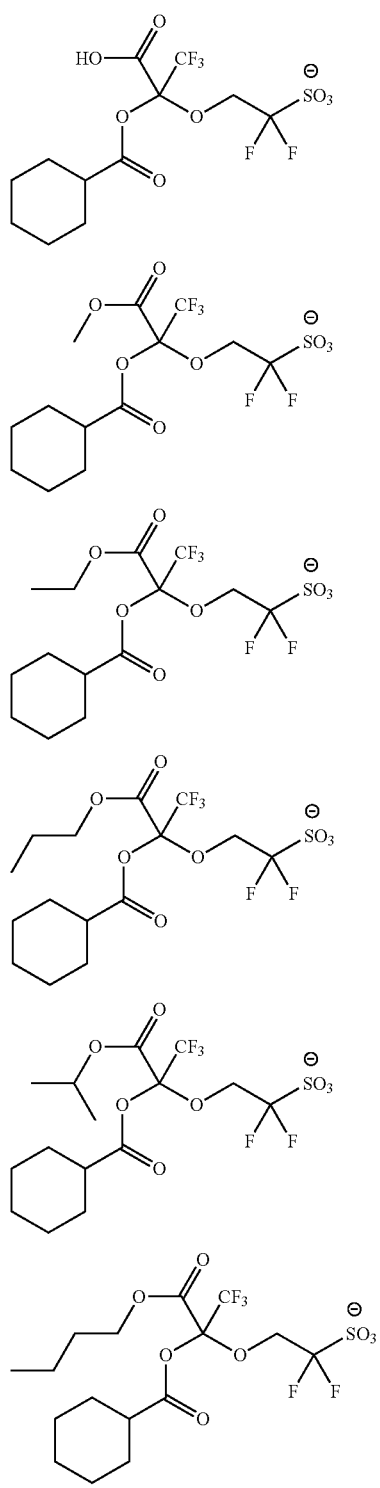
(E-5-1)
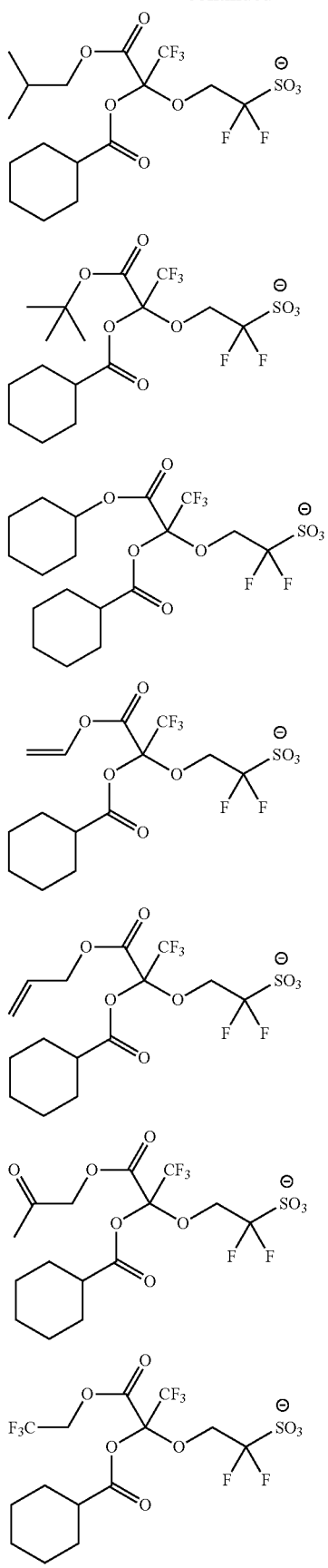

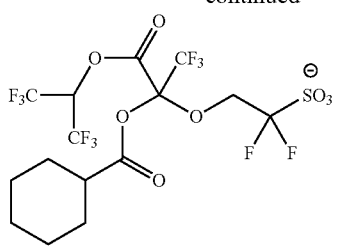
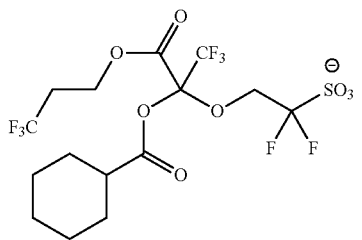
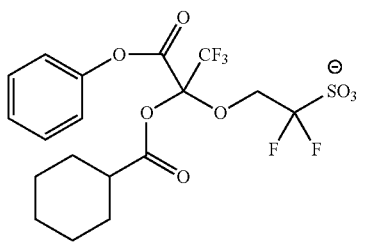
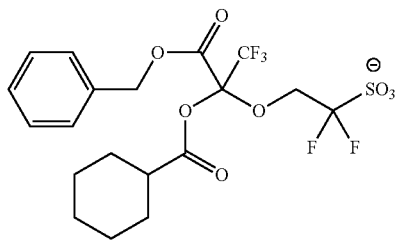
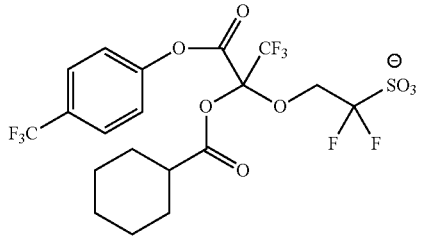
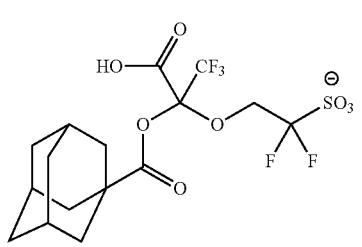
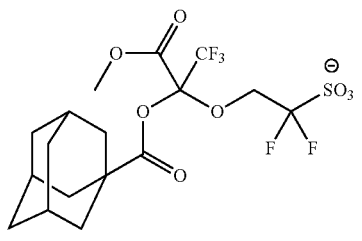
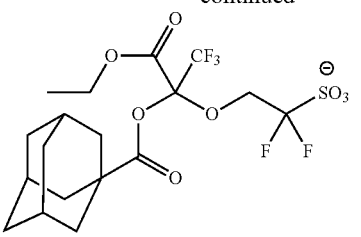
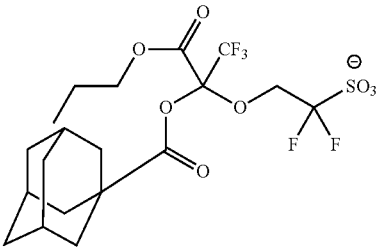
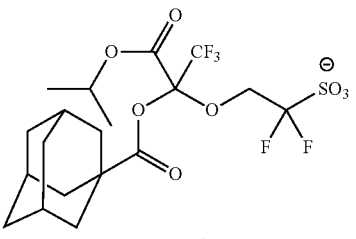
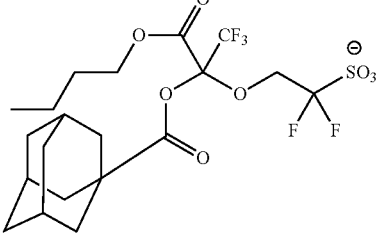
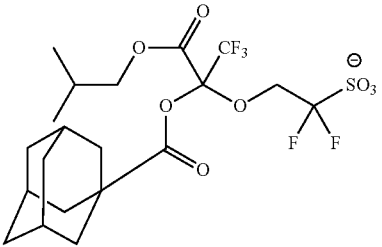
(E-5-2)
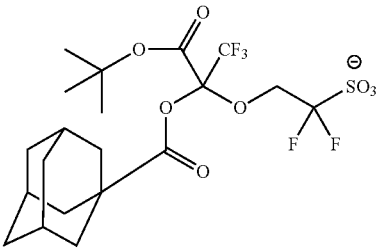
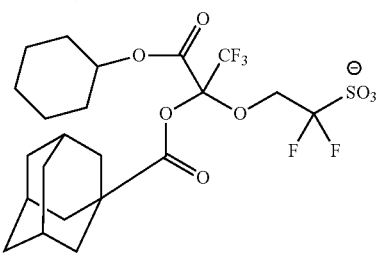

-continued
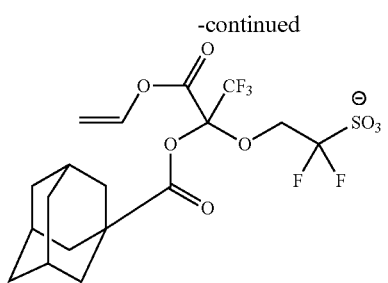
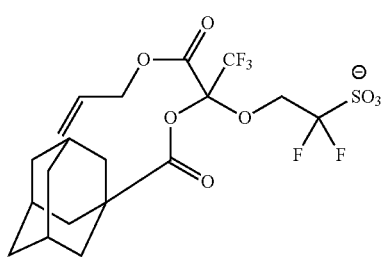
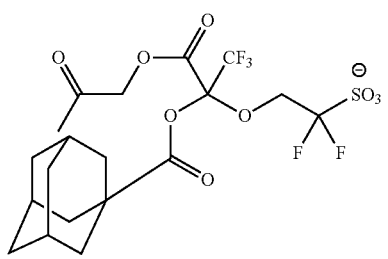
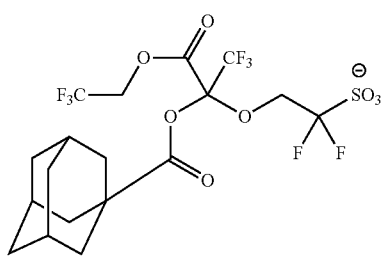
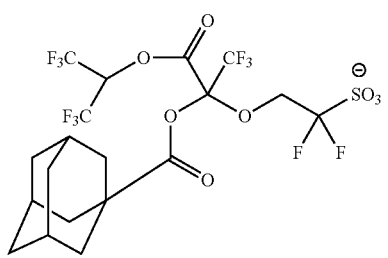
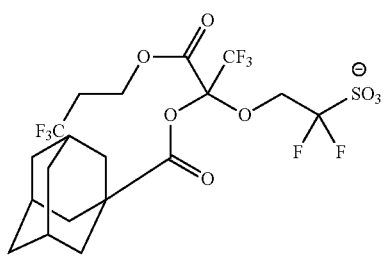
-continued
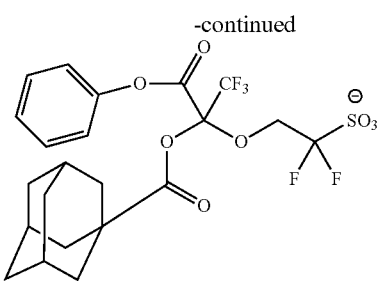
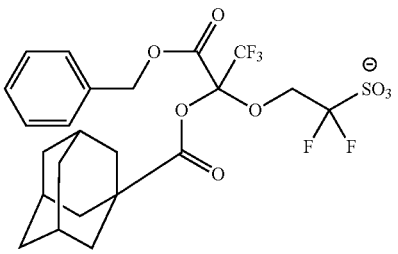
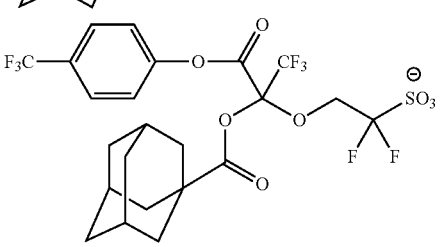
(E-5-3)
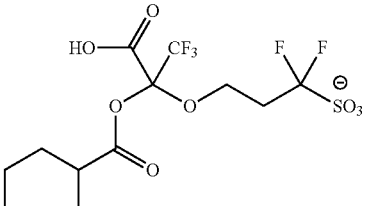
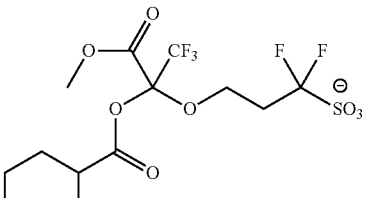
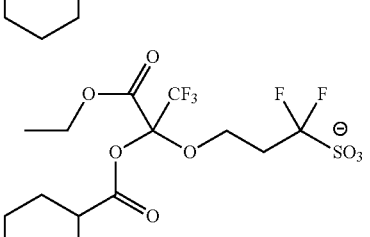
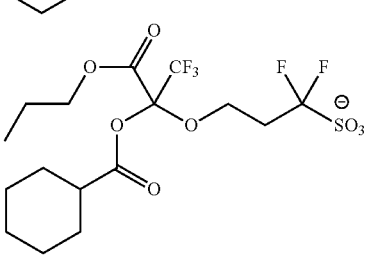

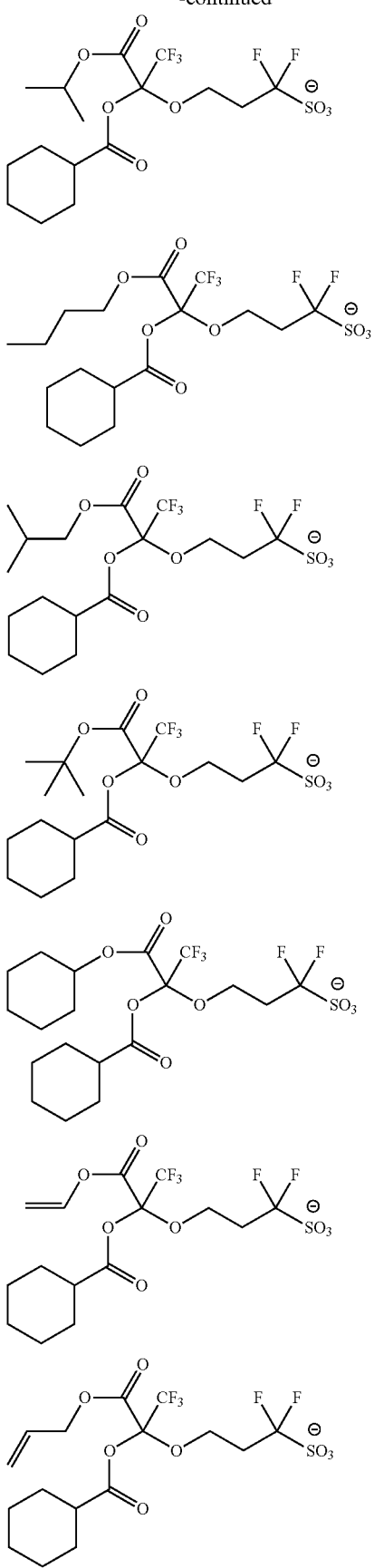
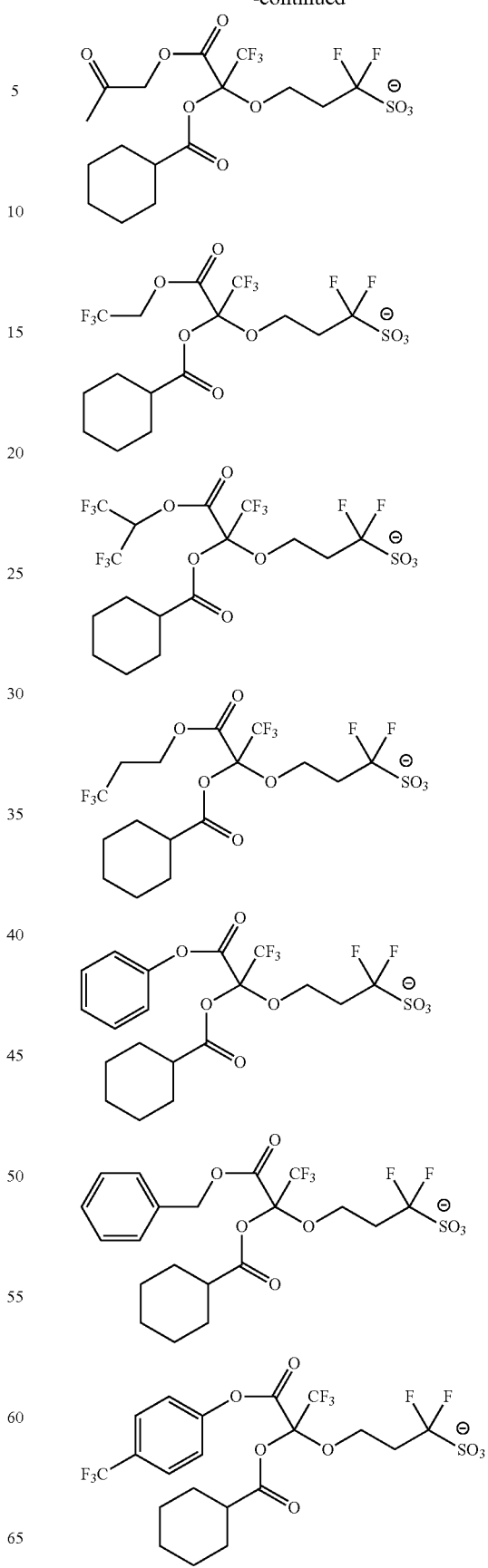

(E-5-4)
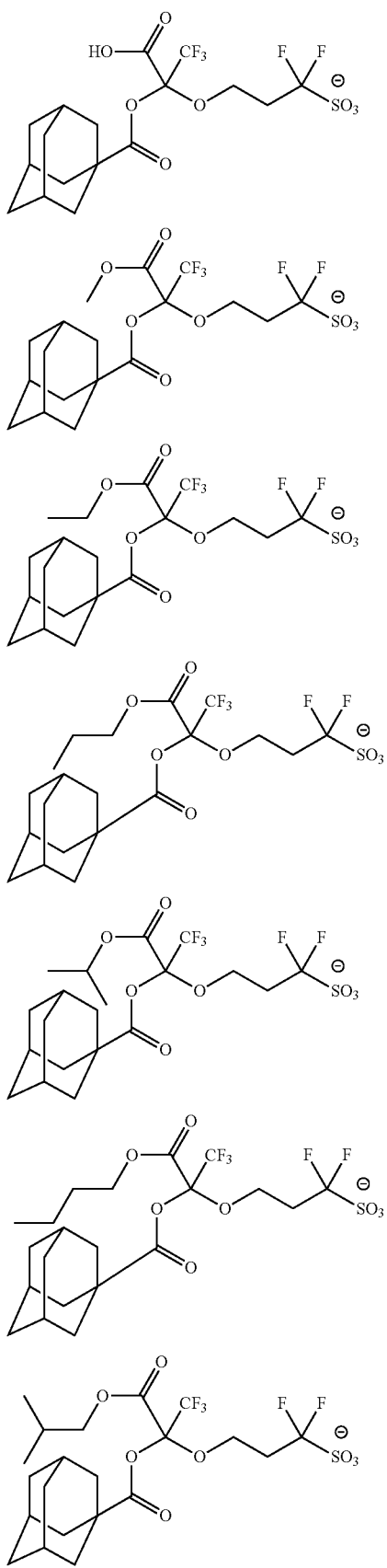
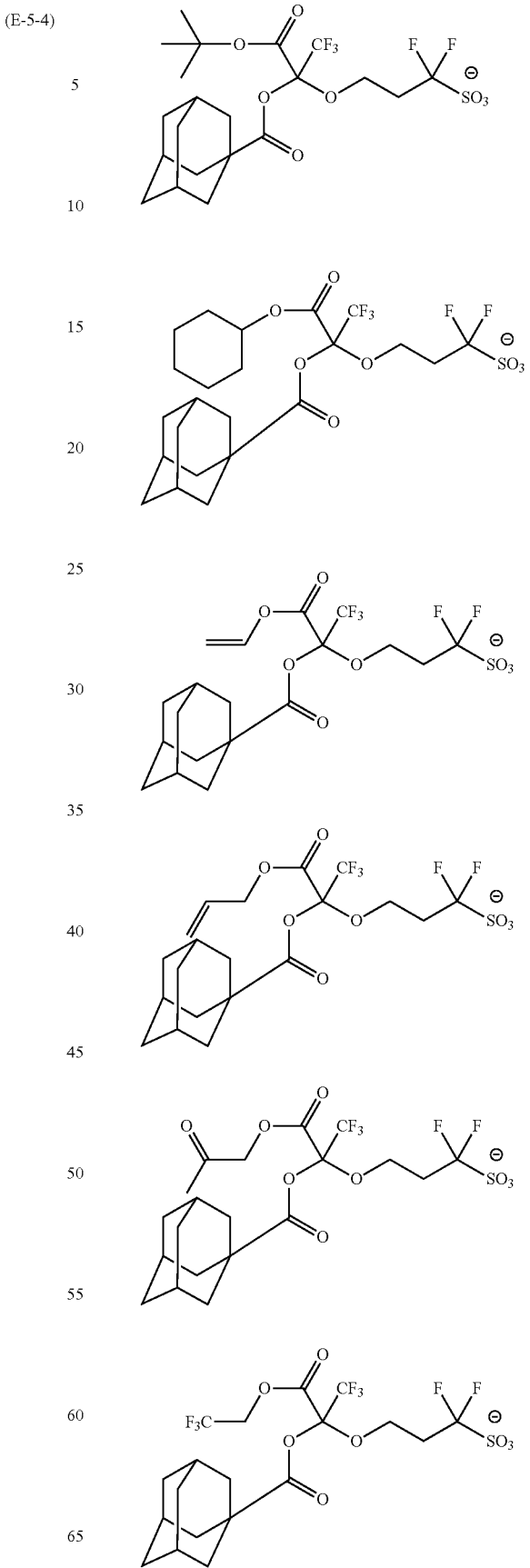

-continued
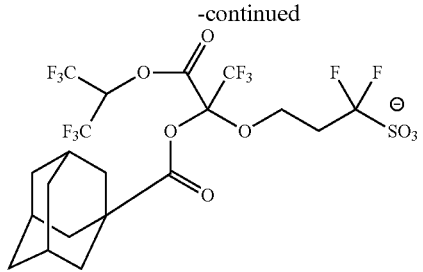
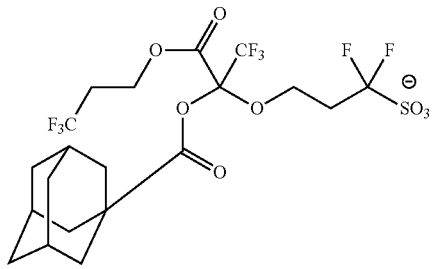
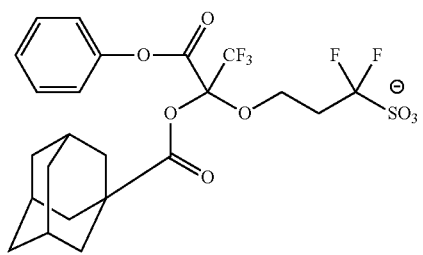
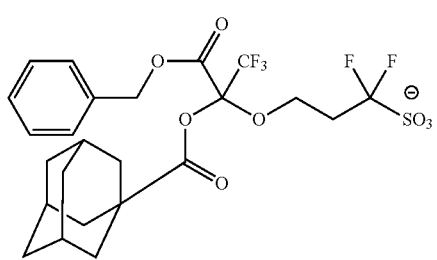
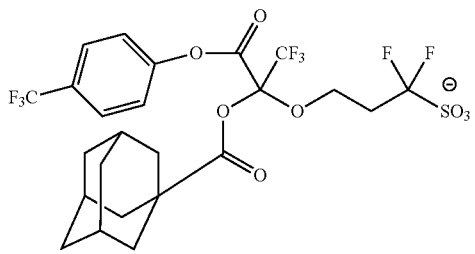
(E-5-5)
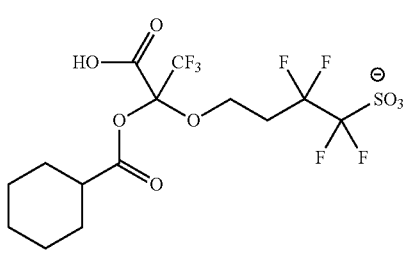
-continued
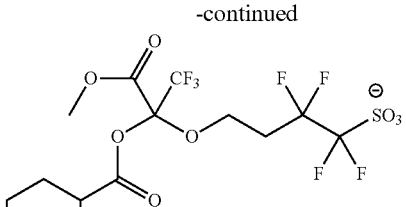
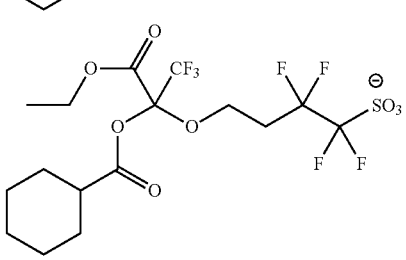
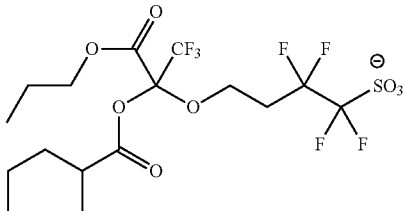
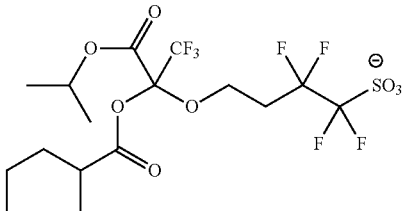
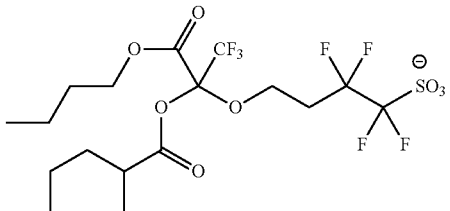
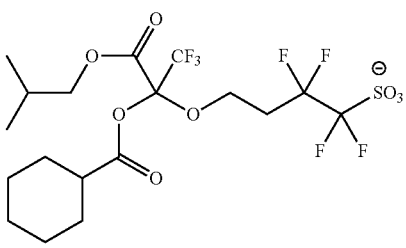
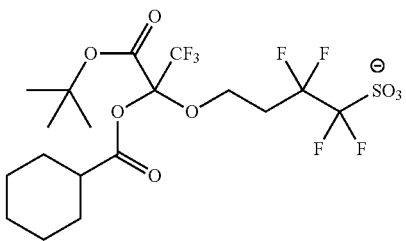

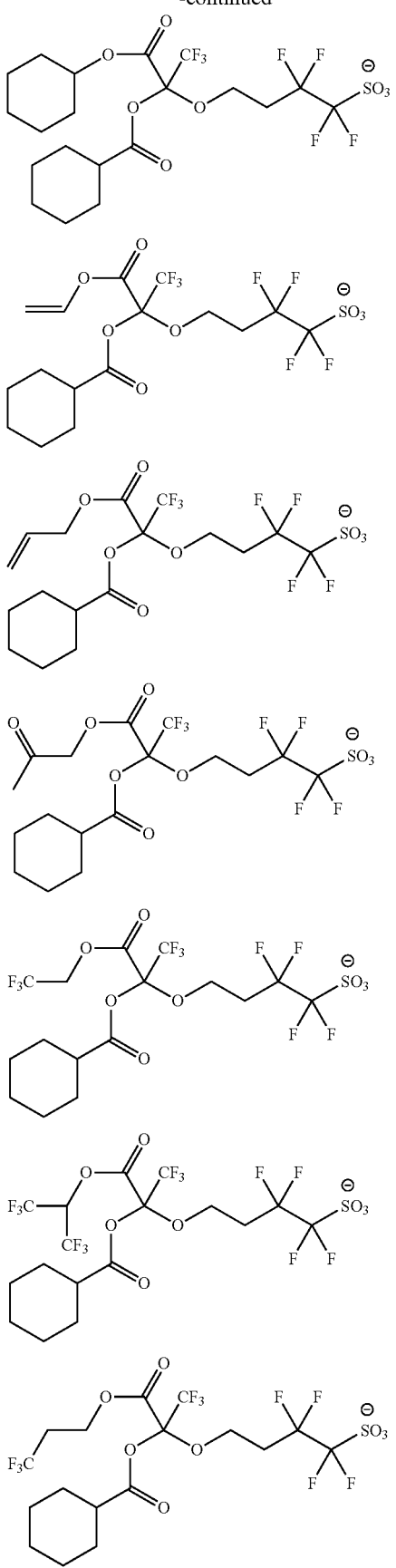
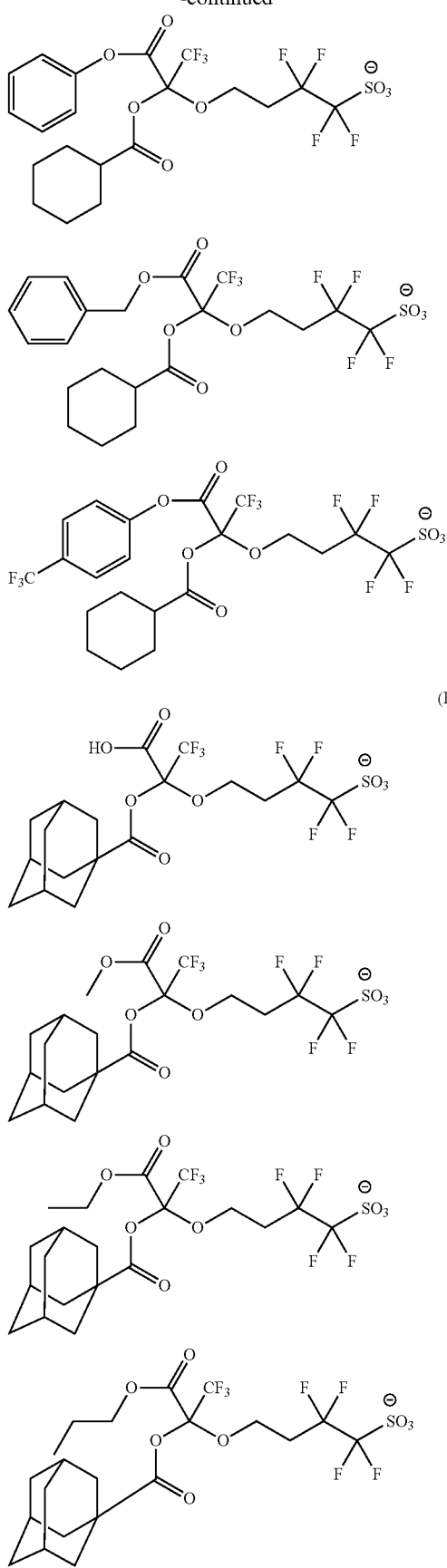

-continued
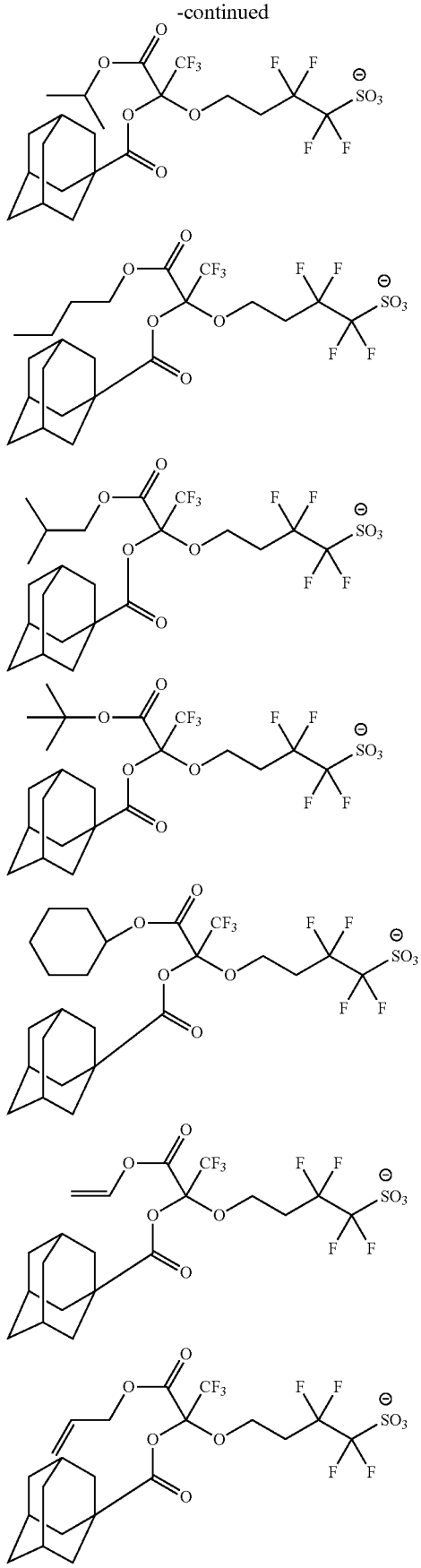
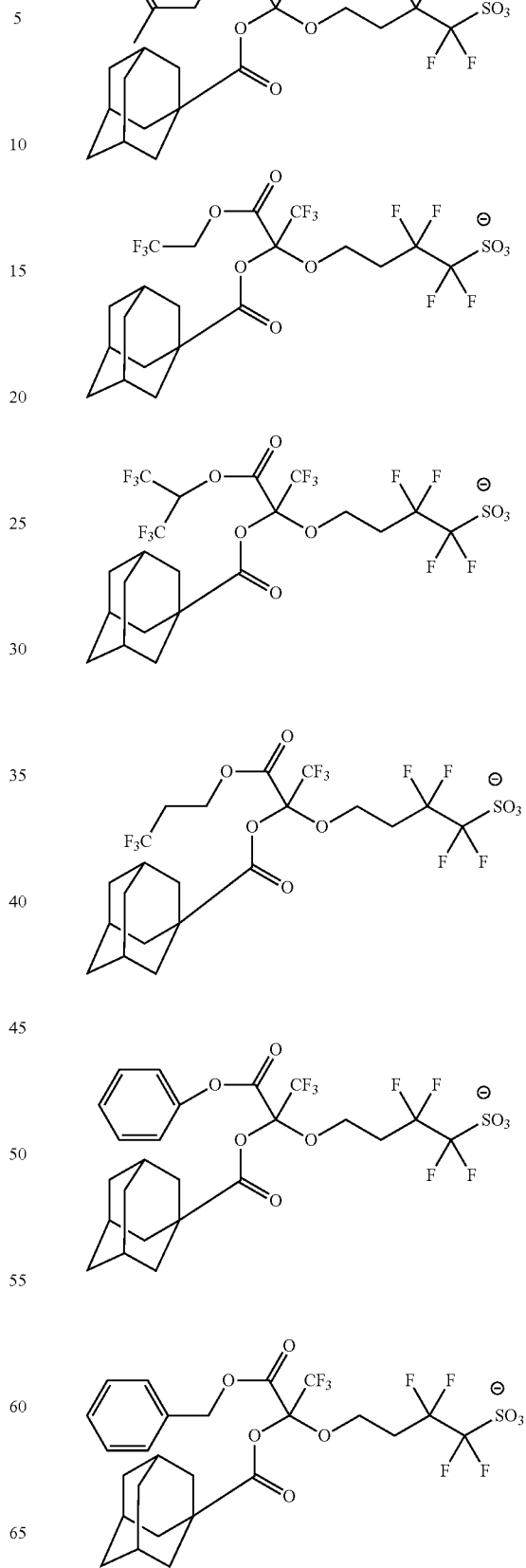

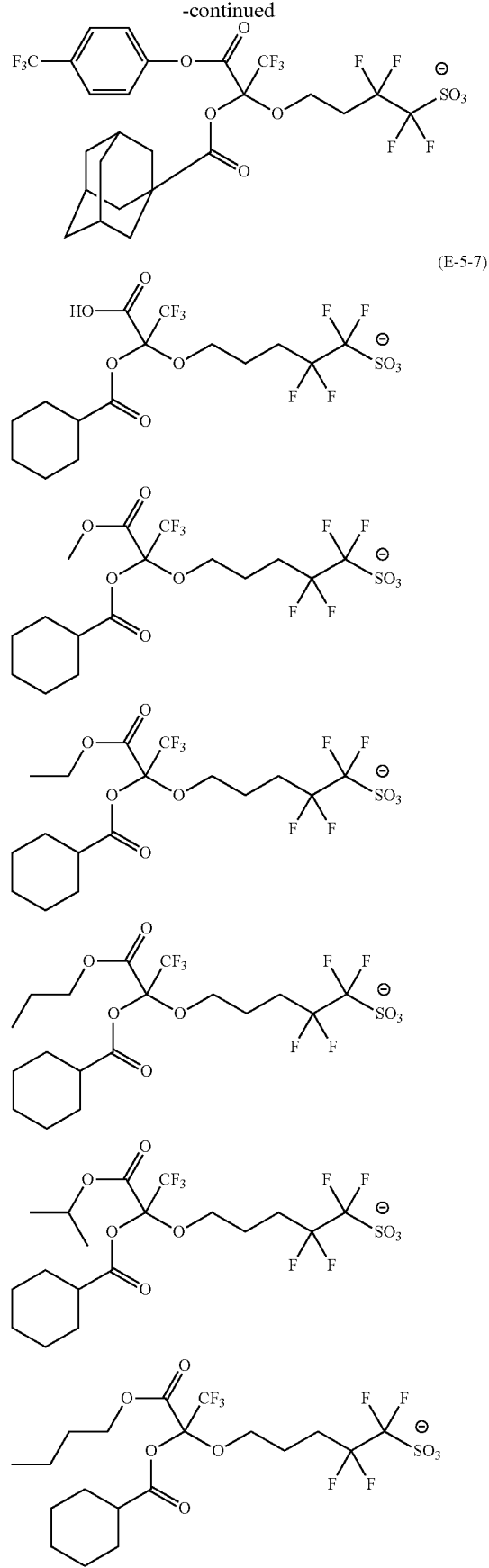
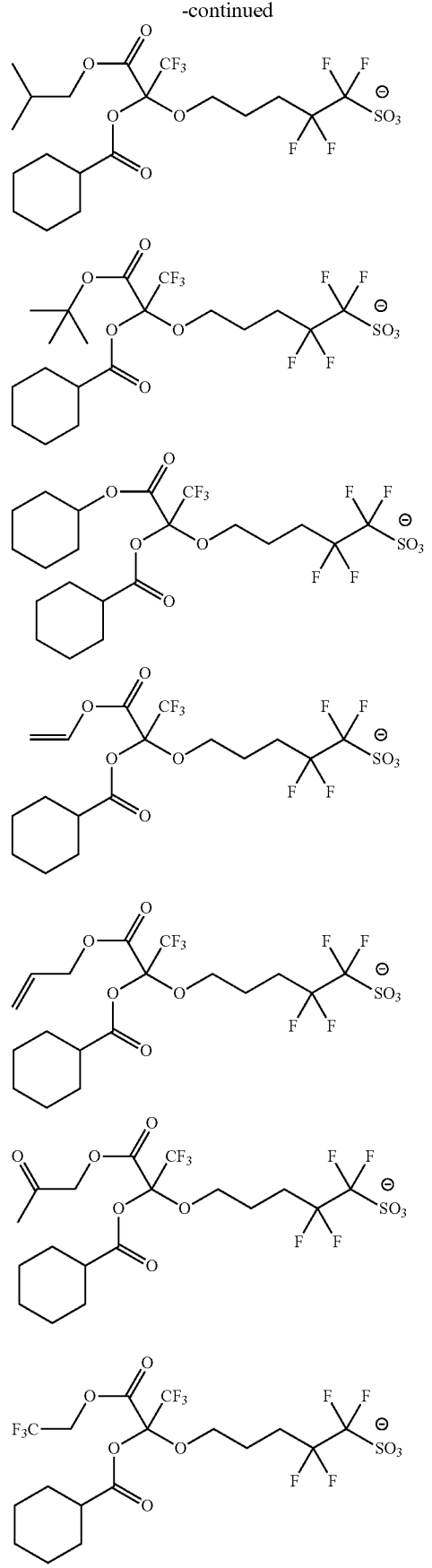

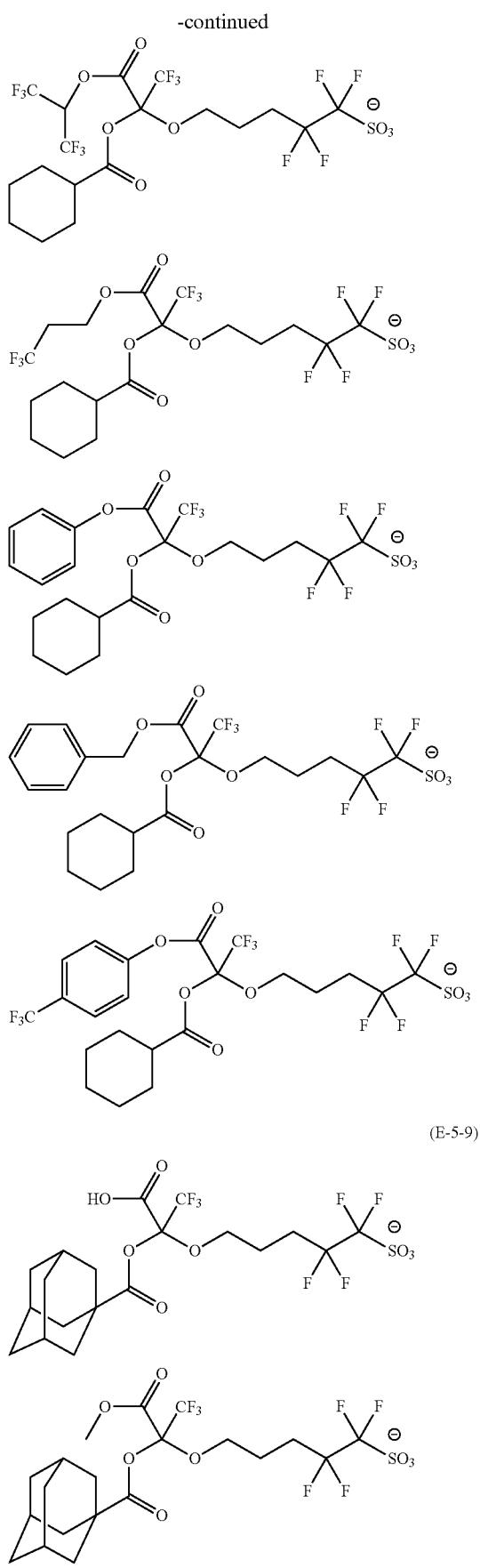
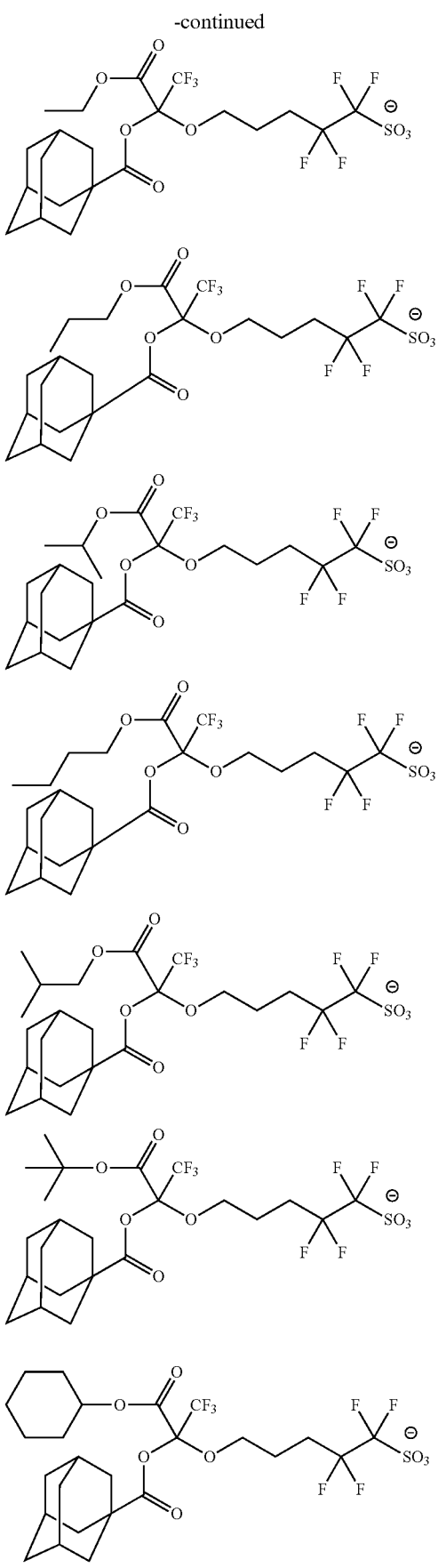
(E-5-9)

-continued
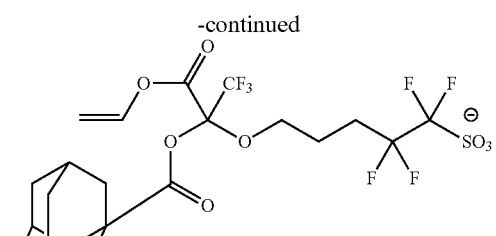
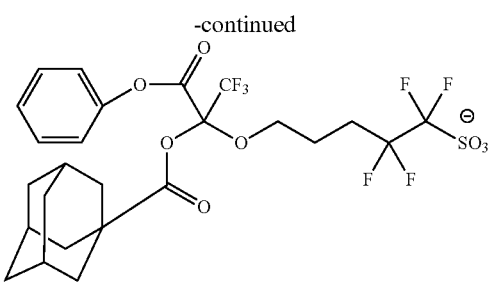
(E-5-10)
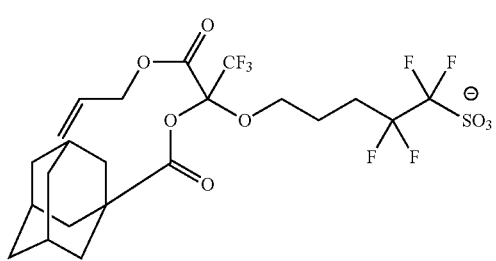
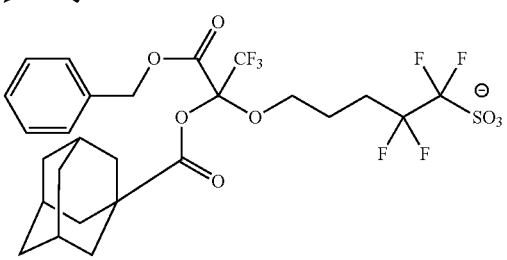
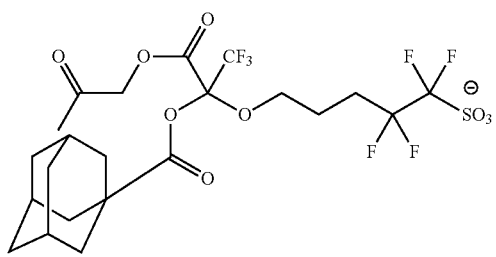
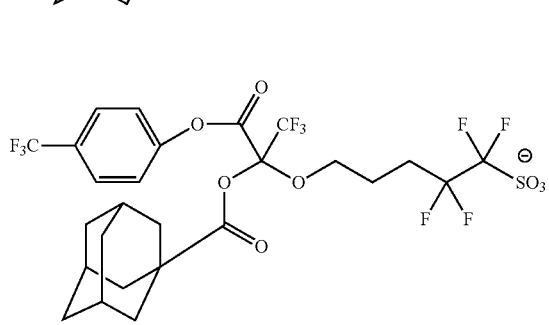
(E-5-11)
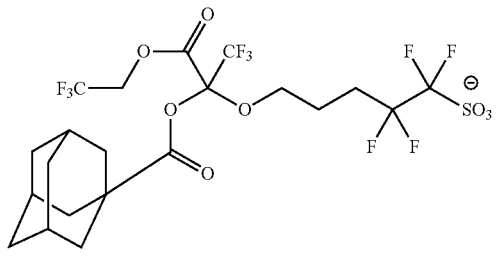
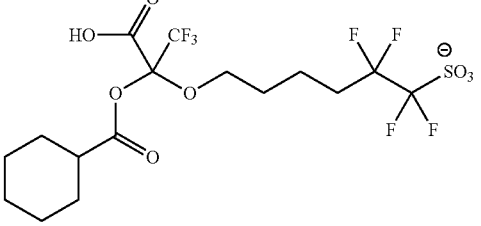
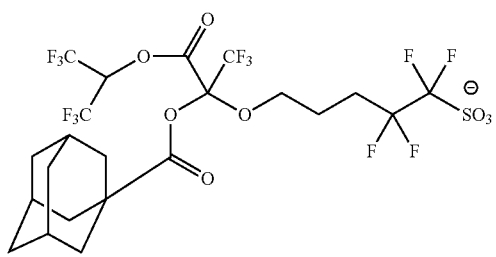
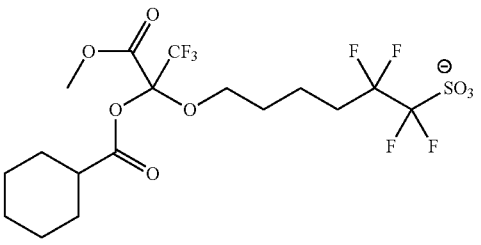
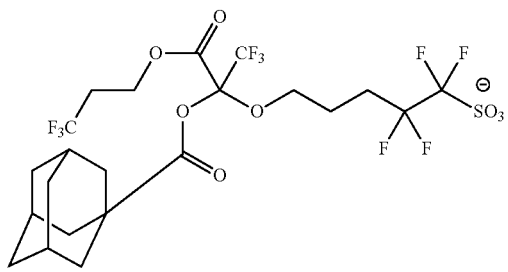
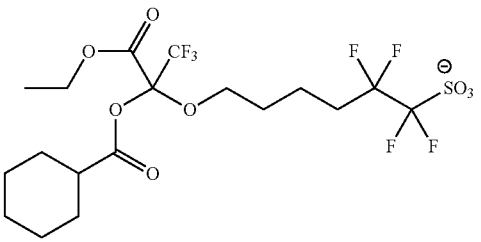

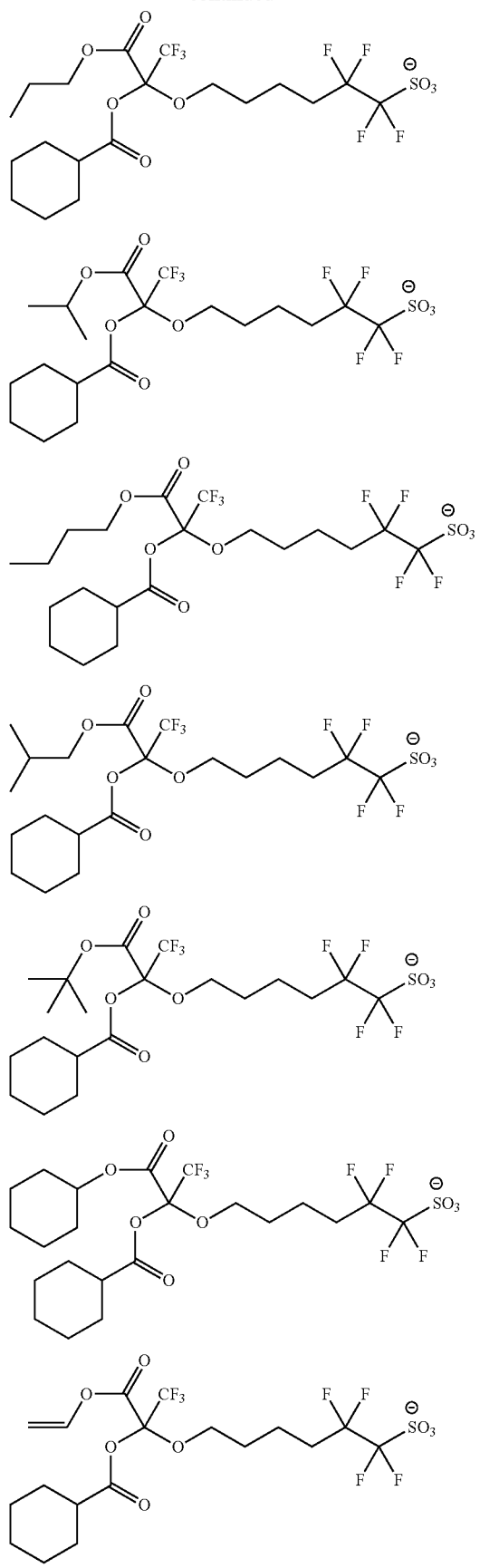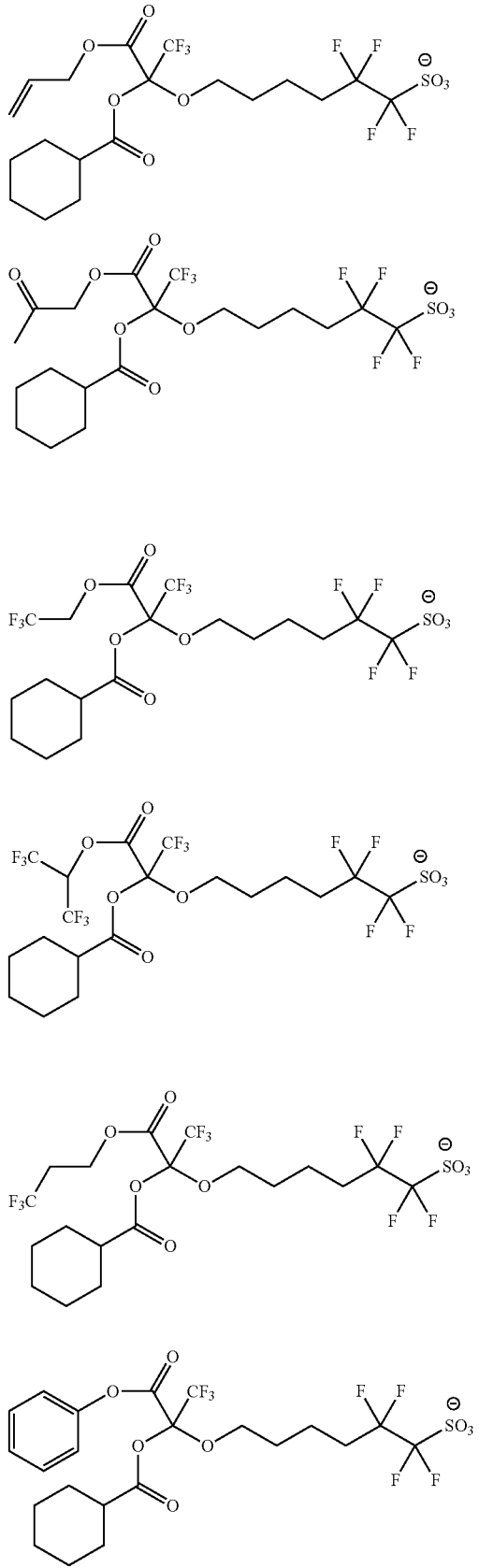
(E-5-12)

-continued
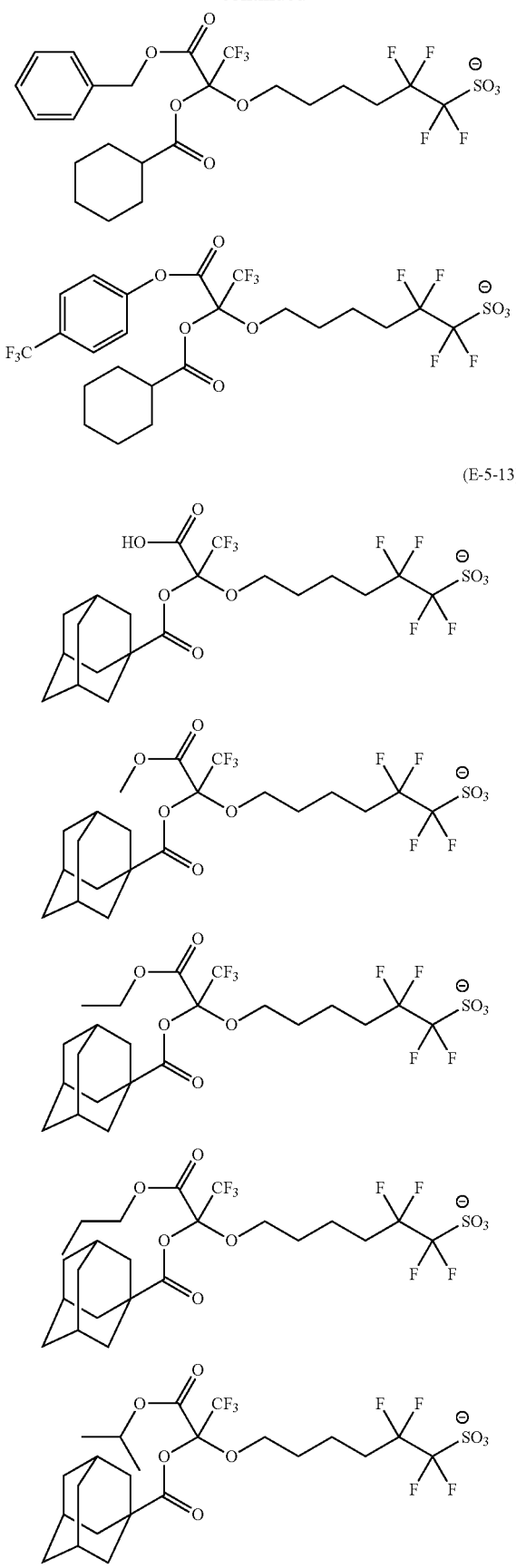
(E-5-13)
-continued
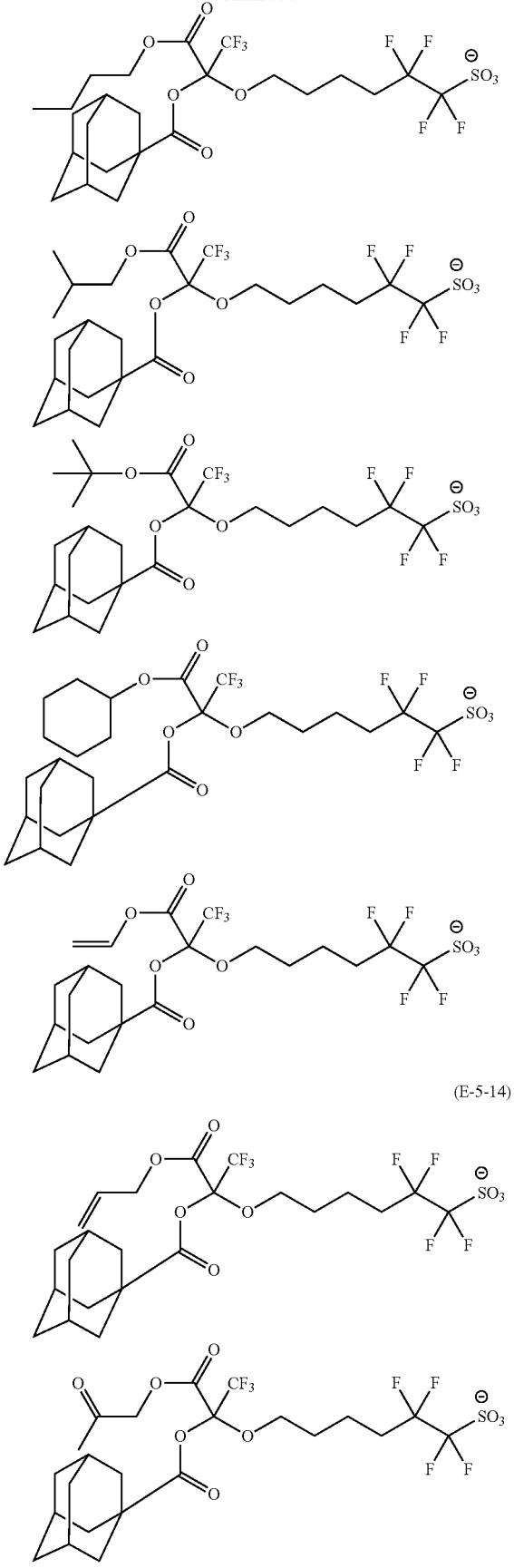
(E-5-14)

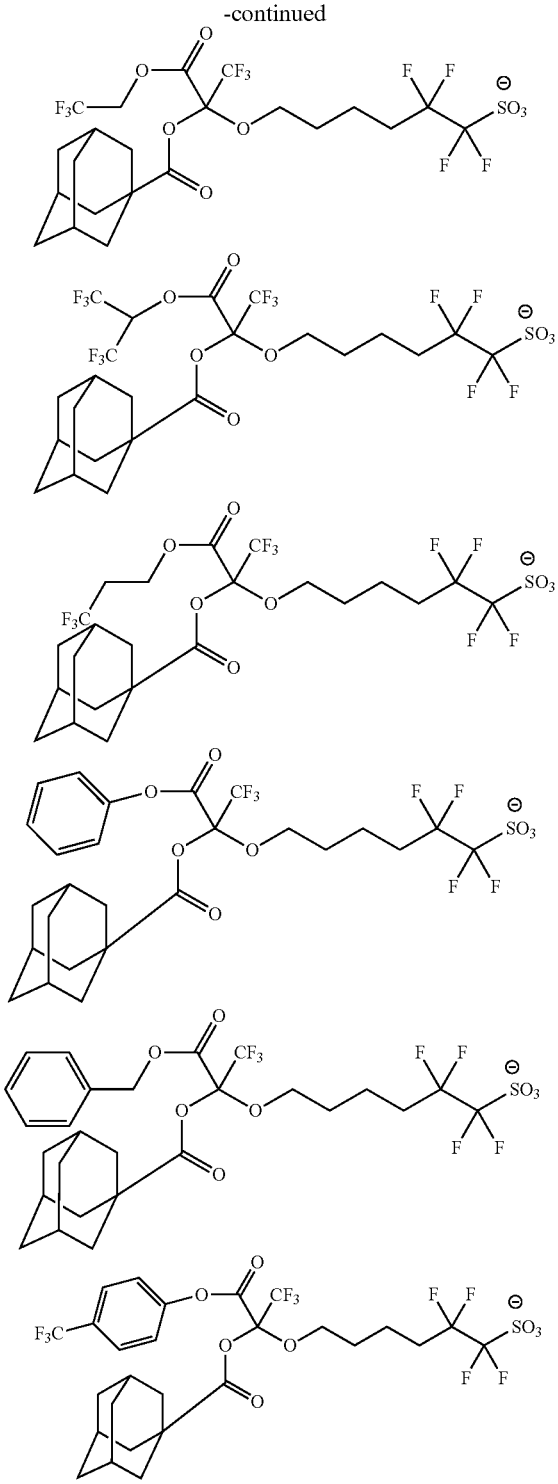

[Fluorine-containing Sulfonic Acid Onium Salt]

The fluorine-containing sulfonic acid onium salt of the general formula (2) is one preferred example of the polymerizable fluorine-containing sulfonic acid salt having the structure of the general formula (1) according to the present invention. This fluorine-containing sulfonic acid onium salt can be suitably used as a photoacid generator because it is capable of sensing high-energy radiation and thereby generating a fluorine-containing sulfonic acid of high acidity.

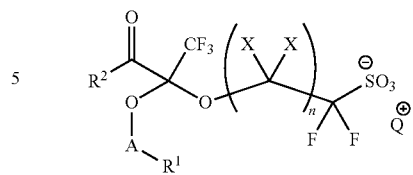

(2)

In the general formula (2), X, n, A, $R^1$ and $R^2$ have the same meanings as in the general formula (4); and $Q^+$ represents a sulfonium cation of the general formula (a) or an iodonium cation of the general formula (b).

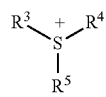

(a)

In the general formula (a), $R^3$, $R^4$ and $R^5$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group. Two or more of $R^3$, $R^4$ and $R^5$ may be bonded together to form a ring with a sulfur atom in the formula.

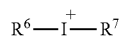

(b)

In the general formula (b), $R^6$ and $R^7$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group. $R^6$ and $R^7$ may be bonded together to form a ring with an iodine atom in the formula.

As specific structural examples of $Q^+$, the sulfonium cation of the general formula (a) and the iodonium cation of the general formula (b) will be described below in detail.

<Sulfonium Cation of General Formula (a)>

In the general formula (a), $R^3$, $R^4$ and $R^5$ are exemplified as follows.

The substituted or unsubstituted $C_1$-$C_{20}$ alkyl group is a straight, branched or cyclic $C_1$-$C_{20}$ alkyl group that may have a substituent. Examples of the substituted or unsubstituted $C_1$-$C_{20}$ alkyl group are methyl, ethyl, n-propyl, isopropyl, cyclopropyl, n-butyl, sec-butyl, isobutyl, tert-butyl, n-pentyl, cyclopentyl, n-hexyl, n-heptyl, 2-ethylhexyl, cyclohexyl, cycloheptyl, 4-methylcyclohexyl, cyclohexylmethyl, n-octyl, n-decyl, 1-adamantyl, 2-adamantyl, bicyclo[2.2.1]heptene-2-yl, 1-adamantanemethyl and 2-adamantanemethyl.

The substituted or unsubstituted $C_1$-$C_{20}$ alkenyl group is a straight, branched or cyclic $C_1$-$C_{20}$ alkenyl group that may have a substituent. Examples of the substituted or unsubstituted $C_1$-$C_{20}$ alkenyl group are vinyl, allyl, propenyl, butenyl, hexenyl and cyclohexenyl.

The substituted or unsubstituted $C_1$-$C_{20}$ oxoalkyl group is a straight, branched or cyclic $C_1$-$C_{20}$ oxoalkyl group that may have a substituent. Examples of the substituted or unsubstituted $C_1$-$C_{20}$ oxoalkyl group are 2-oxocyclopentyl, 2-oxocyclohexyl, 2-oxopropyl, 2-oxoethyl, 2-cyclopentyl-2-oxoethyl, 2-cyclohexyl-2-oxoethyl and 2-(4-methylcyclohexyl)-2-oxoethyl.

Examples of the substituted or unsubstituted $C_6$-$C_{18}$ aryl group are: phenyl; naphthyl; thienyl; alkoxylphenyl such as p-methoxyphenyl, m-methoxyphenyl, o-methoxyphenyl, p-ethoxypenyl, p-tert-butoxyphenyl or m-tert-butoxyphenyl; alkylphenyl such as 2-methylphenyl, 3-methylphenyl, 4-methylphenyl or ethylphenyl; alkylnaphthyl such as methylnaphthyl or ethylnaphthyl; dialkylnaphthyl such as diethylnaphthyl; and dialkoxynaphthyl such as dimethoxynaphthyl or diethoxynaphthyl.

Examples of the substituted or unsubstituted $C_6$-$C_{18}$ aralkyl group are benzyl, 1-phenylethyl and 2-phenylethyl. Examples of the substituted or unsubstituted $C_6$-$C_{18}$ aryloxoalkyl group are 2-aryl-2-oxoethyl such as 2-phenyl-2-oxoethyl, 2-(1-naphthyl)-2-oxoethyl or 2-(2-naphthyl)-2-oxoethyl.

In the case where two or more of $R^3$, $R^4$ and $R^5$ are bonded together to form a ring with the sulfur atom, there can be used divalent groups such as 1,4-butylene and 3-oxa-1,5-penthylene.

There can also be used aryl groups with polymerizable substituents such as acryloyloxy and methacryloyloxy. Examples of the aryl groups with the polymerizable substituents are 4-(acryloyloxy)phenyl, 4-(methacryloyloxy)phenyl, 4-vinyloxyphenyl and 4-vinylphenyl.

Specific examples of the sulfonium cation of the general formula (a) are triphenylsulfonium, (4-tert-butylphenyl)diphenylsulfonium, bis(4-tert-butylphenyl)phenylsulfonium, tris(4-tert-butylphenyl)sulfonium, (3-tert-butylphenyl)diphenylsulfonium, bis(3-tert-butylphenyl)phenylsulfonium, tris(3-tert-butylphenyl)sulfonium, (3,4-di-tert-butylphenyl)diphenylsulfonium, bis(3,4-di-tert-butylphenyl)phenylsulfonium, tris(3,4-di-tert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl 2-thienylsulfonium, 4-n-butoxynaphthyl-1-thiacyclopentanium, 2-n-butoxynaphthyl-1-thiacyclopentanium, 4-methoxynaphthyl-1-thiacyclopentanium and 2-methoxynaphthyl-1-thiacyclopentanium. Among others, preferred are triphenylsulfonium, (4-tert-buthylphenyl)diphenylsulfonium, (4-tert-butoxyphenyl)diphenylsulfonium, tris(4-tert-butylphenyl)sulfonium and (4-tert-butoxycarbonylmethyloxyphenyl)diphenylsulfonium.

Further, 4-(methacryloyloxy)phenyldiphenylsulfonium, 4-(acryloyloxy)phenyldiphenylsulfonium, 4-(methacryloyloxy)phenyldimethylsulfonium and 4-(acryloyloxy)phenyldimethylsulfonium are other specific examples of the sulfonium cation of the general formula (a). As such polymerizable sulfonium cations, there can be used those disclosed in Japanese Laid-Open Patent Publication No. 4-230645 and Japanese Laid-Open Patent Publication No. 2005-84365.

<Iodonium Cation of General Formula (b)>

Examples of $R^6$ and $R^7$ in the general formula (b) are the same as those of $R^3$, $R^4$ and $R^5$ in the general formula (a).

Specific examples of the iodonium cation of the general formula (b) are bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium and (4-methacryloyloxy)phenylphenyliodonium. Among others, bis(4-tert-butylphenyl)iodonium is preferred.

More specifically, the polymerizable fluorine-containing sulfonic acid onium salt of the general formula (2) corresponds to any combination of the previously-exemplified polymerizable fluorine-containing sulfonate having the anion structure of the general formula (1) with either the sulfonium cation of the general formula (a) or the iodonium cation of the general formula (b) exemplified above.

Preferred examples of the fluorine-containing sulfonic acid onium salt are those indicated below.

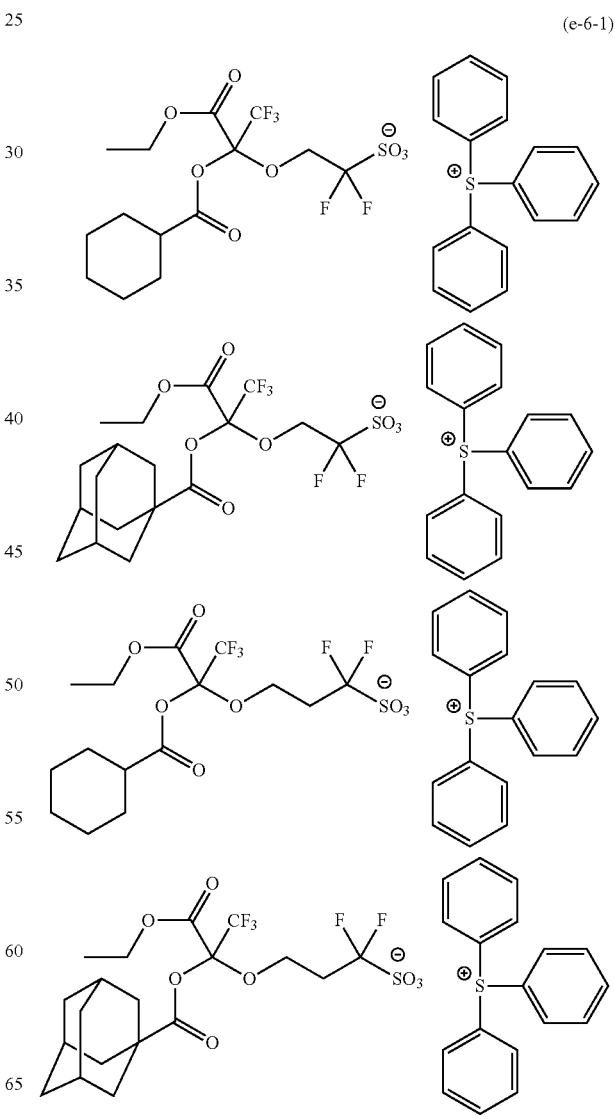

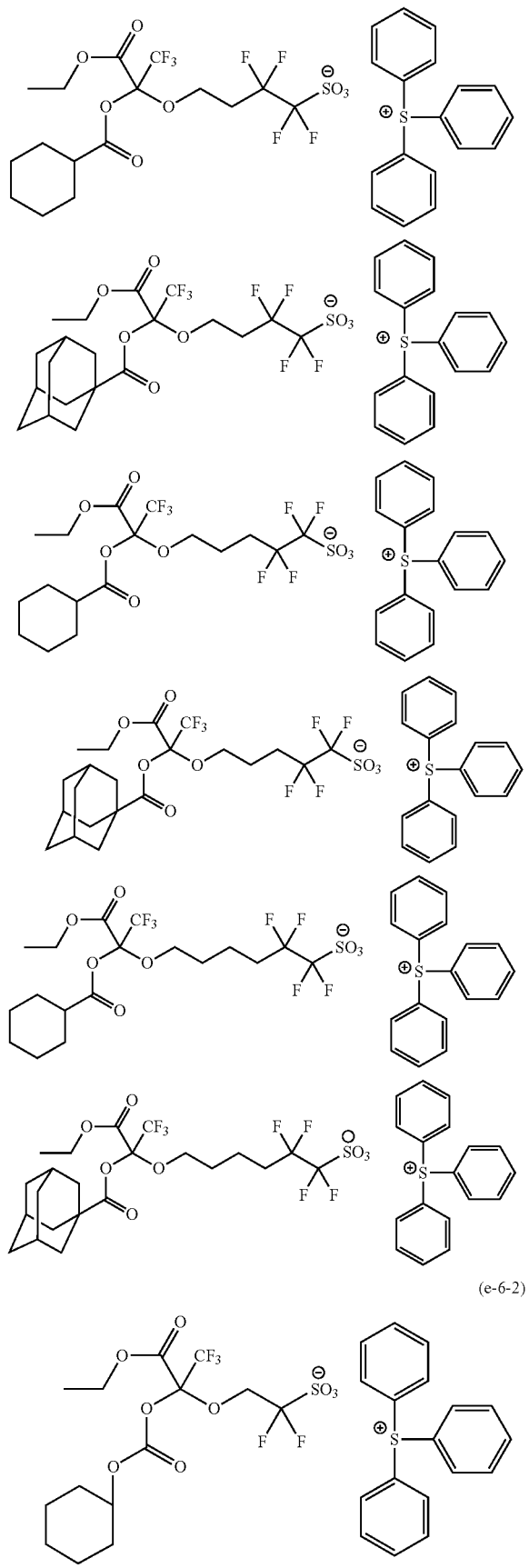
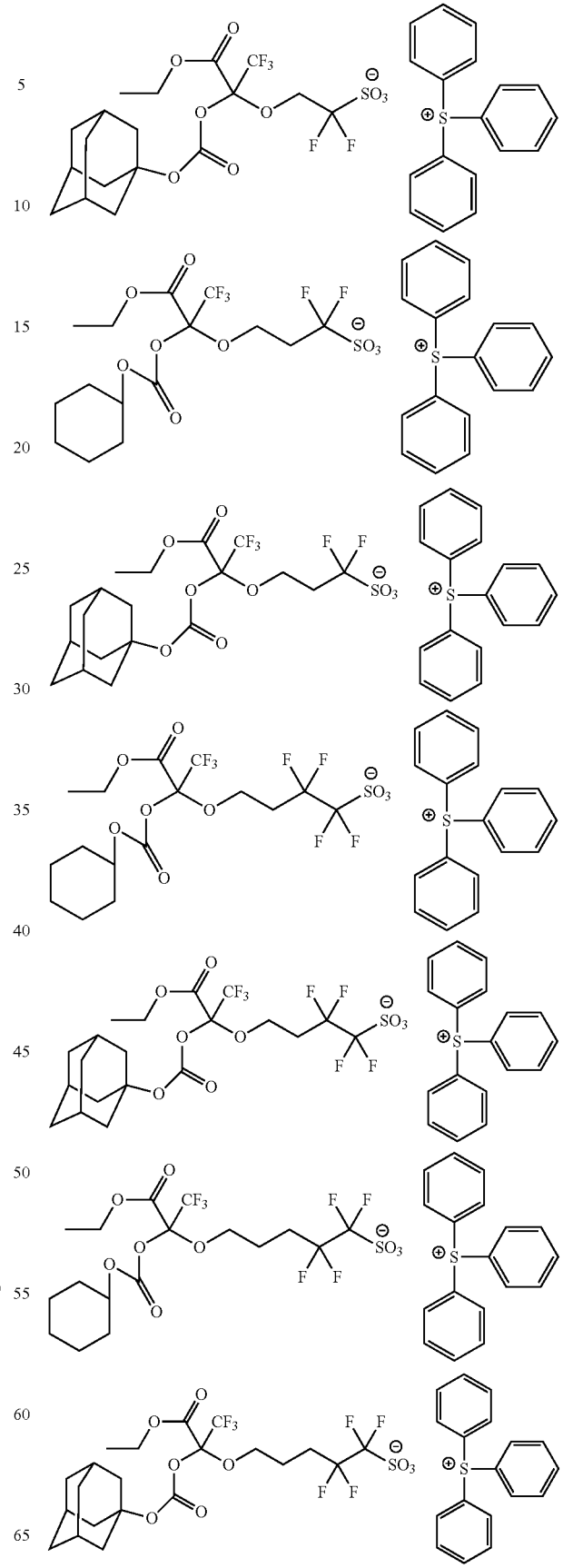
(e-6-2)

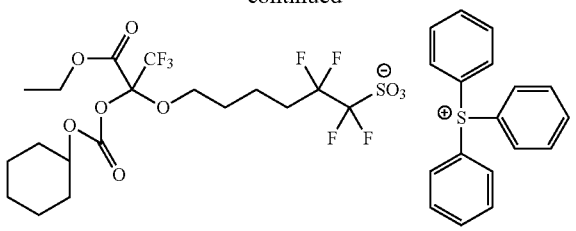
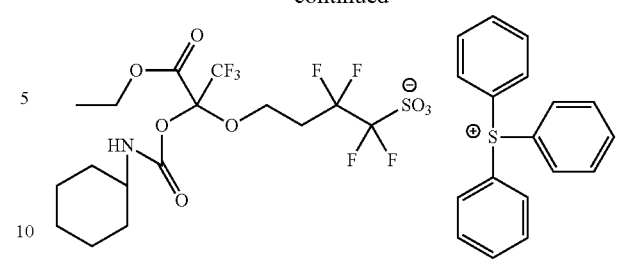
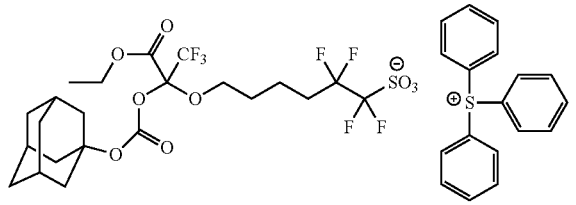
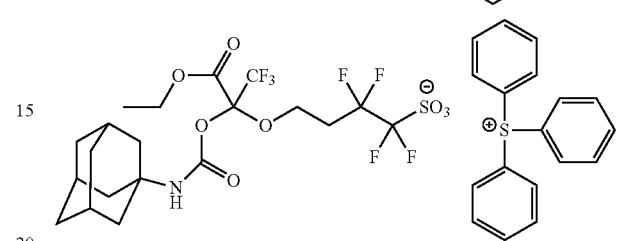
(e-6-3)
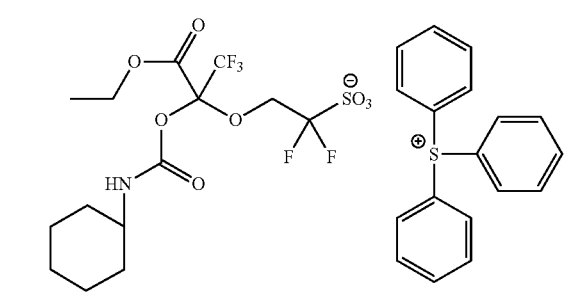
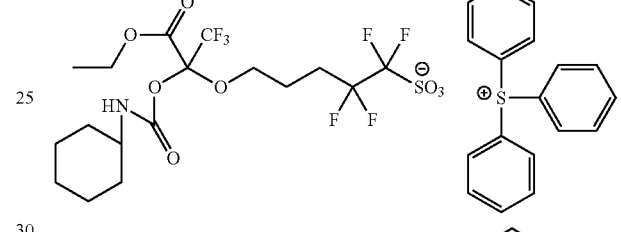
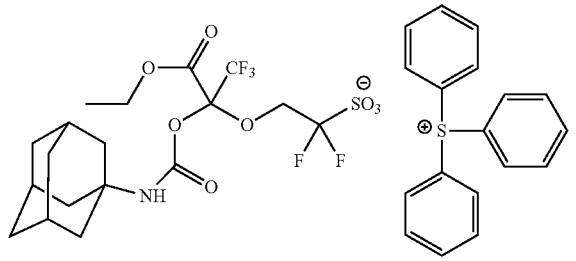
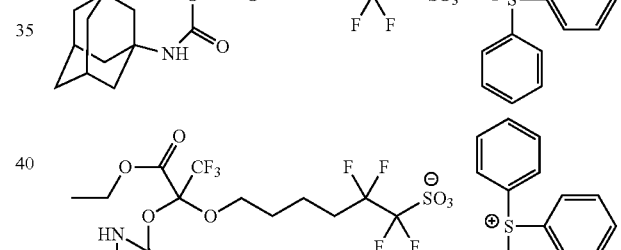
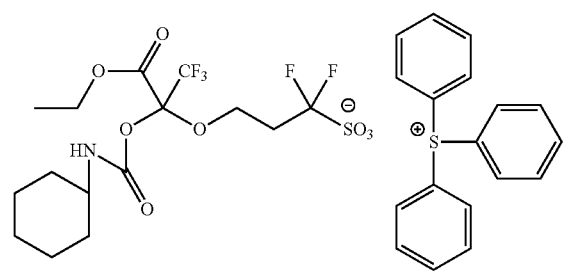
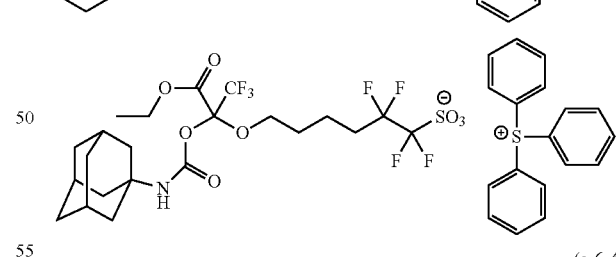
(e-6-4)
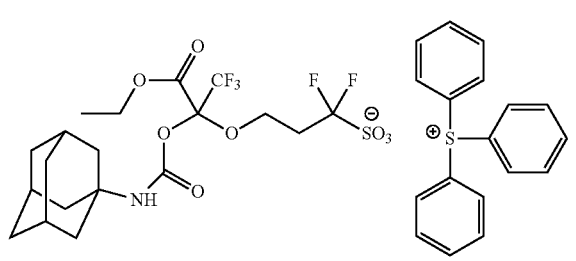
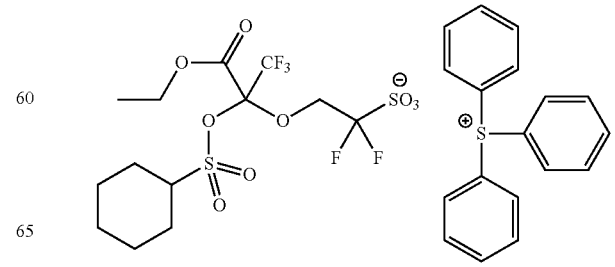

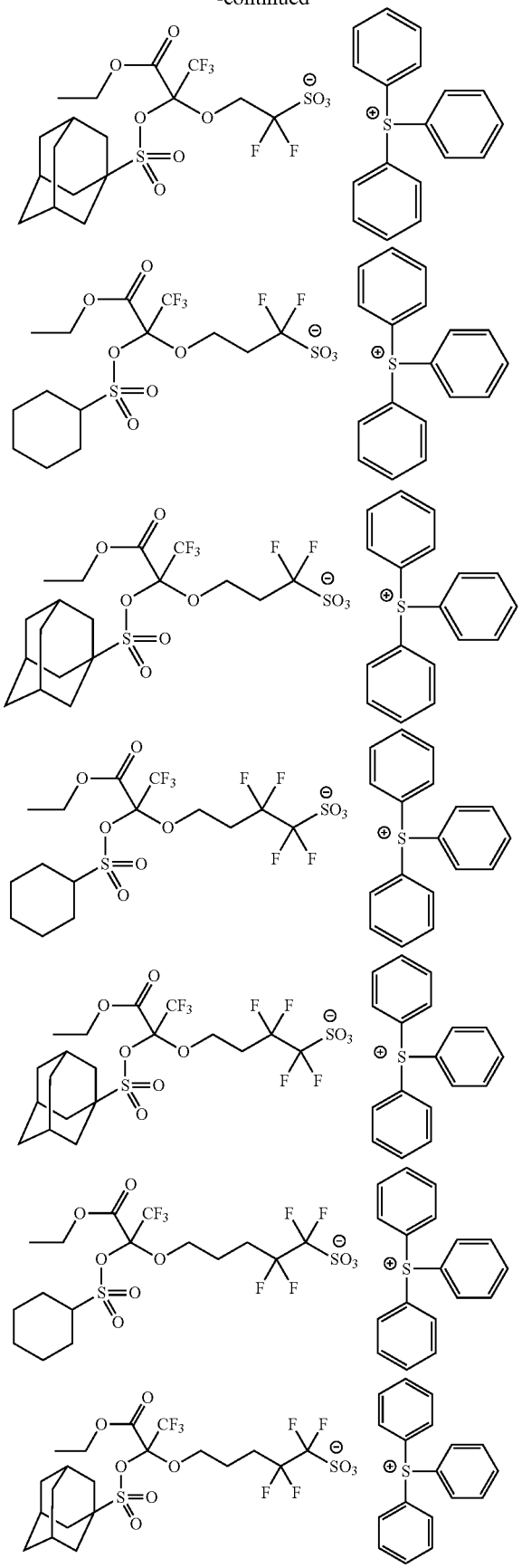

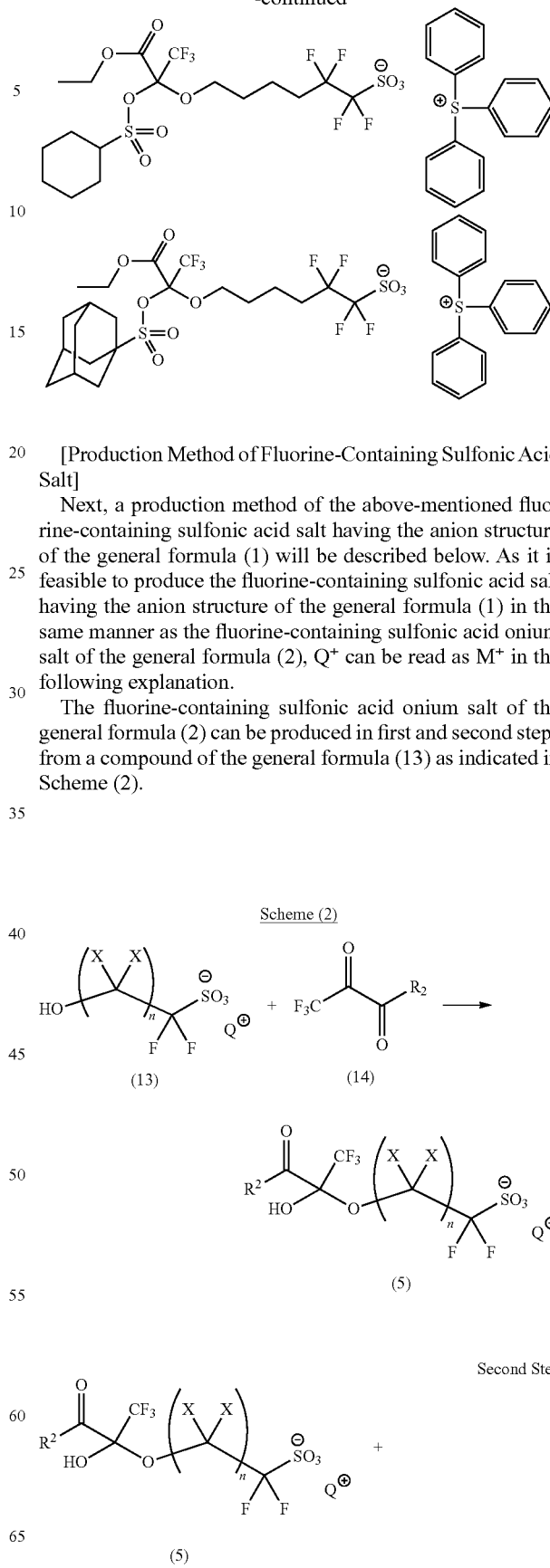

[Production Method of Fluorine-Containing Sulfonic Acid Salt]

Next, a production method of the above-mentioned fluorine-containing sulfonic acid salt having the anion structure of the general formula (1) will be described below. As it is feasible to produce the fluorine-containing sulfonic acid salt having the anion structure of the general formula (1) in the same manner as the fluorine-containing sulfonic acid onium salt of the general formula (2), $Q^+$ can be read as $M^+$ in the following explanation.

The fluorine-containing sulfonic acid onium salt of the general formula (2) can be produced in first and second steps from a compound of the general formula (13) as indicated in Scheme (2).

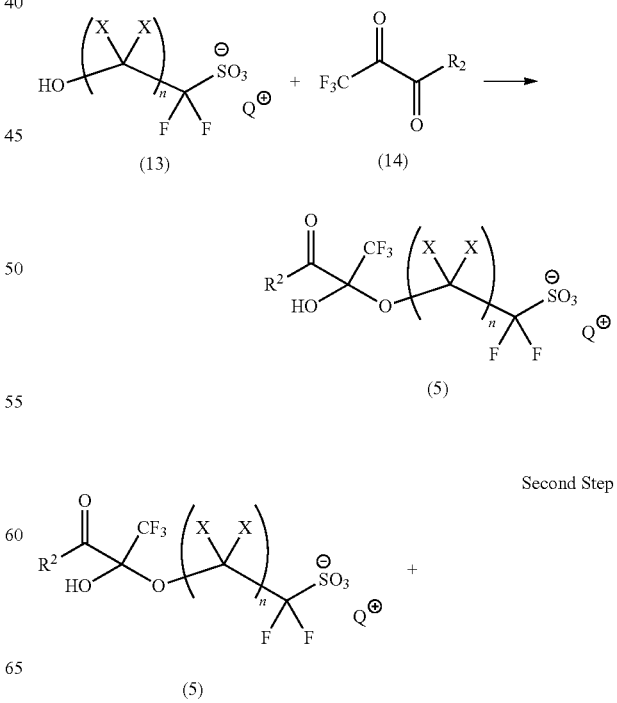

-continued

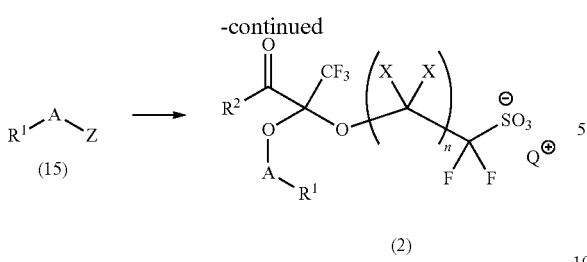

(2)

In Scheme (2), X, n, A, R¹, R² and Q⁺ have the same meanings as in the general formula (4) or in the general formula (2); and Z represents a hydroxyl group, a halogen atom or a —O-A-R¹ group, or the combination of Z and A as -A-Z represents a —NCO group.

The general formula (13) represents a hydroxyfluoroalkanesulfonic acid onium salt. As the compound of the general formula (13), there can be used 2-hydroxy-1,1-difluoroethanesulfonic acid triphenylsulfonium, 4-hydroxy-1,1,2,2-tetrafluorobutanesulfonic acid triphenylsulfonium, 5-hydroxy-1,1,2,2-tetrafluoropentanesulfonic acid triphenylsulfonium and 6-hydroxy-1,1,2,2-tetrafluorohexanesulfonic acid triphenylsulfonium. These compounds can be prepared by methods as disclosed in Japanese Laid-Open Patent Publication No. 2009-91351, International Application Publication No. WO 2008/56795, International Application Publication No. WO 2006/121096 and Japanese Laid-Open Patent Publication No. 2010-18573.

The general formula (14) represents a trifluoropyruvic acid derivative. $R^2$ is either $R^AO$ or $R^BR^CN$. $R^A$, $R^B$ and $R^C$ are each independently a hydrogen atom, a $C_1$-$C_{20}$ alkyl group, a $C_2$-$C_{20}$ alkenyl group, a $C_2$-$C_{20}$ oxoalkyl group, a $C_6$-$C_{18}$ aryl group, a $C_6$-$C_{18}$ aralkyl group or a $C_3$-$C_{30}$ lactone group. $R^B$ and $R^C$ may be bonded to each other to form a 3- to 18-membered heterocyclic ring. Any of hydrogen atoms on carbons in $R^A$, $R^B$ and $R^C$ may be substituted with a substituent. Examples of $R^2$ are the same as those in the explanation of the general formula (4).

The compound of the general formula (14) can be commercially available and used as it is or can be prepared by known methods.

The general formula (15) represents the following compound depending on the structure of A.
(1) In the case where A is represented by the following formula

In this case, the compound of the general formula (15) is either a carboxylic acid of the general formula (16), a carboxylic acid halide of the general formula (17) or a carboxylic acid anhydride of the general formula (18).

In the general formula (16), R¹ has the same meaning as in the general formula (1).

In the general formula (17), R¹ has the same meaning as in the general formula (1); and X' represents fluorine, chlorine, bromine or iodine.

In the general formula (18), R¹ has the same meaning as in the general formula (1).
(2) In the case where A is represented by the following formula

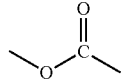

In this case, the compound of the general formula (15) is an alkyl carbonate halide of the general formula (19).

In the general formula (19), R¹ has the same meaning as in the general formula (1); and X' represents fluorine, chlorine, bromine or iodine.
(3) In the case where A is represented by the following formula

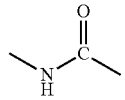

In this case, the compound of the general formula (15) is an isocyanate of the general formula (20).

In the general formula (20), R¹ has the same meaning as in the general formula (1).
(4) In the case where A is represented by the following formula

In this case, the compound of the general formula (15) is a sulfonic acid of the general formula (21), a sulfonic acid halide of the general formula (22) or a sulfonic acid anhydride of the general formula (23).

In the general formula (21), R¹ has the same meaning as in the general formula (1).

In the general formula (22), R¹ has the same meaning as in the general formula (1); and X' represents fluorine, chlorine, bromine or iodine.

In the general formula (23), R¹ has the same meaning as in the general formula (1).

The compound of the general formula (15) can be commercially available and used as it is or can be prepared by known methods.

(First Step)

The first step will be next explained below. In the first step, the trifluoropyruvic acid derivative of the general formula (14) is added to the hydroxyfluoroalkanesulfonic acid onium salt of the general formula (13). This addition reaction can be performed by reacting the hydroxyfluoroalkanesulfonic acid onium salt of the general formula (13) with the trifluoropyruvic acid derivative of the general formula (14) in the presence of an acid catalyst or in the presence of no catalyst.

There is no particular limitation on the amount of the trifluoropyruvic acid derivative of the general formula (14) reacted with the hydroxyfluoroalkanesulfonic acid onium salt of the general formula (13). The amount of the trifluoropyruvic acid derivative is generally 0.1 to 5 mol, preferably 0.2 to 3 mol, more preferably 0.5 to 2 mol, most preferably 0.8 to 1.5 mol, per 1 mol of the hydroxyfluoroalkanesulfonic acid onium salt.

In general, it is preferable to perform the addition reaction with the use of an aprotic solvent although the addition reaction can be performed in the presence or absence of a solvent. Examples of the aprotic solvent are diisopropyl ether, dichloroethane, chloroform, toluene, ethylbenzene, monochlorobenzene, acetonitrile and N,N-dimethylformamide. These solvents can be used solely or in combination of two or more kinds thereof.

There is no particular limitation on the reaction temperature. The reaction temperature is generally 0 to 100° C., preferably 10 to 80° C. It is preferable to perform the reaction with stirring.

The reaction time is generally several minutes to 100 hours, preferably 30 minutes to 50 hours, more preferably 1 to 20 hours although the reaction time varies depending on the reaction temperature. It is preferable to determine the time at which the raw material, i.e., the hydroxyfluoroalkanesulfonic acid onium salt has been consumed as the end of the reaction while monitoring the progress of the reaction by any analytical means such as nuclear magnetic resonance (NMR).

Although the reaction is generally performed in the presence of no catalyst, the reaction proceeds in the same manner even in the presence of the acid catalyst. As the acid catalyst, an organic acid such as p-toluenesulfonic acid and/or an inorganic acids such as sulfuric acid can be used.

After the completion of the reaction, the target fluorine-containing sulfonic acid onium salt of the general formula (5) can be obtained by removing the solvent etc. under a reduced pressure.

The fluorine-containing sulfonic acid onium salt of the general formula (5) can be purified by ordinary means such as extraction or recrystallization after the completion of the reaction.

Alternatively, the reaction-completed solution may be used as it is, without removing the solvent, as raw material for production of the fluorine-containing sulfonic acid onium salt of the general formula (2).

(Second Step)

The second step will be explained below. In the second step, the fluorine-containing sulfonic acid onium salt of the general formula (2) is formed by reaction of the fluorine-containing sulfonic acid onium salt of the general formula (5) and the compound of the general formula (15).

Although the compound of the general formula (15) varies depending on the structure of A as mentioned above, the reaction itself can be performed in the same manner in each case. By way of example, the following explanation will refer to the esterification reaction in the case where A is represented by the following formula.

Even in the case of the compound where A has any other structure, the reaction can be readily performed by those skilled in the art based on the following explanation.

It is feasible to perform the esterification reaction by any known process such as dehydration condensation of the carboxylic acid of the general formula (16) with the fluorine-containing sulfonic acid onium salt of the general formula (5) in the presence of an acid catalyst (as is known as Fischer ester synthesis reaction), reaction of the carboxylic acid halide of the general formula (17) or the carboxylic acid anhydride of the general formula (18) with the fluorine-containing sulfonic acid onium salt of the general formula (5) etc.

In the case of the carboxylic acid of the general formula (16), there is no particular limitation on the amount of the carboxylic acid reacted with the fluorine-containing sulfonic acid onium salt. The amount of the carboxylic acid is generally 0.1 to 5 mol, preferably 0.2 to 3 mol, more preferably 0.5 to 2 mol, most preferably 0.8 to 1.5 mol, per 1 mol of the fluorine-containing sulfonic acid onium salt.

In general, it is preferable to perform the esterification reaction with the use of an aprotic solvent although the esterification reaction can be performed in the presence or absence of a solvent. Examples of the aprotic solvent are dichloroethane, toluene, ethylbenzene, monochlorobenzene, acetonitrile and N,N-dimethylformamide. These solvents can be used solely or in combination of two or more kinds thereof.

As the fluorine-containing sulfonic acid onium salt is almost insoluble in an aromatic hydrocarbon solvent such as toluene, ethylbenzene or monochlorobenzene, the mixture of the fluorine-containing sulfonic acid onium salt and the aromatic hydrocarbon solvent is in slurry form. Even in such a state, the reaction proceeds sufficiently.

There is no particular limitation on the reaction temperature. The reaction temperature is generally 0 to 200° C., preferably 20 to 180° C., more preferably 50 to 150° C. It is preferable to perform the reaction with stirring.

The reaction time is generally several minutes to 100 hours, preferably 30 minutes to 50 hours, more preferably 1 to 20 hours although the reaction time varies depending on the reaction temperature. It is preferable to determine the time at which the raw material, i.e., the fluorine-containing sulfonic acid onium salt of the general formula (5) has been consumed as the end of the reaction while monitoring the progress of the reaction by any analytical means such as gas chromatography (GC) or nuclear magnetic resonance (NMR).

The reaction is generally performed in the presence of a catalyst, preferably an acid catalyst. It is feasible to select and use any known esterification reaction catalyst. For example, an organic acid such as p-toluenesulfonic acid and/or an inorganic acids such as sulfuric acid can be used as the acid catalyst. A dehydrating agent such as 1,1'-carbonyldiimidazole or N,N'-dicyclohexylcarbodiimide may be added to the reaction system. There is no particular limitation on the amount of the acid catalyst used. The amount of the acid catalyst is generally 0.0001 to 10 mol, preferably 0.001 to 5 mol, more preferably 0.01 to 1.5 mol, per 1 mol of the fluorine-containing sulfonic acid onium salt.

It is preferable to perform the esterification reaction using the acid catalyst while dehydrating the reaction system e.g. by means of a Dean-Stark apparatus for reduction of the reaction time. After the completion of the reaction, the target fluorine-containing sulfonic acid onium salt of the general formula (2) can be obtained by any ordinary means such as extraction, reprecipitation or recrystallization. Further, the fluorine-containing sulfonic acid onium salt can be purified by recrystallization etc. as needed.

In the case of the carboxylic acid halide of the general formula (17) or the carboxylic acid anhydride of the general formula (18), there is no particular limitation on the amount of the carboxylic acid halide or carboxylic acid anhydride reacted with the fluorine-containing sulfonic acid onium salt. The amount of the carboxylic acid halide or carboxylic acid anhydride is generally 0.1 to 5 mol, preferably 0.2 to 3 mol, more preferably 0.5 to 2 mol, most preferably 0.8 to 1.5 mol, per 1 mol of the fluorine-containing sulfonic acid onium salt.

The reaction can be performed with the use of no solvent or any solvent inert to the reaction. There is no particular limitation on the solvent as long as the solvent is inert to the reaction. For example, it is feasible to perform the reaction in water, an organic solvent or a mixed solvent of water and an organic solvent. Example of the organic solvent are: ketone solvents such as acetone, methyl ethyl ketone and methyl isobutyl ketone; ester solvents such as ethyl acetate and butyl acetate; ether solvents such as diethyl ether, diethylene glycol dimethyl ether, tetrahydrofuran and dioxane; halogenated solvents such as dichloromethane, chloroform, carbon tetrachloride, 1,2-dichloroethane, tetrachloroethylene, chlorobenzene and oxochlorobenzene; and polar solvents such as acetonitrile, N,N-dimethylformamide, N,N-dimethylimidazolidinone, dimethyl sulfoxide and sulfolane. These organic solvents can be used solely or in combination of two or more thereof.

There is no particular limitation on the reaction temperature. The reaction temperature is generally −78 to 150° C., preferably −20 to 120° C., more preferably 0 to 100° C.

The reaction time is generally several minutes to 100 hours, preferably 30 minutes to 50 hours, more preferably 1 to 20 hours although the reaction time varies depending on the reaction temperature. It is preferable to determine the time at which the raw material, i.e., the fluorine-containing sulfonic acid onium salt has been consumed as the end of the reaction while monitoring the progress of the reaction by any analytical means such as gas chromatography (GC) or nuclear magnetic resonance (NMR).

It is feasible, in the case of using the carboxylic acid halide of the general formula (17), to perform the reaction in the presence of no catalyst while removing a hydrogen halide by-product (such as hydrogen chloride) from the reaction system. It is alternatively feasible to perform the reaction with the use of a dehydrohalogenating agent (as an acid acceptor).

Examples of the acid acceptor are: organic bases such as triethylamine, pyridine, picoline, dimethylaniline, diethylaniline, 1,4-diazabicyclo[2.2.2]octane (DABCO) and 1,8-diazabicyclo[5.4.0]undeca-7-ene (DBU); and inorganic bases such as sodium hydrogen carbonate, sodium carbonate, potassium carbonate, lithium carbonate, sodium hydroxide, potassium hydroxide, calcium hydroxide and magnesium oxide. There is no particular limitation on the amount of the acid acceptor used. The amount of the acid acceptor is generally 0.05 to 10 mol, preferably 0.1 to 5 mol, more preferably 0.5 to 3 mol, per 1 mol of the fluorine-containing sulfonic acid onium salt.

After the completion of the reaction, the target fluorine-containing sulfonic acid onium salt of the general formula (2) can be obtained by any ordinary means such as extraction, distillation or recrystallization. Further, the fluorine-containing sulfonic acid onium salt can be purified by washing, recrystallization etc. as needed.

[Resist Composition]

A resist composition according to the present invention includes a base resin, an acid generator and a solvent and may optionally include various additives such as a basic compound, a plasticizer, a leveling agent, a surfactant, an additive resin, a stabilizer, a coloring agent, a viscosity improver, an antifoaming agent, a compatibilizer, a primer and an antioxidant.

[Base Resin]

The base resin of the resist composition according to the present invention will be explained below. The base resin is either a resin that is insoluble in an alkali solution before light irradiation and is made soluble in an alkali solution upon elimination of an acid labile group from the resin by the action of an acid generated from the acid generator under light irradiation, or a resin that is soluble in an alkali solution before light irradiation and is made insoluble in an alkali solution upon reaction of a neutral hydroxyl group of the resin with a cross-linking agent by the action of an acid generated from the acid generator under light irradiation, for use in the positive or negative resist composition.

Examples of the base resin are homopolymers or copolymers (hereinafter sometimes referred to as "(co)polymers") obtained by (co)polymerization of one kind of monomer, or two or more kinds of monomers, selected from the group consisting of acrylic esters, fluorine-containing acrylic esters, methacrylic esters, fluorine-containing methacrylic esters, styrenic compounds, fluorine-containing styrenic compounds, vinyl ethers, fluorine-containing vinyl ethers, allyl ethers, fluorine-containing allyl ethers, acrylamides, methacrylamides, vinyl esters, allyl esters, olefins, fluorine-containing olefins, norbornene compounds and fluorine-containing norbornene compounds.

It is preferable to prepare a polymer with an acid labile group or a neutral hydroxyl group as the base resin, by (co)polymerization of any of the above monomers having an acid labile group or a neutral hydroxyl group, for ease of preparation. Alternatively, a polymer with an acid labile group or a neutral hydroxyl group may be prepared by forming a polymer with no acid labile group etc., and then, introducing an acid labile group etc. through polymer reaction.

The base resin can consist of a repeating unit (A) having an acid labile group on a side chain thereof or a repeating unit (B) having a neutral hydroxyl group on a side chain thereof so as to serve as a resist function. The base resin may alternatively be in the form of a copolymer having any repeating unit or units other than the repeating unit (A) or (B). It is feasible to use any other repeating unit or units in combination appropriately for control of resist dry etching resistance, alkali developer (standard developer) compatibility, substrate adhesion, resist profile and other generally required resist characteristics such as resolution, heat resistance, water repellency and sensitivity in addition to the resist function.

The base resin generally has a mass-average molecular weight of 1,000 to 1,000,000, preferably 2,000 to 500,000, as measured by gel permeation chromatography (GPC). If the mass-average molecular weight of the base resin is less than 1,000, a film of the resist composition (i.e. resist film) does not attain sufficient strength. If the mass-average molecular weight of the base resin exceeds 1,000,000, the solubility of the base resin in the solvent becomes lowered so that it is unfavorably difficult to form the resist composition into a smooth film. The molecular weight distribution (Mw/Mn) of the base resin is preferably in the range of 1.01 to 5.00, more preferably 1.01 to 4.00, still more preferably 1.01 to 3.00, most preferably 1.10 to 2.50.

The base resin generally contains 1 to 100 mol %, preferably 1 to 99 mol %, still more preferably 5 to 80 mol %, particularly preferably 10 to 60 mol %, of the repeating unit having the acid labile group or neutral hydroxyl group to serve as the resist function. If the amount of the acid labile group- or neutral hydroxyl group-containing repeating unit is less than 1 mol %, the change in the solubility of the base resin in a developer solubility by exposure becomes unfavorably too small. Further, the base resin can contain 5 to 99 mol %, preferably 20 to 95 mol %, more preferably 40 to 90 mol %, of the repeating unit with no resist function. If the amount of the repeating unit with no resist function is less than 5 mol %, the substrate adhesion of the resist composition may not be improved. If the amount of the repeating unit with no resist function exceeds 99 mol %, the amount of the repeating unit with the resist function becomes unfavorably small. In addition, it may not possible to secure sufficient sensitivity and solubility change.

<Repeating Unit>

The base resin has at least either one of repeating units (A) and (B) of the general formulas (24-1) and (24-2) and may have a repeating unit (C) of the general formula (24-3).

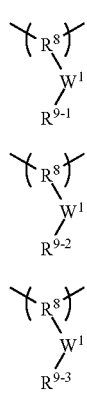

(24-1)

(24-2)

(24-3)

In the general formulas (24-1), (24-2) and (24-3), $R^8$ represents a group formed by cleavage of a polymerizable double bond-containing group of a monomer; $R^{9-1}$ represents an acid labile group; $R^{9-2}$ represents a neutral hydroxyl-containing group; $R^{9-3}$ represents a group other than the acid labile group and the neutral hydroxyl-containing group; W represents a divalent linking group formed by one kind of atomic group or two or more kind of atomic groups selected from the group consisting of single bond, substituted or unsubstituted methylene group, divalent alicyclic hydrocarbon group, divalent aromatic hydrocarbon group, substituted or unsubstituted condensed polycyclic aromatic group, divalent heterocyclic group, ether group, carbonyl group, ester bond, oxycarbonyl bond, thioether group, amide bond, sulfoneamide bond, urethane bond and urea bond. The linking group may have a plurality of atomic groups of the same kind. Any number of hydrogen atoms bonded to carbon atoms in the linking group may be substituted with a fluorine atom. Any atoms in the linking group may be bonded to each other to form a ring structure.

Preferably, $R^8$ is any one of groups of the following formulas.

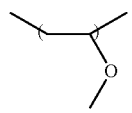 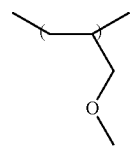 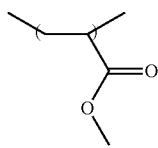

(E-7)

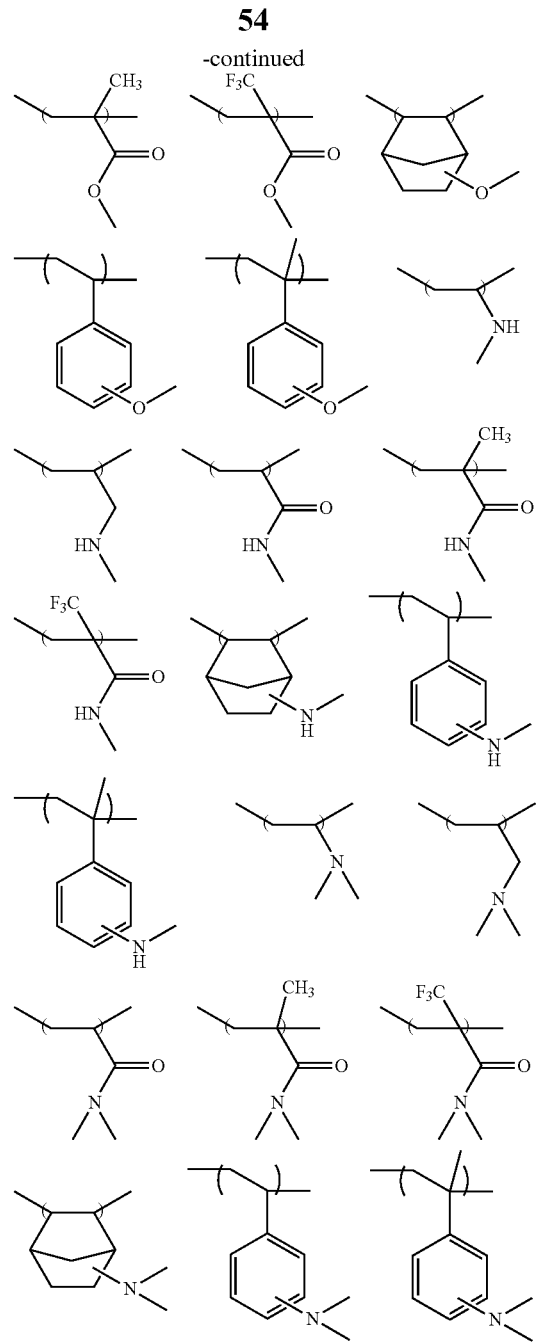

Namely, $R^8$ is any one of groups formed by cleavage of double bonds of the following polymerizable double bond-containing groups.

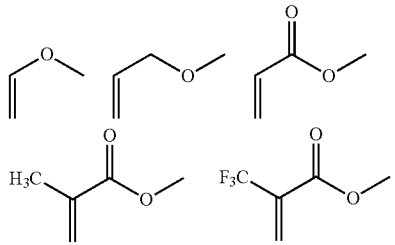

(E-8)

-continued

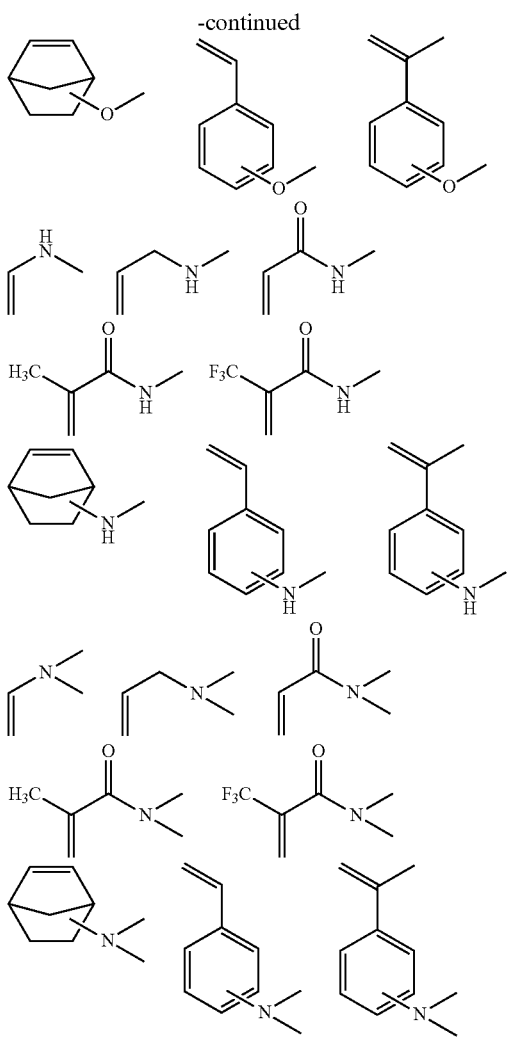

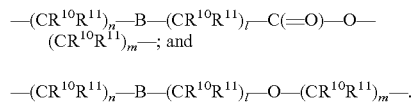

In the case of the repeating unit (A), the linking group $W^1$ provides a link as represented by ($R^8$: main chain)-$W'$—C(=O)—O—($R^{9-1}$: acid labile group) or ($R^8$: main chain)-$W'$—O—($R^{9-1}$: acid labile group) assuming the linking group as $W'$. The terminal end of $W'$—$R^{9-1}$ has an ester structure (—C(=O)$OR^{9-1}$; alkoxycarbonyl group) or an ether structure (—O—$R^{9-1}$; alkoxy group). In the case of the repeating unit (B), the linking group $W^1$ provides a link as represented by ($R^8$: main chain)-$W'$—C(=O)—O—$R^{9-2}$ or ($R^8$: main chain)-$W'$—O—$R^{9-2}$ assuming the linking group as $W'$. The terminal end of $W'$—$OR^{9-2}$ has a carboxyl group (—C(=O)OH) or a hydroxy group (—O—H). In the case of the repeating unit (C), the linking group $W^1$ provides a link as represented by ($R^8$: main chain)-$W'$—$R^{9-3}$ assuming the linking group as $W'$.

Examples of the combined linking group $W'$ are:

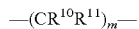

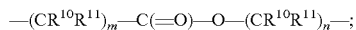

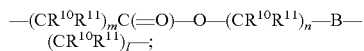

—$(CR^{10}R^{11})_m$—O—$(CR^{10}R^{11})_n$—;

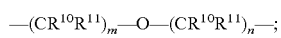

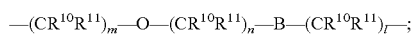

—$(CR^{10}R^{11})_n$—B—$(CR^{10}R^{11})_l$—C(=O)—O—$(CR^{10}R^{11})_m$—; and

—$(CR^{10}R^{11})_n$—B—$(CR^{10}R^{11})_l$—O—$(CR^{10}R^{11})_m$—.

Herein, $R^{10}$ and $R^{11}$ each represents a monovalent organic group; and l, m and n each independently represent an integer of 0 to 10. It is preferable that m is 0 to 4 and each of l and n is 0 or 1. Further, B represents a divalent cyclic group selected from alicyclic and aromatic hydrocarbon groups.

There is no particular limitation on the monovalent organic groups $R^{10}$ and $R^{11}$ in the above substituted methylene groups. $R^{10}$ and $R^{11}$ each independently represents a hydrogen atom, a hydroxyl group or a monovalent $C_1$-$C_{30}$ group selected from substituted or unsubstituted alkyl group, substituted or unsubstituted alicyclic hydrocarbon group, substituted or unsubstituted alkoxy group, substituted or unsubstituted aryl group, substituted or unsubstituted condensed polycyclic aromatic group and monocyclic or polycyclic heterocyclic group. The monovalent organic group may have a fluorine atom, an oxygen atom, a sulfur atom, a nitrogen atom or a carbon-carbon double bond. $R^{10}$ and $R^{11}$ can be the same or different. In the case where the methylene group contains a plurality of $R^{10}$ or $R^{11}$, $R^{10}$ or $R^{11}$ can be the same or different. Further, $R^{10}$ and $R^{11}$ may be bonded together to form a ring structure, preferably an alicyclic hydrocarbon structure, with any other atom in the molecule. The monovalent organic groups $R^{10}$ and $R^{11}$ are exemplified as follows.

It is preferable that $R^{10}$ and $R^{11}$ are each independently a hydrogen atom, a fluorine atom, an alkyl group, a substituted alkyl group or an alicyclic hydrocarbon group. One or more hydrogen atoms in $R^{10}$, $R^{11}$ may be substituted with a fluorine atom. Among others, particularly preferred are —$CR^{10}R^{11}$ where $R^{10}$ and $R^{11}$ are each independently a hydrogen atom, a fluorine atom or a lower alkyl group and — (single bond).

More specifically, $R^{10}$ and $R^{11}$ are exemplified as follows. Examples of the acyclic alkyl group are those of 1 to 30 carbon atoms, preferably 1 to 12 carbon atoms, such as methyl, ethyl, n-propyl, i-propyl, n-butyl, 1-methylpropyl, 2-methylpropyl, tert-butyl, n-pentyl, i-pentyl, 1,1-dimethylpropyl, 1-methylbutyl, 1,1-dimethylbutyl, n-hexyl, n-heptyl, i-hexyl, n-octyl, i-octyl, 2-ethylhexyl, n-nonyl, n-decyl, n-undecyl and n-dodecyl. Among others, lower alkyl groups are preferred. Particularly preferred are methyl, ethyl, n-propyl and i-propyl.

Examples of the substituted acyclic alkyl group are those obtained by substitution of one hydrogen atom or two or more hydrogen atoms of the alkyl group with a $C_1$-$C_4$ alkoxy group, a halogen atom, an acyl group, an acyloxy group, a cyano group, a hydroxyl group, a carboxyl group, an alkoxycarbonyl group, a nitro group etc. Among others, fluorine-substituted alkyl groups, i.e., fluoroalkyl groups are preferred. There can preferably be used lower fluoroalkyl groups such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoropropyl.

The alicyclic hydrocarbon group as $R^{10}$, $R^{11}$ or the alicyclic hydrocarbon group formed by $R^{10}$ and $R^{11}$ together with the carbon atom bonded thereto can be monocyclic or polycyclic. Examples of the alicyclic hydrocarbon group are those having a monocyclo, bicyclo, tricycle or tetracyclo structure of 3 or more carbon atoms, preferably 3 to 30 carbon atoms, more preferably 3 to 25 carbon atoms. The alicyclic hydrocarbon group may have a substituent.

As the monocyclic hydrocarbon group, there can preferably be used those having 3 to 12 ring carbon atoms, more preferably 3 to 7 ring carbon atoms. Examples of the monocyclic hydrocarbon group are cyclopropyl, cyclobutyl, cyclopentyl, cyclohexyl, cycloheptyl, cyclooctyl, cyclodecanyl, cyclododecanyl and 4-tert-butylcyclohexyl. As the polycyclic hydrocarbon group, there can preferably be used those having 7 to 15 ring carbon atoms. Examples of the polycyclic hydrocarbon group are adamantyl, noradamantyl, decalin residue, tricyclodecanyl, tetracyclododecanyl, norbornyl and cedrol. The alicyclic hydrocarbon group can be a spiro ring of preferably 3 to 6 carbon atoms. Preferred examples of the spiro ring are adamantyl, decalin residue, norbornyl, cedrol, cyclohexyl, cycloheptyl, cyclooctyl, cyclodecanyl, cyclododecanyl and tricyclodecanyl. One hydrogen atom or two or more hydrogen atoms on the ring carbons of the above organic group, or one hydrogen atom or two or more hydrogen atoms of the above linking group, may be each independently substituted with a substituent such as a $C_1$-$C_{30}$ alkyl or substituted alkyl group, a hydroxy group, an alkoxy group, a carboxyl group or an alkoxycarbonyl group. One hydrogen atom or two or more hydrogen atoms of the substituent may further be substituted with fluorine or trifluoromethyl.

Herein, the $C_1$-$C_{30}$ alkyl group is preferably a lower alkyl group, more preferably an alkyl group selected from the group consisting of methyl, ethyl, propyl and isopropyl. As the substituent of the substituted alkyl group, there can be used a hydroxyl group, a halogen atom, an alkoxy group etc. The alkoxy group is, for example, of 1 to 4 carbon atoms, such as methoxy, ethoxy, propoxy or butoxy. The alkoxycarbonyl group is, for example, methoxycarbonyl, ethoxycarbonyl or isopropoxycarbonyl.

Examples of the alkoxy group are those of 1 to 4 carbon atoms, such as methoxy, ethoxy, propoxy and butoxy.

Examples of the substituted or unsubstituted aryl group are those of 1 to 30 carbon atoms. It is preferable that, when the aryl group is monocyclic, the monocyclic aryl group has 3 to 12 ring carbon atoms, more preferably 3 to 6 ring carbon atoms. As such an aryl group, there can be used phenyl, biphenyl, terphenyl, o-tolyl, m-tolyl, p-tolyl, p-hydroxyphenyl, p-methoxyphenyl, mesityl, o-cumenyl, 2,3-xylyl, 2,4-xylyl, 2,5-xylyl, 2,6-xylyl, 3,4-xylyl, 3,5-xylyl, o-fluorophenyl, m-fluorophenyl, p-fluorophenyl, o-trifluoromethylphenyl, m-trifluoromethylphenyl, p-trifluoromethylphenyl, 2,3-bistrifluoromethylphenyl, 2,4-bistrifluoromethylphenyl, 2,5-bistrifluoromethylphenyl, 2,6-bistrifluoromethylphenyl, 3,4-bistrifluoromethylphenyl, 3,5-bistrifluoromethylphenyl, p-chlorophenyl, p-bromophenyl and p-iodophenyl.

Examples of the substituted or unsubstituted $C_1$-$C_{30}$ condensed polycyclic aromatic group are monovalent organic groups obtained by elimination of one hydrogen atom from pentalene, indene, naphthalene, azulene, heptalene, biphenylene, indacene, acenaphthylene, fluorene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene and the like. One hydrogen atom or two or more hydrogen atoms of the above condensed polycyclic aromatic group may preferably be substituted with a fluorine atom or a $C_1$-$C_4$ alkyl or fluorine-containing alkyl group.

Examples of the monocyclic or polycyclic heterocyclic group are those of 3 to 25 ring carbon atoms, such as pyridyl, furyl, thienyl, pyranyl, pyrrolyl, thianthrenyl, pyrazolyl, isothiazolyl, isoxazolyl, pyrazinyl, pyrimidinyl, pyridazinyl, tetrahydropyranyl, tetrahydrofuranyl, tetrahydrothiopyranyl, tetrahydrothiofuranyl and 3-tetrahydrothiophene-1,1-dioxide. One hydrogen atom or two or more hydrogen atoms on the ring atoms of the above heterocyclic group may be substituted with an alkyl group, an alicyclic hydrocarbon group, an aryl group or a heterocyclic group. Among others, preferred are those having a monocyclic or polycyclic ether ring or lactone ring as exemplified as follows.

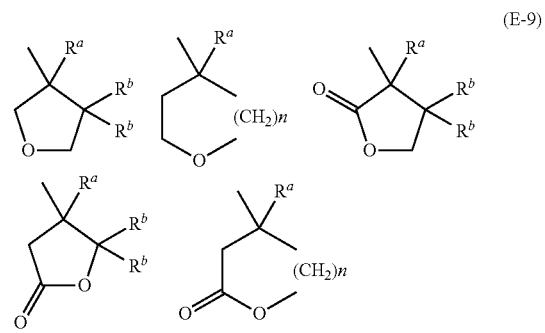

(E-9)

In the above formulas, $R^a$ and $R^b$ each independently represents a hydrogen atom or a $C_1$-$C_4$ alkyl group; and n represents an integer of 2 to 4.

The divalent alicyclic hydrocarbon group as the cyclic group B in the linking group W' can be monocyclic or polycyclic. Examples of the alicyclic hydrocarbon group are those having a monocyclo, bicyclo, tricycle or tetracyclo structure of 3 or more carbon atoms, preferably 3 to 30 carbon atoms, more preferably 3 to 25 carbon atoms. The alicyclic hydrocarbon group may have a substituent.

As the monocyclic hydrocarbon group, there can preferably be used those having 3 to 12 ring carbon atoms, more preferably 3 to 7 ring carbon atoms. Examples of the monocyclic hydrocarbon group are cyclopropylene, cyclobutylene, cyclopentylene, cyclohexylene, cycloheptylene, cyclooctylene, cyclodecanylene, cyclododecanylene, and 4-tert-butylcyclohexylene. As the polycyclic hydrocarbon group, there can preferably be used those having 7 to 15 ring carbon atoms. Examples of the polycyclic hydrocarbon group are adamantylene, noradamantylene, divalent decalin residue, tricyclodecanylene, tetracyclododecanylene, norbornylene and divalent cedrol residue. The alicyclic hydrocarbon group can be a spiro ring of preferably 3 to 6 carbon atoms. One hydrogen atom or two or more hydrogen atoms on the ring carbons of the above organic group, or one hydrogen atom or two or more hydrogen atoms of the above linking group, may be each independently substituted with a substituent such as a $C_1$-$C_{30}$ alkyl or substituted alkyl group, a hydroxy group, an alkoxy group, a carboxyl group or an alkoxycarbonyl group as explained above for $R^{10}$, $R^{11}$. One hydrogen atom or two or more hydrogen atoms of the substituent may also be further substituted with fluorine or trifluoromethyl.

Examples of the divalent aromatic hydrocarbon group are those of 1 to 30 carbon atoms. It is preferable that, when the divalent aromatic hydrocarbon group is monocyclic, the monocyclic divalent aromatic hydrocarbon group has 3 to 12 ring carbon atoms, more preferably 3 to 6 ring carbon atoms. As such an aromatic hydrocarbon group, there can be used divalent groups obtained by elimination of two hydrogen atoms from benzene, biphenyl, terphenyl, toluene, phenol, anisole, mesitylene, cumene, 2,3-xylylene, 2,4-xylylene, 2,5-xylylene, 2,6-xylylene, 3,4-xylylene, 3,5-xylylene, fluorobenzene, trifluoromethylbenzene, o-bistrifluoromethylphenyl, m-bistrifluoromethylphenyl, p-bistrifluoromethylphenyl, chlorobenzene, p-bromobenzene and p-iodobenzene.

Examples of the substituted or unsubstituted condensed polycyclic aromatic group as the linking group W' are those of 1 to 30 carbon atoms, such as divalent organic groups obtained by elimination of two hydrogen atoms from pentalene, indene, naphthalene, azulene, heptalene, biphenylene, indacene, acenaphthylene, fluorene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene and the like. One hydrogen atom or two or more hydrogen atoms of the above condensed polycyclic aromatic group may be substituted with a fluorine atom or a $C_1$-$C_4$ alkyl or fluorine-containing alkyl group.

Examples the monocyclic or polycyclic heterocyclic group as the linking group W' are those of 3 to 25 ring carbon atoms, such as divalent organic groups obtained by elimination of two hydrogen atoms from pyridine, furan, thienin, pyranine, pyrroline, thianthrene, pyrazon, isothiazone, isooxazoline, pyrazine, pyrimidine, pyridazine, tetrahydropyranine, tetrahydrofuranin, tetrahydrothiopyranine, tetrahydrothiofuranin and the like. One hydrogen atom or two or more hydrogen atoms on the ring atoms of the above heterocyclic group may be substituted with an alkyl group (preferably, lower alkyl group), an alicyclic hydrocarbon group, an aryl group or a heterocyclic group. Among others, preferred are those having a monocyclic or polycyclic ether ring or lactone ring as exemplified as follows.

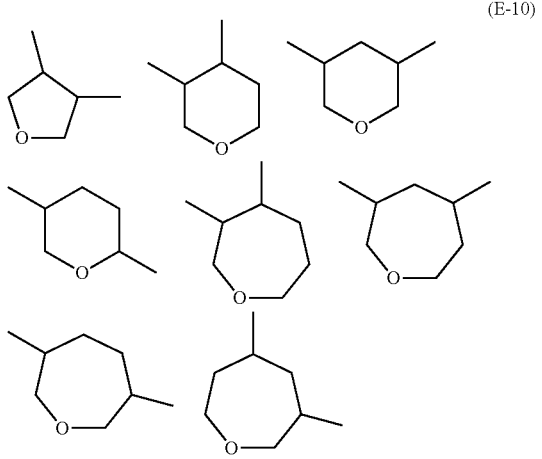

(E-10)

As mentioned above, the linking group W' may be a divalent group formed by combination of any of the divalent groups explained by the general formulas and exemplified above.

Preferred examples of the linking group W' are: — (single bond); —$CH_2$—; —$(CH_2)_2$—; —$(CH_2)_3$—; —$(CH(CH_3)CH_2)$—; —$(CH_2)_3$—; —B—$CH_2$—; —$C_6H_4$—; —O—$C_6H_4$—; —$CH_2$—O—$CH_2$—; —$CH_2$—C(=O)—O—$CH_2$—; —B—; —B—C(=O)—O—$CH_2$—; —$CH_2$—C(=O)—O—B—; —$CR^{10}R^{11}$—; —$(CR^{10}R^{11})_2$—; —O—$(CR^{10}R^{11}$—$C_6H_4)_2$—; and —O—$CR^{10}R^{11}$—$C_6H_4$— (where B is the above-mentioned cyclic group).

A linking group of the following formula is preferred as the linking group $W^1$. It is herein noted that $R^X$ and $R^Y$ inside the parentheses are used to indicate bonding directions for reference purposes and are not included in $W^1$.

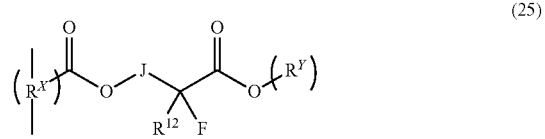

(25)

In the general formula (25), $R^{12}$ represents a hydrogen atom, a fluorine atom or a fluorine-containing alkyl group. There is no particular limitation on the fluorine-containing alkyl group. Examples of the fluorine-containing alkyl group are those of 1 to 12 carbon atoms, preferably 1 to 3 carbon atoms, such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoroisopropyl. Among others, fluorine or trifluoromethyl is preferred as $R^{12}$. Further, J represents a divalent organic group. Preferred examples of the divalent organic group are the same as the above-explained substituted methylene group —$(CR^{10}R^{11})_m$— (m is an integer of 1 to 10) as indicated below.

In the respective formulas, oxygen and carbon atoms adjacent to the substituted methylene group are indicated by O and C.

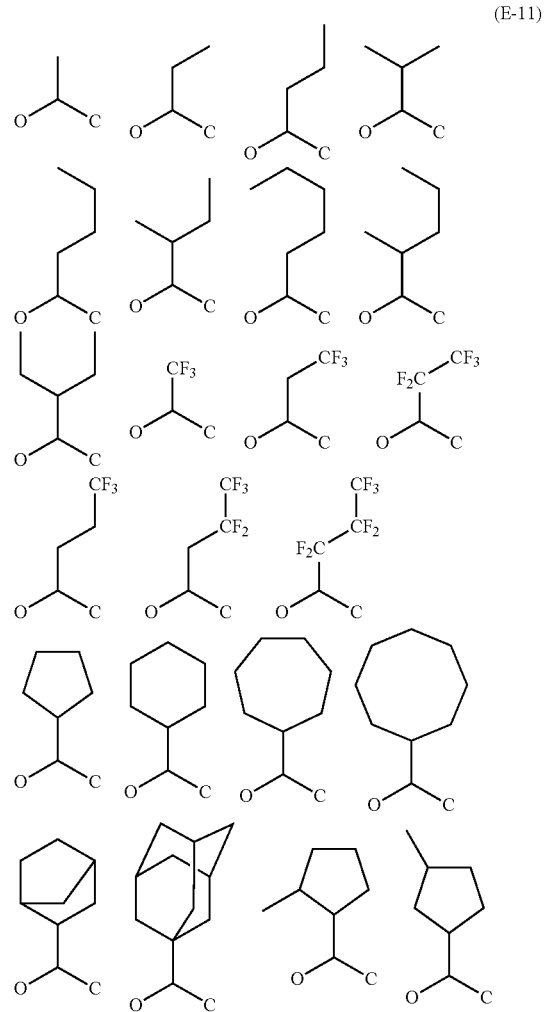

(E-11)

-continued

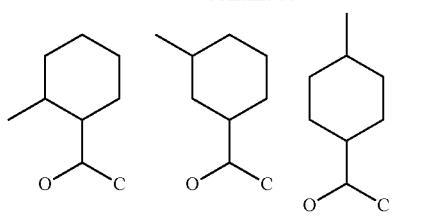

(E-12)

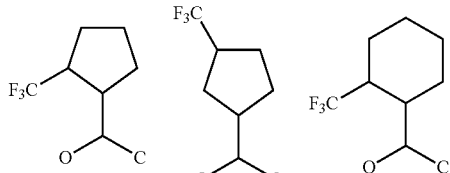

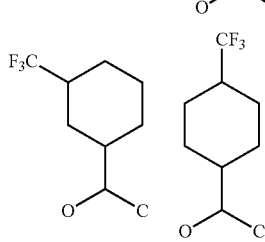

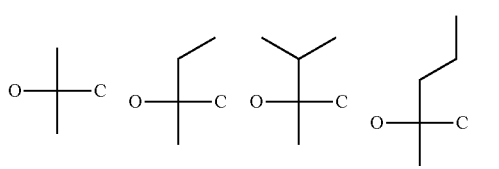

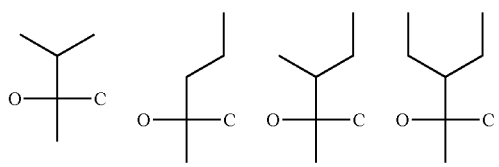

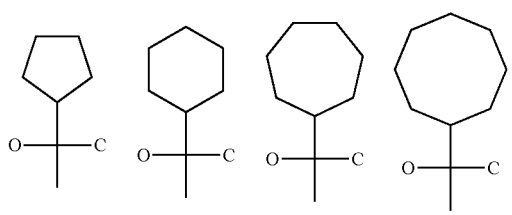

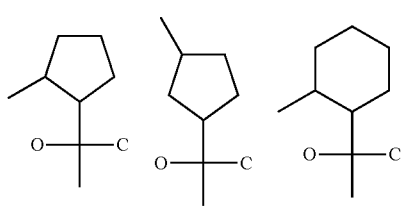

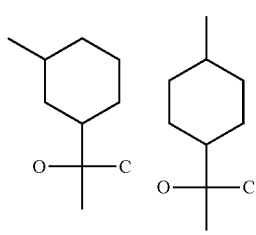

-continued (E-13)

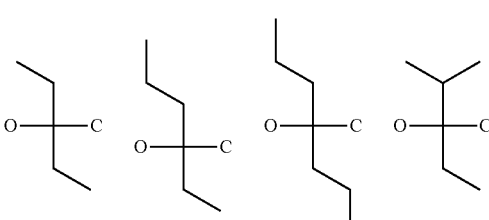

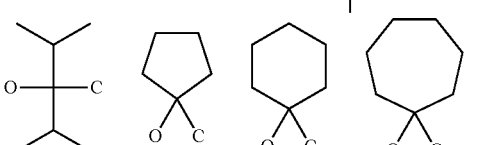

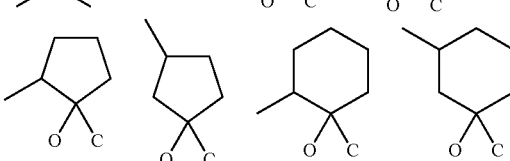

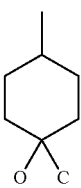

<Repeating Unit (A)>

In the repeating unit (A) of the general formula (24-1), the acid labile group $R^{9-1}$ is preferably either one of organic groups of the following general formulas (d) to (h).

$$R^{13}-O-C(=O)- \quad (d)$$

$$R^{13}-O-CHR^{14}- \quad (e)$$

$$CR^{15}R^{16}R^{17}- \quad (f)$$

$$SiR^{15}R^{16}R^{17}- \quad (g)$$

$$R^{13}-C(=O)- \quad (h)$$

In the above formulas, $R^{13}$, $R^{14}$, $R^{15}$, $R^{16}$ and $R^{17}$ represent monovalent organic groups as explained below. Among the organic groups of the general formulas (d) to (h), it is preferable to use the organic group of the general formula (d), (e) or (f) in the resist composition for pattern formation by exposure to high-energy radiation of 300 nm or less wavelength because each of the organic groups of the general formulas (d), (e) and (f) has the chemical amplification function of eliminating the acid labile group eliminates by the action of an acid ($H^+$) generated from the photoacid generator by light irradiation and, at the same time, regenerating the acid.

$R^{13}$ represents an alkyl group, an alicyclic hydrocarbon group or an aryl group. $R^{14}$ represents a hydrogen atom, an alkyl group, an alicyclic hydrocarbon group, an alkenyl group, an aralkyl group, an alkoxy group or an aryl group. $R^{15}$, $R^{16}$ and $R^{17}$ can be the same or different and each represents an alkyl group, an alicyclic hydrocarbon group, an alkenyl group, an aralkyl group or an aryl group. The above-mentioned group $R^{15}$, $R^{16}$ and $R^{17}$ may have a substituent. Two of $R^{15}$, $R^{16}$ and $R^{17}$ may be bonded to each other to form a ring.

Preferred examples of the alkyl group are those of 1 to 4 carbon atoms, such as methyl, ethyl, propyl, isopropyl, n-butyl, sec-butyl and tert-butyl. Preferred examples of the alicyclic hydrocarbon group are those of 3 to 30 carbon atoms, such as cyclopropyl, cyclopentyl, cyclohexyl, adamantyl, norbornyl, bornyl, tricyclodecanyl, dicyclopentenyl, norbornane-epoxy, menthyl, isomenthyl, neomenthyl, tetracyclododecanyl and steroid residue. Preferred examples of the alkenyl group are those of 2 to 4 carbon atoms, such as vinyl, propenyl, allyl and butenyl. Preferred examples of the aryl group are those of 6 to 14 carbon atoms, such as phenyl, xylyl, tolyl, cumenyl, naphthyl and anthracenyl. These groups may have substituents. Preferred examples of the aralkyl group are those of 7 to 20 carbon atoms, such as benzyl, phenethyl and cumyl, each of which may have a substituent.

As the substituents of the above organic groups, there can be used: a hydroxy group; a halogen atom (preferably, fluorine); a nitro group; a cyano group; any of the above alkyl and alicyclic hydrocarbon groups; an alkoxy group such as methoxy, ethoxy, hydroxyethoxy, propoxy, hydroxypropoxy, n-butoxy, isobutoxy, sec-butoxy or tert-butoxy; an alkoxycarbonyl group such as methoxycarbonyl or ethoxycarbonyl; an aralkyl group such as benzyl, phenethyl or cumyl; an aralkyloxy group; an acyl group such as formyl, acetyl, butyryl, benzoyl, cinnamyl or valeryl; an acyloxy group such as butyryloxy; any of the above alkenyl groups; an alkenyloxy group such as vinyloxy, propenyloxy, allyloxy or butenyloxy; any of the above aryl groups, an aryloxy group such as phenoxy; and an aryloxycarbonyl group such as benzoyloxy.

There can also be used lactone groups of the following formulas (E-14) and (E-15).

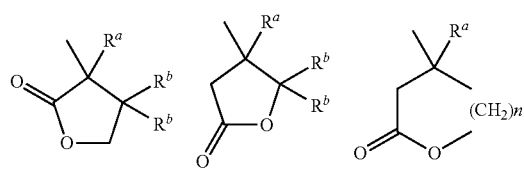

(E-14)

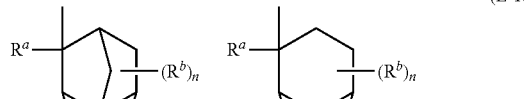

(E-15)

In the above formulas, $R^a$ represents a $C_1$-$C_4$ alkyl or perfluoroalkyl group; $R^b$ each independently represent a hydrogen atom, a $C_1$-$C_4$ alkyl or perfluoroalkyl group, a hydroxy group, a carbonic acid group, an alkyloxycarbonyl group or an alkoxy group; and n represents an integer of 1 to 4.

As mentioned above, it is preferable to use the acid labile group of the general formula (d), (e) or (f) in the resist composition for pattern formation by exposure to high-energy radiation such as laser radiation or electron beam radiation because each of the acid labile groups of the general formulas (d), (e) and (f) has the chemical amplification function.

The acid labile group is more specifically exemplified as follows.

Specific examples of the alkoxycarbonyl group represented by the general formula (d): $R^{13}$—O—C(=O)— are tert-butoxycarbonyl, tert-amyloxycarbonyl, methoxycarbonyl, ethoxycarbonyl, i-propoxycarbonyl, cyclohexyloxycarbonyl, isobornyloxycarbonyl and adamantanoxycarbonyl.

Specific examples of the acetal group represented by the general formula (e): $R^{13}$—O—$CHR^{14}$— are methoxymethyl, ethoxymethyl, 1-ethoxyethyl, 1-butoxyethyl, 1-isobutoxyethyl, 1-cyclohexyloxyethyl, 1-benzyloxyethyl, 1-phenethyloxyethyl, 1-ethoxypropyl, 1-benzyloxypropyl, 1-phenethyloxypropyl, 1-ethoxybutyl, 1-cyclohexyoxyethyl, 1-ethoxyisobutyl, 1-methoxyethoxymethyl, tetrahydropyranyl and tetrahydrofuranyl. There can also be used acetal groups obtained by addition of vinyl ethers to a hydroxy group.

Specific examples of the tertiary hydrocarbon group represented by the general formula (f): $CR^{15}R^{16}R^{17}$— are tert-butyl, tert-amyl, 1,1-dimethylpropyl, 1-ethyl-1-methylpropyl, 1,1-dimethylbutyl, 1-ethyl-1-methylbutyl, 1,1-diethylpropyl, 1,1-dimethyl-1-phenylmethyl, 1-methyl-1-ethyl-1-phenylmethyl, 1,1-diethyl-1-phenylmethyl, 1-methylcyclohexyl, 1-ethylcyclohexyl, 1-methylcyclopentyl, 1-ethylcyclopentyl, 1-isobornyl, 1-methyladamantyl, 1-ethyladamantyl, 1-isopropyladamantyl, 1-isopropylnorbornyl and 1-isopropyl-(4-methylcyclohexyl).

The alicyclic hydrocarbon group or the alicyclic hydrocarbon-containing acid labile group can be exemplified by the following formulas (E-16) and (E-17).

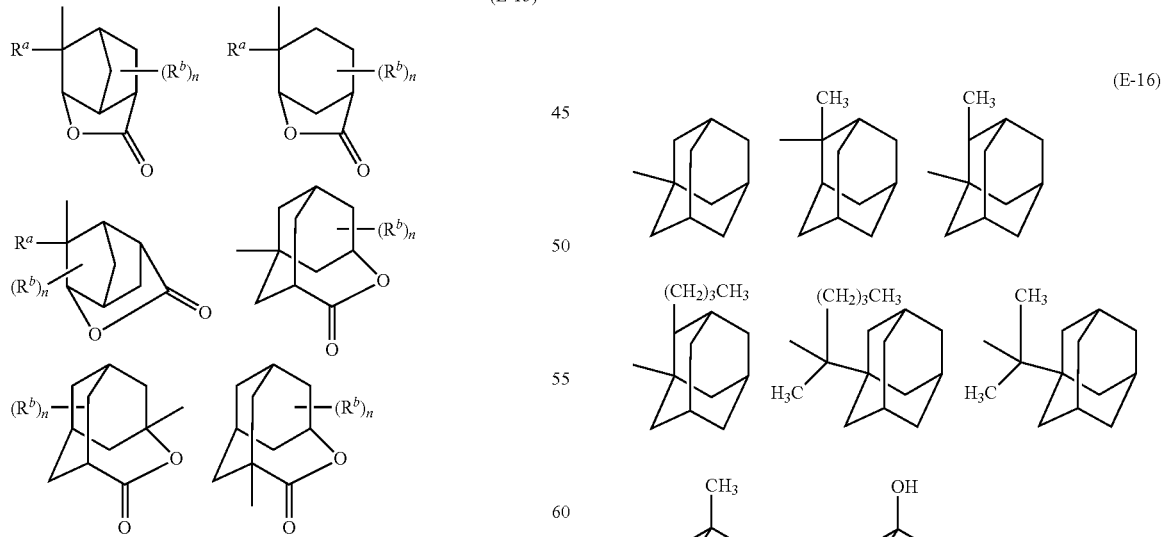

(E-16)

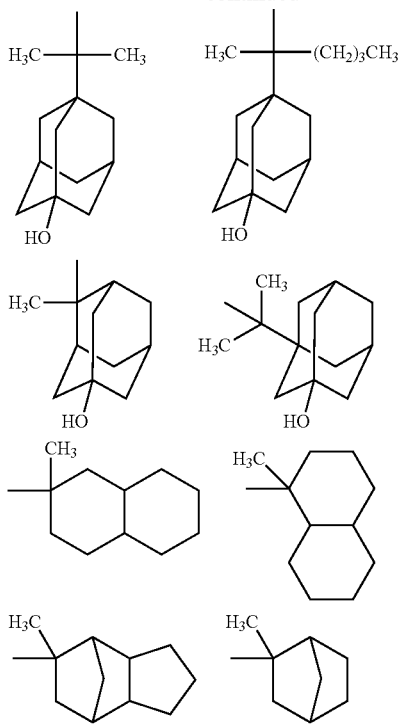
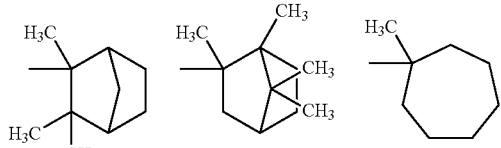
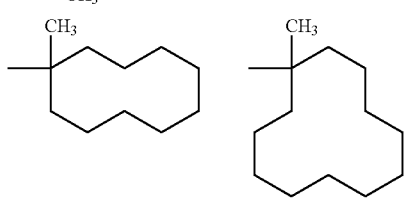

(E-17)

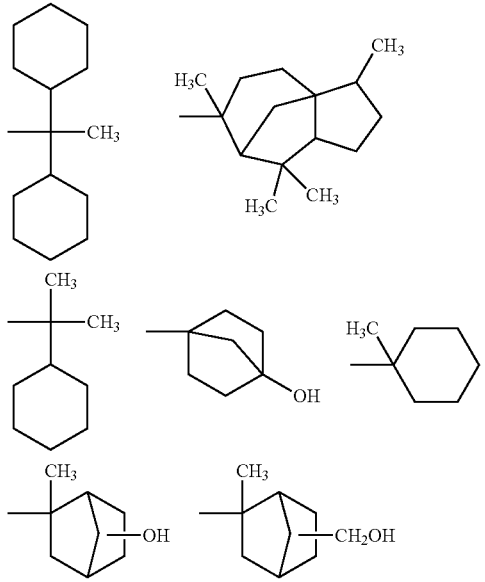

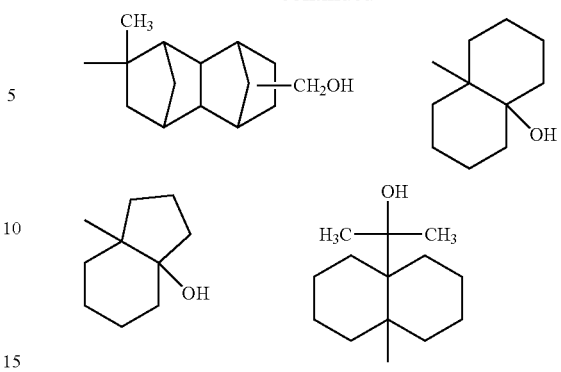

In the formulas (E-16) and (E-17), methyl ($CH_3$) group may independently be replaced by ethyl group; and one or two or more of ring carbons may have a substituent group as mentioned above.

Specific examples of the silyl group represented by the general formula (g): $SiR^{15}R^{16}R^{17}$— are trimethylsilyl, ethyldimethylsilyl, methyldiethylsilyl, triethylsilyl, i-propyldimethylsilyl, methyl-di-i-propylsilyl, tri-i-propylsilyl, tert-butyldimethylsilyl, methyl-di-tert-butylsilyl, tri-tert-butylsilyl, phenyldimethylsilyl, methyldiphenylsilyl and triphenylsilyl.

Specific examples of the acyl group represented by the general formula (h): $R^{13}$—C(=O)— are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydroatropoyl, atropoyl, cinnamoyl, furoyl, thenoyl, nicotinoyl and isonicotinoyl. There can also be used those obtained by substitution of a part or all of hydrogen atoms of the above acid labile groups with a fluorine atom.

Further, the lactone-containing acid-labile protecting group can be exemplified by the following formulas (E-18), (E-19) and (E-20).

(E-18)

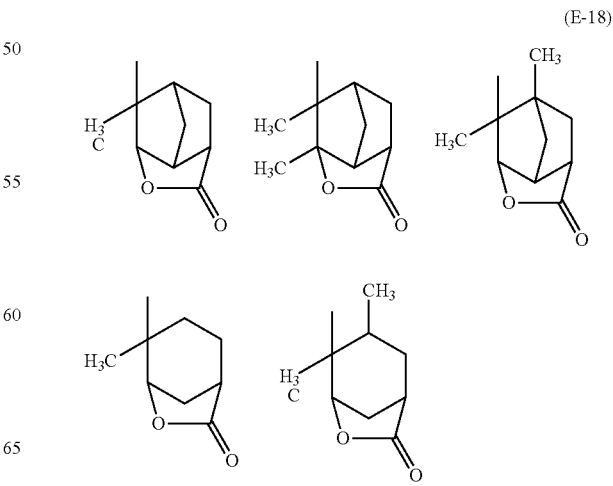

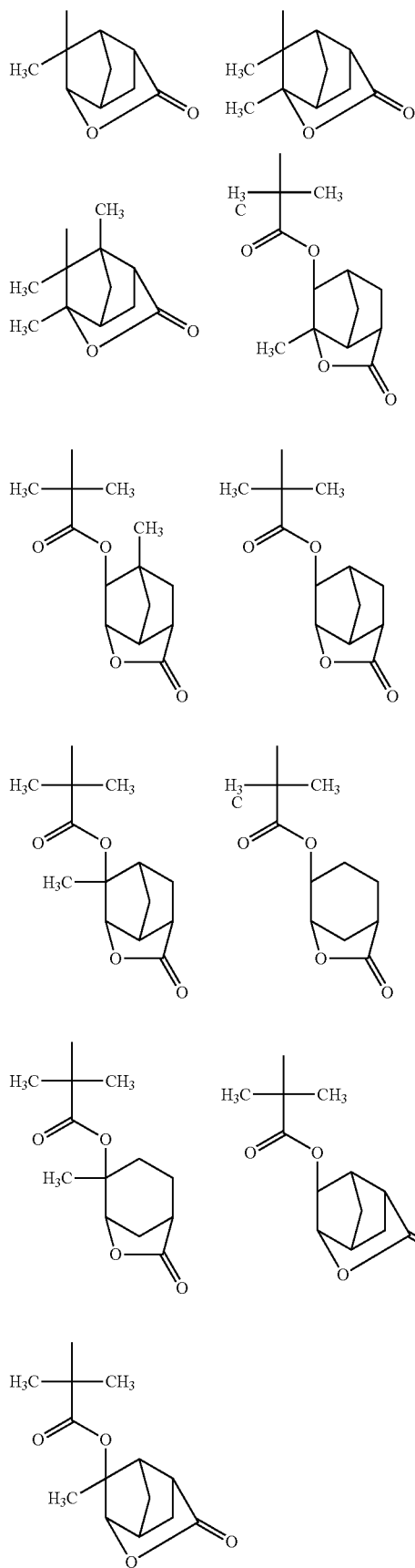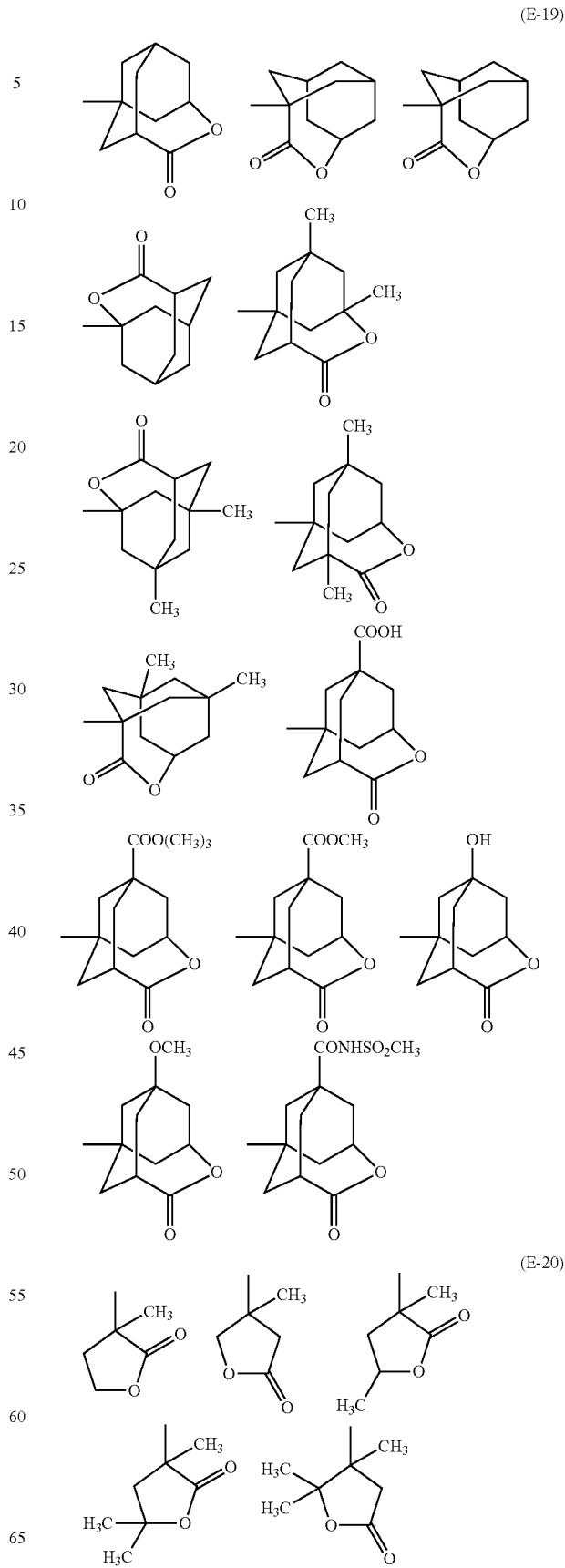

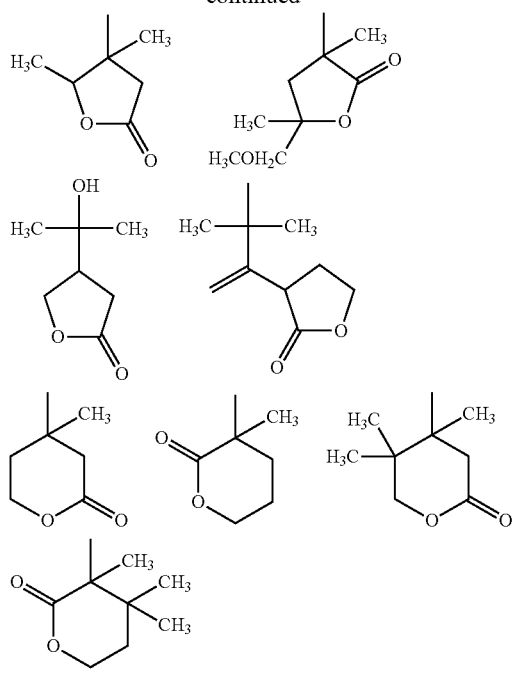

In the formulas (E-18), (E-19) and (E-20), methyl (CH$_3$) group may independently be replaced by ethyl group.

In the case of using the light source such as ArF excimer laser for exposure to high-energy radiation of 300 nm or less wavelength, the acid labile group is preferably a tertiary alkyl group such as tert-butyl or tert-amyl, an alkoxyethyl group such as 1-ethoxyethyl, 1-butoxyethyl, 1-isobutoxyethyl or 1-cyclohexyloxyethyl, an alkoxymethyl group such as methoxymethyl or ethoxymethyl, or an acid labile group having an alicyclic hydrocarbon structure such as adamantyl or isobornyl or a lactone structure as exemplified above.

Preferred examples of the acid labile group are those indicated below. In the respective formulas, the dotted lines each indicate a bonding position.

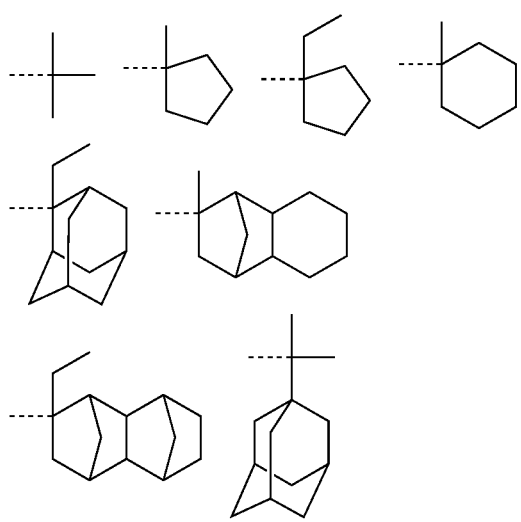

(E-21)

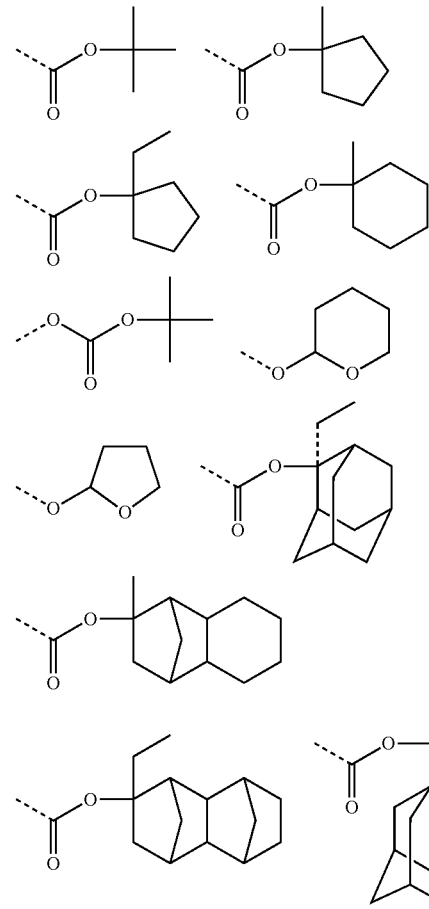

-continued

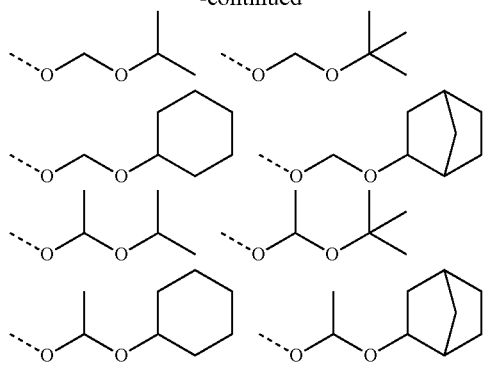

<Repeating Unit (B)>

The neutral hydroxyl group (also called "alcoholic hydroxyl group") is substantially neutral and, when introduced into the base resin, does not function to improve the solubility of the resin in an aqueous alkaline solution but functions to form cross-linking such as ester bond, ether bond or ureide bond through hydroxyl reaction with a cross-linking agent and thereby change the resin from soluble to insoluble or difficult-to-dissolve in an aqueous alkaline solution.

The neutral hydroxyl group is introduced into the base resin in order to exhibit negative photosensitivity by cross-linking of the neutral hydroxyl group, that is, the difficulty of the resist to be dissolved in an aqueous alkali solution after exposure to high-energy radiation of 300 nm or less wavelength. The polarity of the polymer terminal end can be changed and controlled by varying the kind of the neutral hydroxyl group and the ratio of the neutral hydroxyl group to the stable group (i.e. the group having no neutral hydroxyl group on a terminal end thereof) so as to achieve suitable solvent solubility, substrate applicability, surface tension, acid generator distribution, acid diffusion rate etc.

In the repeating unit (B) of the general formula (24-2), the neutral hydroxyl group $R^{9-2}$ is represented by the general formula (26).

In the general formula (26), $W^2$ is an alicyclic hydrocarbon group, an aliphatic hydrocarbon group or an organic group of valency h+1 formed by combination of alicyclic and aliphatic hydrocarbon groups; and h is an integer of 1 to 3.

The alicyclic hydrocarbon group as $W^2$ can be monocyclic or polycyclic. Preferably, the alicyclic hydrocarbon group is polycyclic, saturated and of 5 to 15 carbon atoms.

The aliphatic hydrocarbon group is a group obtained by elimination of h+1 hydrogen atoms from a branched or unbranched saturated hydrocarbon group where h is preferably 1. More specifically, the aliphatic hydrocarbon group is an organic group of 1 to 10 carbon atoms, preferably 1 to 8 carbon atoms. Among others, particularly preferred is an ethylene or methylene group.

There can also be used a halogenated alkylene group obtained by substitution of a part or all of hydrogen atoms of the aliphatic hydrocarbon group of 1 to 4 carbon atoms (preferably, ethylene group or methylene group) with a halogen atom. Preferred are those substituted with a fluorine atom.

$R^{9-2}$ can be selected from the above range depending on the purpose of control of the characteristics of the resist composition using the fluorine-containing polymer compound. For example, the neutral hydroxyl group of the general formula (26) is preferably a group of the general formula (27) in order to obtain a wide exposure margin during line pattern formation by underexposure.

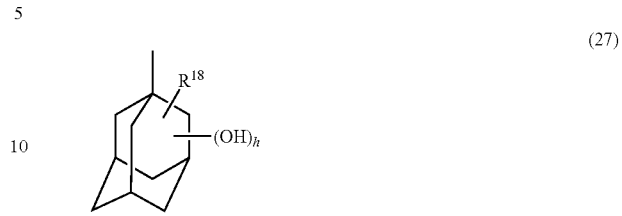

In the general formula (27), $R^{18}$ represents a hydrogen atom, an alkyl group or an alkoxyl group of 1 to 5 carbon atoms; and h represents an integer of 1 to 3.

Examples of the alkyl group as $R^{18}$ are those of 1 to 5 carbon atoms, such as methyl, ethyl, propyl, isopropyl, n-butyl, isobutyl, tert-butyl, pentyl, isopentyl and neopentyl. Among others, lower alkyl is preferred. Particularly preferred is methyl.

Examples of the alkoxyl group as $R^{18}$ are residue groups obtained by bonding an oxygen atom to the above alkyl groups and having a straight or branched chain structure of 1 to 5 carbon atoms, preferably 1 to 3 carbon atoms. As mentioned above, h is an integer of 1 to 3. It is preferable that h is 1. Although the bonding position of the hydroxyl group is not particularly limited, the hydroxyl group is preferably bonded to 3-position of adamantyl group.

The following are preferred examples of the neutral hydroxyl-containing alicyclic group other than the monovalent organic group of the general formula (8). The neutral hydroxyl-containing group is not however limited to these examples.

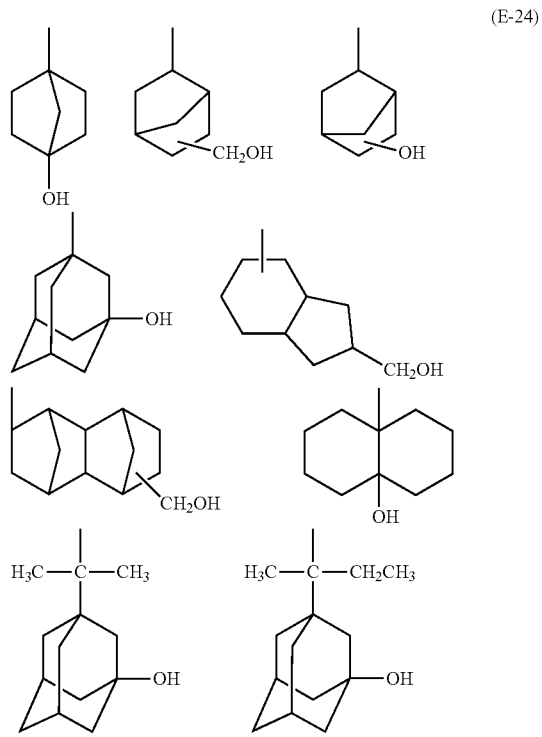

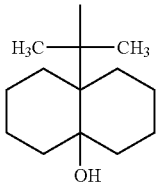

Further, hydroxymethyl, 2-hydroxyethyl, 3-hydroxypropyl, 4-hydroxybutyl, 5-hydroxypentyl and 2,2-dimethyl-3-hydroxypropyl are other examples of the neutral hydroxyl-containing group.

<Repeating Unit (C)>

Examples of the repeating unit (C) are, but not limited to, those formed by cleavage of polymerizable double bonds of the following monomers. The performance required of the resin, notably, (1) the solubility in a resist solvent; (2) the film forming property (glass transition temperature); (3) the alkali developability; (4) the film thickness reduction (hydrophilicity/hydrophobicity, alkali-soluble group selection); (5) the adhesion of an unexposed portion to a substrate; and (6) the dry etching resistance, can be controlled by the addition of the repeating unit (C).

In the repeating unit (C) of the general formula (24-3), $R^{9\text{-}3}$ is a group other than the acid labile group and the neutral hydroxyl-containing group as mentioned above.

The following explanation will be given to the form of a corresponding monomer before conversion to the repeating unit (C) by cleavage of the polymerizable double bond.

Examples of the monomer corresponding to the repeating unit (C) are maleic anhydrides, acrylic esters, methacrylic esters, fluorine-containing acrylic esters, fluorine-containing methacrylic esters, styrenic compounds, fluorine-containing styrenic compounds, vinyl ethers, fluorine-containing vinyl ethers, allyl ethers, fluorine-containing allyl ethers, acrylamides, methacrylamides, vinyl esters, allyl esters, olefins, fluorine-containing olefins, norbornene compounds, fluorine-containing norbornene compounds, sulfur dioxide and vinyl silanes. Any of these monomer can be copolymerized with a monomer corresponding to the repeating unit (A) or (B). Among others, acrylic esters, methacrylic esters, fluorine-containing acrylic esters, fluorine-containing methacrylic esters, norbornene compounds, fluorine-containing norbornene compounds, styrenic compounds, vinyl ethers and fluorine-containing vinyl ethers are preferred.

There is no particular limitation on the ester moiety of the acrylic ester or methacrylic ester. Specific examples of the acrylic esters or methacrylic esters are known acrylic or methacrylic ester compounds: such as acrylic or methacrylic acid alkyl ester e.g. methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, tert-butyl acrylate or methacrylate, amyl acrylate or methacrylate, n-hexyl acrylate or methacrylate, n-octyl acrylate or methacrylate, 2-ethylhexyl acrylate or methacrylate, benzyl acrylate or methacrylate, chlorbenzyl acrylate or methacrylate, octyl acrylate or methacrylate, 2-hydroxyethyl acrylate or methacrylate, 4-hydroxybutyl acrylate or methacrylate, 5-hydroxypentyl acrylate or methacrylate, 2,2-dimethyl-3-hydroxypropyl acrylate or methacrylate, trimethylolpropane monoacrylate or methacrylate, pentaerythritol monoacrylate or methacrylate, furfuryl acrylate or methacrylate, tetrahydrofuryl acrylate or methacrylate, lauryl acrylate or methacrylate, 2-hydroxyethyl acrylate or methacrylate, or 2-hydroxypropyl acrylate or methacrylate; acrylate or methacrylate containing an ethylene glycol group, propylene glycol group or tetramethylene glycol group; alkoxysilyl-containing acrylic or methacrylic ester; t-butyl acrylate or methacrylate; 3-oxocyclohexyl acrylate or methacrylate; adamantyl acrylate or methacrylate; alkyl (methyl, ethyl or hydroxy) adamantyl acrylate or methacrylate; cyclohexyl acrylate or methacrylate; tricyclodecanyl acrylate or methacrylate; and acrylate or methacrylate having a ring structure such as norbornene ring. There can also be used acrylate compounds having the same ester moieties as above and containing a trifluoromethyl group or cyano group in α-moieties thereof.

Examples of the fluorine-containing acrylic esters or fluorine-containing methacrylic esters are: acrylic or methacrylic ester monomers each having a fluorine atom or a fluorine-containing group at α-position of the acrylic acid group; and acrylic or methacrylic ester monomers having a fluorine-containing group in ester moieties thereof. As the acrylic or methacrylic ester monomers having a fluorine-containing alkyl group at α-position, for example, there can suitably be used those obtained by addition of a trifluoromethyl group, a trifluoroethyl group, a nonafluoro-n-butyl group etc. to the α-position of the above non-fluorinated acrylic ester or methacrylic ester.

As the acrylic or methacrylic ester monomers having a fluorine-containing ester moiety, there can suitably be used those each having a perfluoroalkyl group, a fluoroalkyl group or a fluorine-containing cyclic group in which a fluorine atom or trifluoromethyl group is substituted on a ring structure such as a fluorine-containing benzene ring, a fluorine-containing cyclopentane ring, a fluorine-containing cyclohexane ring or a fluorine-containing cycloheptane ring, in the ester moiety and each of which may have a fluorine atom or fluorine-containing alkyl group at α-position. Specific examples of such fluorine-containing acrylic or methacrylic ester monomers are 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate, perfluorocyclohexylmethyl methacrylate, 6-[3,3,3-trifluoro-2-hydroxy-2-(trifluoromethyl)propyl]bicyclo[2.2.1]heptyl-2-yl acrylate, 6-[3,3,3-trifluoro-2-hydroxy-2-(trifluoromethyl)propyl]bicyclo[2.2.1]heytyl-2-yl 2-(trifluoromethyl)acrylate, 6-[3,3,3-trifluoro-2-hydroxy-2-(trifluoromethyl)propyl]bicyclo[2.2.1]heptyl-2-yl methacrylate, 1,4-bis(1,1,1,3,3,3-hexafluoro-2-hydroxyisopropyl)cyclohexyl acrylate, 1,4-bis(1,1,1,3,3,3-hexafluoro-2-hydroxyisopropyl)cyclohexyl methacrylate and 1,4-bis(1,1,1,3,3,3-hexafluoro-2-hydroxyisopropyl)cyclohexyl 2-trifluoromethyl acrylate.

Esters of acrylic acid, methacrylic acid and α,α,α-trifluoroacrylic acid (α,α,α-trilfuoromethacrylic acid), each of which has an α-fluorocarboxylate structure of the following structure, can also be used.

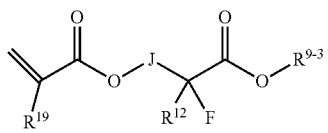
(28)

In the general formula (28), $R^{19}$ represents a hydrogen atom, a halogen atom or a $C_1$-$C_3$ alkyl or fluorine-containing alkyl group. Examples of the halogen atom as $R^{19}$ are fluorine, chlorine and bromine. Examples of the $C_1$-$C_3$ alkyl group as $R^{19}$ are methyl, ethyl, propyl and isopropyl. Examples of the $C_1$-$C_3$ fluorine-containing alkyl group as $R^{19}$ are those obtained by substitution of a part or all of fluorine atoms of the above alkyl group, such as trifluoromethyl; —$CF_3$, trifluoroethyl; —$CH_2CF_3$, 1,1,1,3,3,3-hexafluoroisopropyl and heptafluoroisopropyl. Among others, preferred are a hydrogen atom, a fluorine atom, a methyl group and a trifluoromethyl group. The linking groups J and $R^{12}$ have the same meanings as in the general formula (27). $R^{17}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an oxygen atom (ether bond) or a carbonyl group.

Examples of the substituted or unsubstituted $C_1$-$C_{25}$ aliphatic hydrocarbon group or substituted or unsubstituted $C_1$-$C_{25}$ aromatic hydrocarbon group are methyl, ethyl, propyl, isopropyl, cyclopropyl, n-propyl, sec-butyl, tert-butyl, n-pentyl, cyclopentyl, sec-pentyl, neopentyl, hexyl, cyclohexyl, ethylhexyl, norbornel, adamantyl, vinyl, allyl, butenyl, pentenyl, ethynyl, penyl, benzyl and 4-methoxybenzyl. A part or all of hydrogen atoms of the above groups may be substituted with fluorine.

In the repeating unit (C), $R^{9-3}$ is preferably a lactone-containing group, more preferably an ester of acrylic acid, methacrylic acid or α,α,α-trifluoroacrylic acid (α,α,α-trifluoromethacrylic acid). The lactone can be any lactone group having a lactone structure, preferably 5- to 7-membered lactone ring to which another ring may be fused to form a bicyclo or spiro structure. The use of such a lactone structure leads to good line edge roughness and less development failure. In this case, the amount of the repeating unit (C) derived from the lactone-containing monomer is preferably 10 to 60%, more preferably 20 to 50%, of all of the repeating units of the copolymer.

As the lactone group, there can be used those of the following formulas.

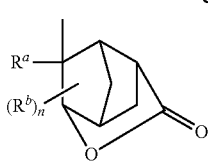
(E-25)

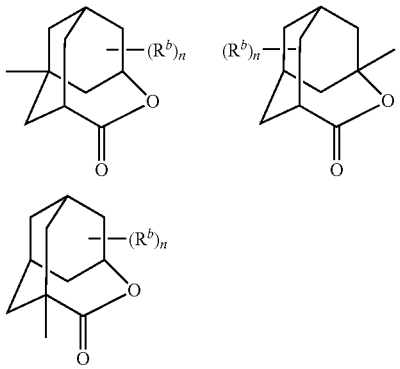
(E-26)

In the above formulas, $R^a$ represents a $C_1$-$C_4$ alkyl or perfluoroalkyl group; $R^b$ each independently represent a hydrogen atom, a $C_1$-$C_4$ alkyl or perfluoroalkyl group, a hydroxy group, a carbonic acid group, an alkyloxycarbonyl group or an alkoxy group; and n represents an integer of 1 to 4.

The following are specific examples of the lactone group.

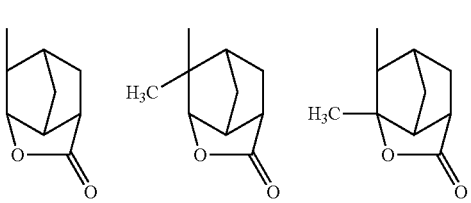
(E-27)

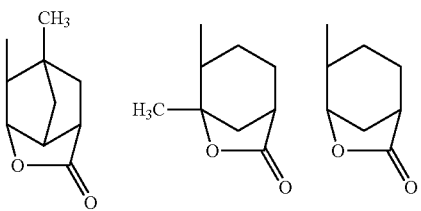

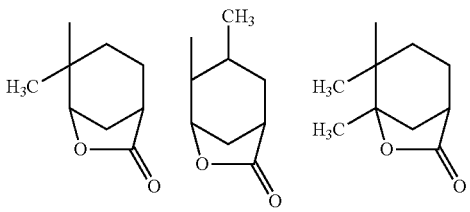

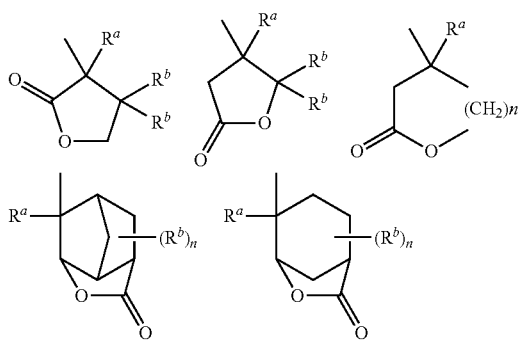

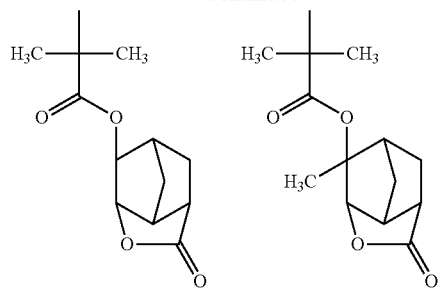
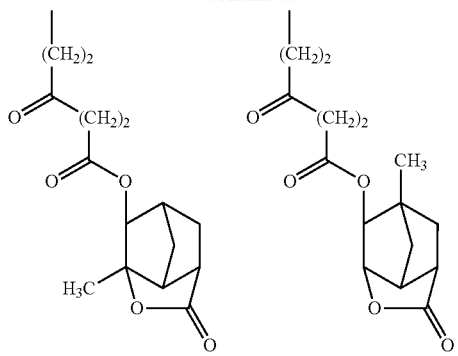
(E-28)
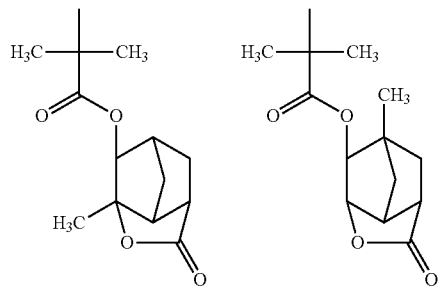
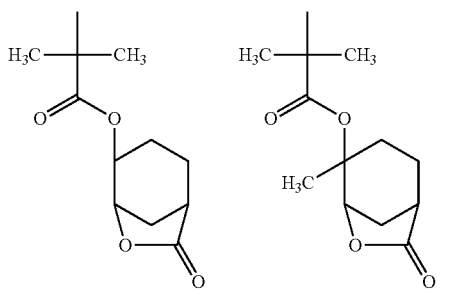
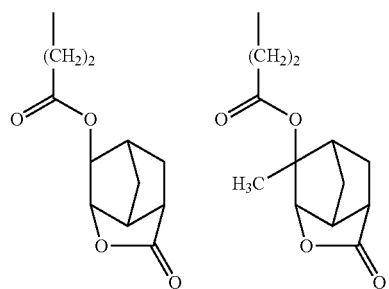
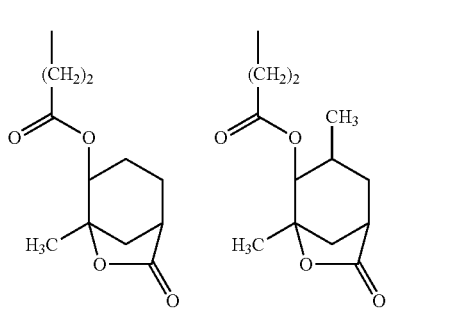
(E-29)
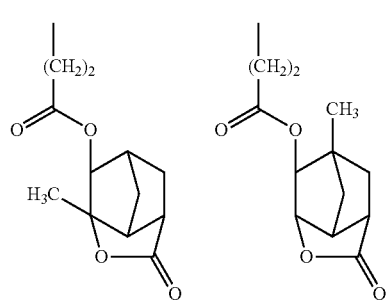
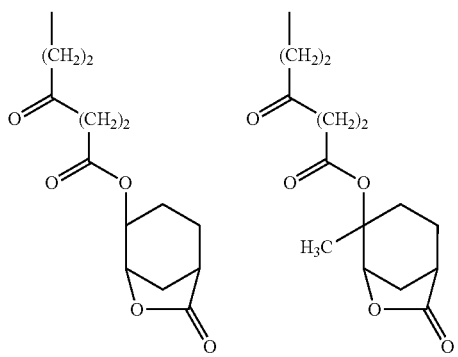
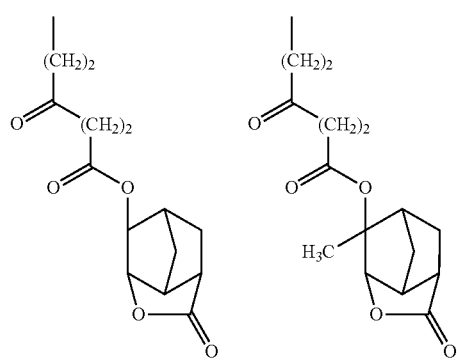
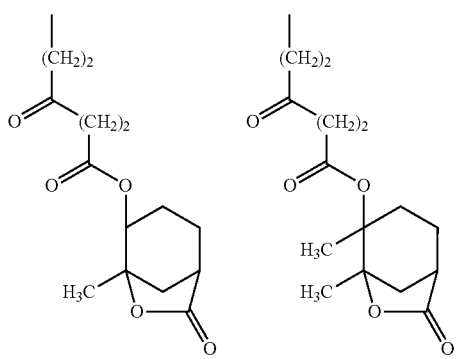

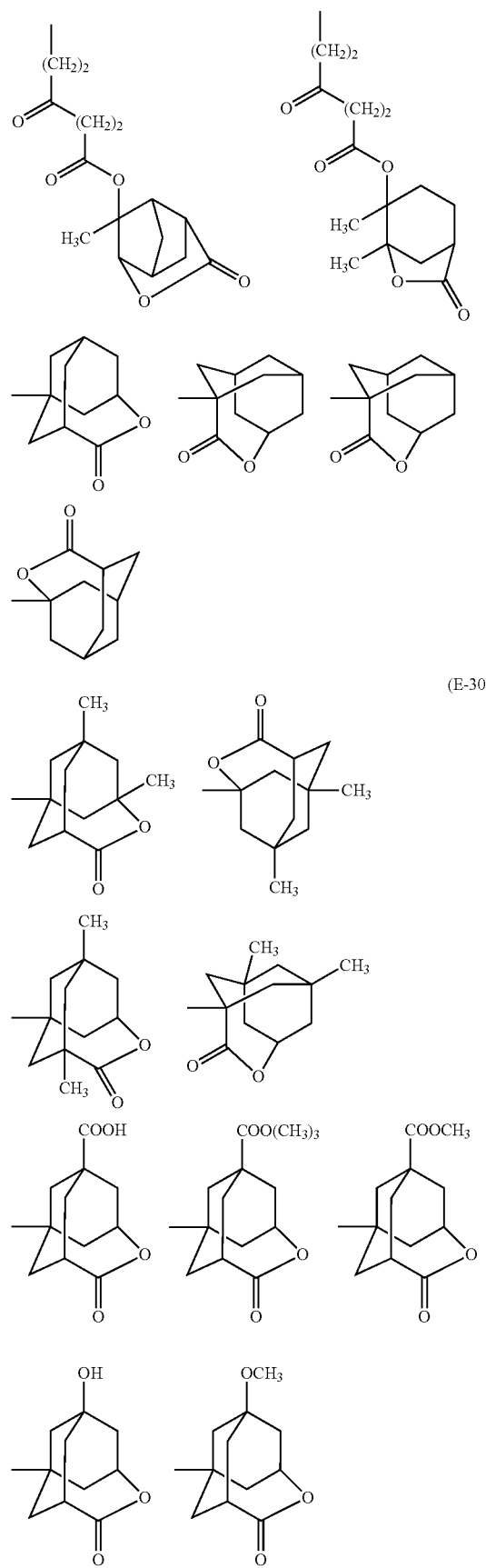
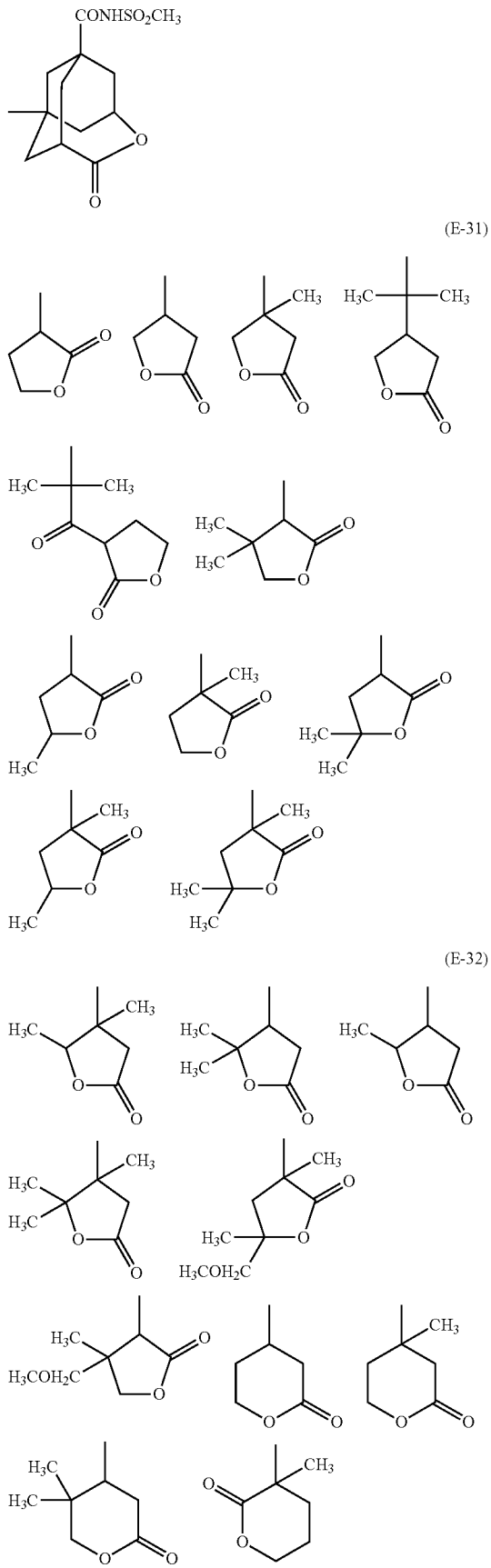

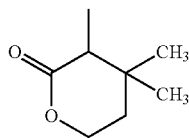

In the above formulas, methyl (CH$_3$) group may independently be replaced by ethyl group.

As the vinyl ethers or allyl ethers, there can be used those having a C$_1$-C$_{30}$ alkyl group, fluoroalkyl group or alicyclic hydrocarbon substituent group. These ether groups may also have a halogen atom (fluorine, chlorine, bromine), a hydroxyl group, an amino group, an aryl group, an alkyl group or an alicyclic hydrocarbon group as a substituent.

Specific examples of the alkyl vinyl ethers are methyl vinyl ether, ethyl vinyl ether, propyl vinyl ether, isopropyl vinyl ether, butyl vinyl ether, isobutyl vinyl ether, sec-butyl vinyl ether, tert-butyl vinyl ether, pentyl vinyl ether, hexyl vinyl ether, octyl vinyl ether, decyl vinyl ether, dodecyl vinyl ether, cyclopentyl vinyl ether, cyclohexyl vinyl ether, norbornel vinyl ether, adamantyl vinyl ether and butyllactone vinyl ether. Specific examples of the perfluoroalkyl vinyl ethers are perfluoromethyl vinyl ether, perfluoroethyl vinyl ether, perfluoropropyl vinyl ether, perfluoroisopropyl vinyl ether, perfluorobutyl vinyl ether, perfluoroisobutyl vinyl ether, perfluoro-sec-butyl vinyl ether, perfluoro-tert-butyl vinyl ether, perfluoropentyl vinyl ether, perfluorohexyl vinyl ether, perfluorooctyl vinyl ether and perfluorododecyl vinyl ether. Specific examples of the hydroxyl-containing vinyl ethers are hydroxymethyl vinyl ether, 2-hydroxyethyl vinyl ether, 3-hydroxypropyl vinyl ether, 4-hydroxybutyl vinyl ether, 5-hydroxypentyl vinyl ether, 6-hydroxyhexyl vinyl ether, diethylene glycol monovinyl ether, polyethylene glycol monovinyl ether and 1,4-cyclohexane dimethanol vinyl ether. Further, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, diethylene glycol vinyl ether, dimethylaminoethyl vinyl ether, diethylaminoethyl vinyl ether, butylaminoethyl vinyl ether, benzyl vinyl ether and tetrahydrofurfuryl vinyl ether are also specific examples of the vinyl ethers.

Specific examples of the allyl ethers are methyl allyl ether, ethyl allyl ether, propyl allyl ether, butyl allyl ether, benzyl allyl ether and cyclohexyl allyl ether. Specific examples of the hydroxyl-containing allyl ether are: alkylene glycol monoallyl ethers such as ethylene glycol monoallyl ether, propylene glycol monoallyl ether, diethylene glycol monoallyl ether, polyethylene glycol monoallyl ether and hydroxybutyl allyl ether; and allyl ethers of polyalcohols, such as glycerin monoallyl ether.

There can also be used: epoxy-containing vinyl or allyl ethers; β-ketoester-containing vinyl or allyl ethers such as allyl acetoacetate; and hydrolysable silicon-containing vinyl ethers such as trimethoxysilyl vinyl ether.

Specific examples of the allyl esters are allyl acetate, allyl caproate, allyl caprylate, allyl laurate, allyl palmitate, allyl stearate, allyl benzoate, allyl acetoacetate and allyl lactate.

Specific examples of the vinyl esters are vinyl butyrate, vinyl isobutyrate, vinyl trimethylacetate, vinyl diethylacetate, vinyl valerate, vinyl caproate, vinyl chloracetate, vinyl dichloracetate, vinyl methoxyacetate, vinyl butoxyacetate, vinyl acetoacetate, vinyl lactate, vinyl β-phenylbutyrate and vinyl cyclohexylcarboxylate.

There can also be used: dialkyl itaconate such as dimethyl itaconate, diethyl itaconate and dibutyl itaconate; dialkyl ester or monoalkyl ester of fumaric acid, such as dibutyl fumarate; and alkyl ester of vinylacetic acid, such as ethyl vinylacetate.

Specific examples of the olefins are ethylene, propylene and cyclohexene. Specific examples of the fluoroolefins are vinyl fluoride, vinylidene fluoride, trifluoroethylene, chlorotrifluoroethylene, tetrafluoroethylene, hexafluoropropylene, hexafluoroisobutene and octafluorocyclopentene.

Specific examples of the styrenic compounds are those in which a vinyl group is bonded to an aromatic ring, such as styrene, m- or p-methoxystyrene, m- or p-ethoxystyrene, m- or p-propoxystyrene, m- or p-isopropoxystyrene, m- or p-butoxystyrene, m- or p-tert-butoxystyrene, m- or p-(1-ethoxyethoxy)styrene, m- or p-(1-ethoxypropoxy)styrene, m- or p-(1-isobutoxyethoxy)styrene, m- or p-(2-tetrahydropyranyloxy)styrene, m- or p-tert-butoxycarbonyloxystyrene, m- or p-acetoxystyrene, m- or p-propionyloxystyrene, m- or p-pivaloyloxystyrene, m- or p-benzoyloxystyrene, m- or p-mesyloxystyrene, m- or p-phenylsulfonyloxystyrene, m- or p-tosyloxystyrene. A halogen atom, an alkyl group or a fluorine-containing alkyl group may be bonded to α-position of the above styrenic compounds.

In the present invention, it is feasible to introduce the styrenic compound structure into the fluorine-containing polymer by copolymerization of e.g. p-butoxycarbonyloxystyrene and conversion of the butoxycarbonyl moiety of the resulting copolymer to a hydroxyl group.

The norbornene compounds or fluorine-containing norbornene compounds can have a mononuclear structure or a multinuclear structure. Suitable examples of the norbornene compounds are those each formed by Diels-Alder addition reaction of an unsaturated compound such as a fluorine-containing olefin, allyl alcohol, fluorine-containing allyl alcohol, acrylic acid, α,α,α-trifluoroacrylic acid, methacrylic acid, vinyl ester, fluorine-containing vinyl ester, or any of the acrylic esters, methacrylic esters, fluorine-containing acrylic esters and fluorine-containing methacrylic esters mentioned above in the present specification with cyclopentadiene or cyclohexadiene.

Examples of the acrylamides or methacrylamides are unsaturated amides such as acrylamide, methacrylamide, N-alkyl acrylamide or methacrylamide (where the alkyl group is of 1 to 10 carbon atoms, such as methyl, ethyl, propyl, butyl, tert-butyl, heptyl, octyl, cyclohexyl, hydroxyethyl etc.), N-hydroxyethyl-N-methyl acrylamide or methacrylamide, N-methylol acrylamide, N-methylol methacrylamide and diacetone acrylamide.

Acrylic acid, methacrylic acid, vinylsulfonic acid, maleic acid, fumaric acid, crotonic acid, itaconic acid, maleimide, acrylonitrile, methacrylonitrile, maleilonitrile, alkoxysilyl-containing vinyl silane, allyloxyethanol and the like are also usable as the copolymerization monomer.

The repeating unit (C) is preferably a repeating unit formed by cleavage of a polymerizable double bond of at least one kind selected from the acrylic esters, fluorine-containing acrylic esters, methacrylic esters, fluorine-containing methacrylic esters, styrenic compounds and fluorine-containing styrenic compounds.

There is no particular limitation on the copolymerization monomer as long as it is copolymerizable. It is preferable that the copolymerization monomer does not have a multiple bond or aromatic ring for use by exposure to high-energy radiation or electron beam of 300 nm or less wavelength.

Further, it is preferable to use a polymerizable compound having a hexafluoroisopropyl hydroxyl group (CF$_3$C(CF$_3$)(OH)—) as the copolymerization monomer for introduction of the repeating unit (C) in order to increase the solubility of the base resin in a solvent. The following are specific examples of the polymerizable hexafluoroisopropyl hydroxyl-containing compound.

(E-33)

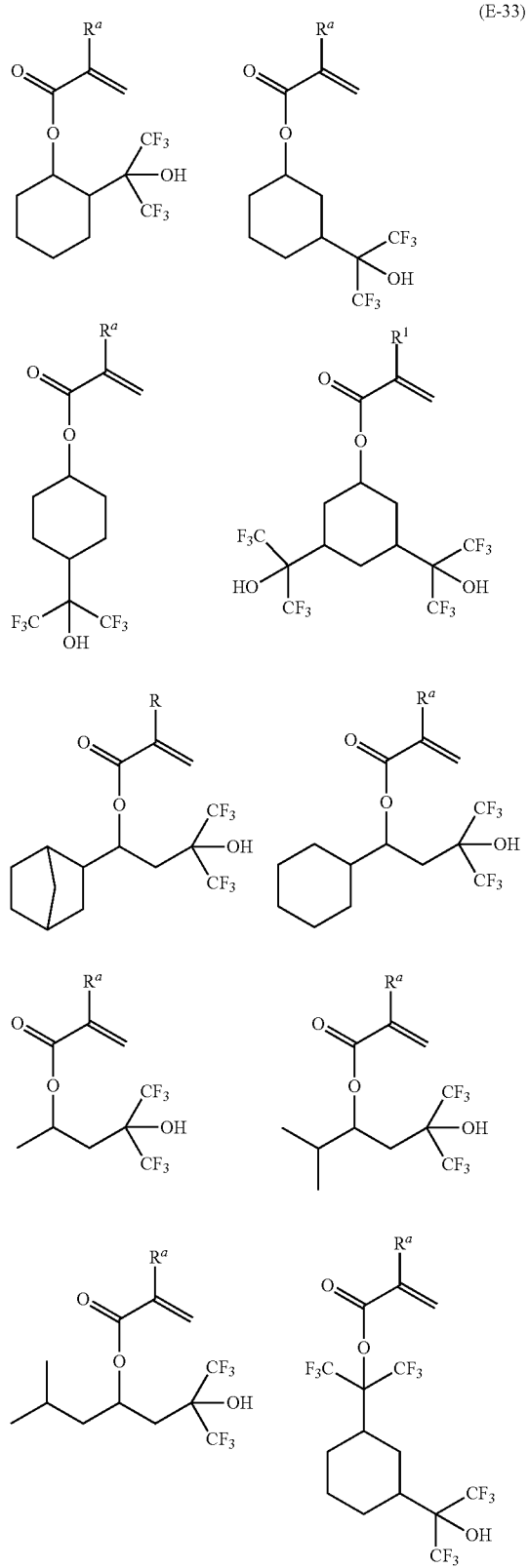

-continued

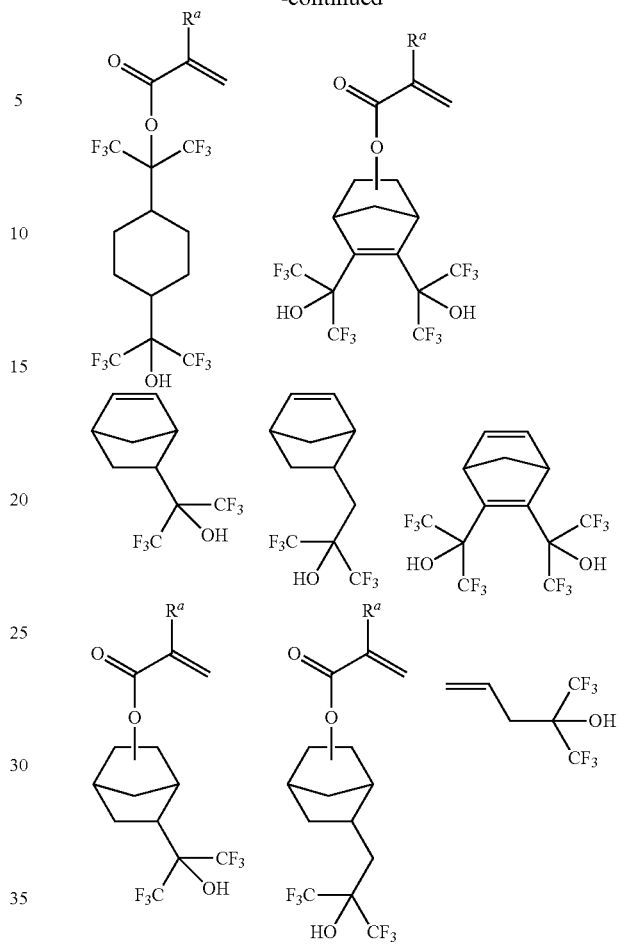

In the above formulas, $R^a$ represents a hydrogen atom, a methyl group, a fluorine atom or a trifluoromethyl group. A part of all of hexafluoroisopropyl hydroxyl groups may be protected by a protecting group. As the protecting group, there can be used any relatively stable protecting group common in the field of organic synthesis as is different from the acid labile group (unstable protecting group) that can readily be eliminated by the action of the acid generated from any of the above-mentioned photoacid generators of the general formulas (d) to (h).

The norbornene compounds or fluorine-containing norbornene compounds can be mononuclear or multinuclear. As the norbornene compounds, there can be used those formed by Diels-Alder addition reaction of an unsaturated compound such as a fluorine-containing olefin, allyl alcohol, fluorine-containing allyl alcohol, homoallyl alcohol, fluorine-containing homoallyl alcoholacrylic acid, α-fluoroacrylic acid, α-trifluoromethylacrylic acid, methacrylic acid, any of the acrylic esters, fluorine-containing acrylic esters, methacrylic esters and fluorine-containing methacrylic esters mentioned above in the present specification with cyclopentadiene or cyclohexadiene. More specifically, 3-(5-bicyclo[2.2.1]heptene-2-yl)-1,1,1-trifluoro-2-(trifluoromethyl)-2-propanol is an example of the norbornene compound.

Among the above-mentioned base resins, particularly preferred are those having a repeating unit of the general formula (6).

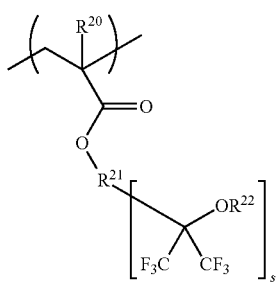

(6)

In the general formula (6), $R^{20}$ represents a hydrogen atom, a halogen atom or a $C_1$-$C_3$ alkyl or fluorine-containing alkyl group; $R^{21}$ represents a substituted or unsubstituted aliphatic hydrocarbon group, a substituted or unsubstituted divalent aromatic group or an organic group in which a plurality of substituted or unsubstituted aliphatic hydrocarbon and/or divalent aromatic groups are bonded to each other; any number of hydrogen atoms in $R^{21}$ may be substituted with a fluorine atom; $R^{22}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group; any number of hydrogen atoms in $R^{22}$ may be substituted with a fluorine atom; $R^{22}$ may contain an ether bond or a carbonyl group; and s represents an integer of 1 or 2.

$R^{20}$ in the general formula (6) is exemplified as follows. Examples of the halogen atom are fluorine, chlorine and bromine. Examples of the $C_1$-$C_3$ alkyl group are methyl, ethyl, propyl and isopropyl. Examples of the $C_1$-$C_3$ fluorine-containing alkyl group as $R^1$ are those obtained by substitution of a part or all of hydrogen atoms of the above alkyl groups with a fluorine atom, such as trifluoromethyl; —$CF_3$, trifluoroethyl; —$CH_2CF_3$, 1,1,1,3,3,3-hexafluoroisopropyl and heptafluoroisopropyl. Among others, preferred are a hydrogen atom, a fluorine atom, a methyl group and a trifluoromethyl group.

As mentioned above, $R^{21}$ in the general formula (6) is a substituted or unsubstituted aliphatic hydrocarbon group, a substituted or unsubstituted divalent aromatic group or an organic group in which a plurality of substituted or unsubstituted aliphatic hydrocarbon and/or divalent aromatic groups are bonded to each other; and any number of hydrogen atoms in $R^{21}$ may be substituted with a fluorine atom. The unsubstituted aliphatic hydrocarbon group can be straight, branched or cyclic. Examples of the unsubstituted divalent aliphatic hydrocarbon group are: straight or branched alkylene groups such as methylene, ethylene, isopropylene and t-butylene; and cyclic alkylene groups such as cyclobutylene, cyclohexylene, divalent norbornane and divalent adamantane. Examples of the unsubstituted aromatic group are divalent aromatic groups such as phenylene and naphthylene. There can also be used trivalenet groups obtained by elimination of one hydrogen atom from these divalent groups. Examples of the substituted aliphatic hydrocarbon and aromatic groups are those obtained by substitution of any number of hydrogen atoms in the above unsubstituted aliphatic hydrocarbon and aromatic groups with any kind of substituent.

Examples of the substituted or unsubstituted $C_1$-$C_{25}$ aliphatic hydrocarbon group or substituted or unsubstituted $C_1$-$C_{25}$ aromatic hydrocarbon group as $R^{22}$ are methyl, ethyl, propyl, isopropyl, cyclopropyl, n-propyl, sec-butyl, tert-butyl, n-pentyl, cyclopentyl, sec-pentyl, neopentyl, hexyl, cyclohexyl, ethylhexyl, norbornel, adamantyl, vinyl, allyl, butenyl, pentenyl, ethynyl, phenyl, benzyl and 4-methoxybenzyl. A part or all of hydrogen atoms of the above groups may be substituted with fluorine. There can also be used those having an oxygen atom, such as alkoxycarbonyl, acetal and acyl, as $R^{22}$. Examples of the alkoxycarbonyl group are tert-butoxycarbonyl, tert-amyloxycarbonyl, methoxycarbonyl, ethoxycarbonyl and i-propoxycarbonyl. Examples of the acetal group are: open-chain ethers such as methoxymethyl, methoxyethoxymethyl, ethoxyethyl, butoxyethyl, cyclohexyloxyethyl, benzyloxyethyl, phenethyloxyethyl, ethoxypropyl, benzyloxypropyl, phenethyloxypropyl, ethoxybutyl and ethoxyisobutyl; and cyclic ethers such as tetrahydrofuranyl and tetrahydropyranyl. Examples, of the acyl group are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydratropoyl, atropoyl, cinnamoyl, furoyl, thenoyl, nicotinoyl and isonicotinoyl. A part or all of hydrogen atoms of the above groups may be substituted with fluorine.

Particularly preferred examples of the repeating unit of the general formula (6) are those of the general formulas (7) to (9).

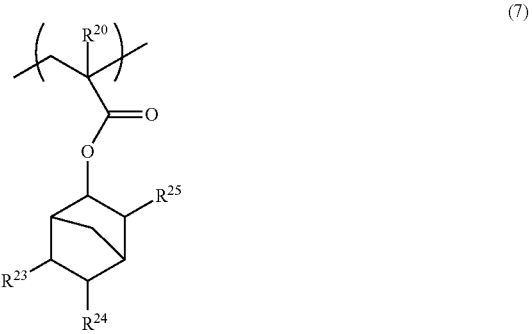

(7)

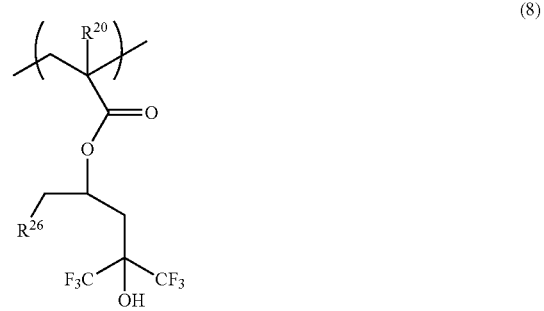

(8)

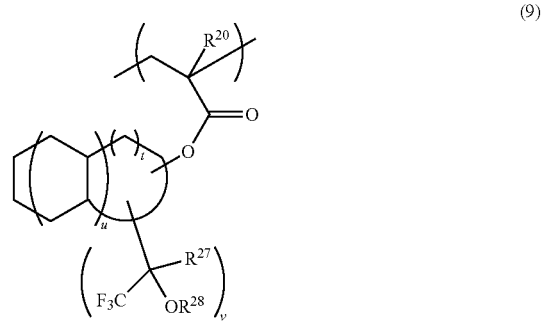

(9)

In the general formula (7), $R^{20}$ has the same meaning as in the general formula (6); one of $R^{23}$, $R^{24}$ and $R^{25}$ represents a $CF_3C(CF_3)(OH)CH_2$— group; and the other two of $R^{23}$, $R^{24}$ and $R^{25}$ each represent a hydrogen atom.

In the general formula (8), $R^{20}$ has the same meaning as in the general formula (6); and $R^{26}$ represents a hydrogen atom or a $C_1$-$C_4$ alkyl or fluorine-containing alkyl group. Examples of the $C_1$-$C_4$ alkyl or fluorine-containing alkyl group as $R^{26}$ are methyl, ethyl, n-propyl, isopropyl, n-butyl, sec-butyl, tert-butyl, fluoromethyl, difluoromethyl, trifluoromethyl and perfluoroethyl.

In the general formula (9), $R^{20}$ has the same meaning as in the general formula (6); $R^{27}$ represents a methyl group or a trifluoromethyl group; $R^{28}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an oxygen atom (ether bond) or a carbonyl group; u represents an integer of 0 to 2; and t and v each independently represent an integer of 1 to 8 and satisfy a relationship of $v \leq t+2$. In the case where there exist a plurality of $R^{27}$ or $R^{28}$, $R^{27}$ or $R^{28}$ can be the same or different. Further, $R^{28}$ in the general formula (9) has the same meaning as $R^{22}$ in the general formula (6).

As the base resin, there can suitably be used those having a repeating unit of the general formula (10) in addition to those having the repeating unit of the general formula (6).

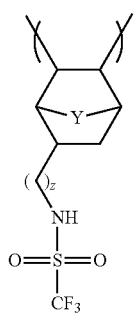

(10)

In the general formula (10), Y represents either —$CH_2$—, —O— or —S—; and z represents an integer of 2 to 6.

There can also suitably be used, as the base resin, those having a repeating unit of the general formula (11) in addition to those having the repeating units of the general formulas (6) to (10).

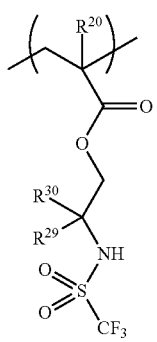

(11)

In the general formula (11), $R^{20}$ has the same meaning as in the general formula (6); $R^{29}$ and $R^{30}$ each independently represents a hydrogen atom, a substituted or unsubstituted $C_1$-$C_{25}$ straight, branched or cyclic aliphatic hydrocarbon group or a substituted or unsubstituted $C_1$-$C_{25}$ aromatic hydrocarbon group. Any number of hydrogen atoms in $R^{29}$, $R^{30}$ may be substituted with a fluorine atom. $R^{29}$ and $R^{30}$ may contain an ether bond or a carbonyl group. Examples of $R^{29}$, $R^{30}$ are the same as those of $R^{22}$ in the general formula (6). Among others, preferred are methyl and ethyl.

[Polymerization Process]

There is no particular limitation on the polymerization process for production of the base resin. It is preferable to adopt radical polymerization process or ionic polymerization process. In some cases, it is feasible to adopt coordination anionic polymerization process, living anionic polymerization process, cationic polymerization process, ring-opening metathesis polymerization process, vinylene polymerization process or vinyl addition process.

The radical polymerization process can be conducted by a known polymerization technique such as bulk polymerization, solution polymerization, suspension polymerization or emulsion polymerization technique in a batch, semi-continuous or continuous system in the presence of a radical polymerization initiator or a radical initiating source.

There is no particular limitation on the radical polymerization initiator. As the radical polymerization initiator, there can be used azo compounds, peroxide compounds and redox compounds. Preferred examples of the radical polymerization initiator are azobisbutyronitrile, tert-butylperoxypivalate, di-tert-butyl peroxide, i-butyryl peroxide, lauroyl peroxide, succinic peroxide, dicinnamyl peroxide, di-n-propylperoxydicarbonate, tert-butylperoxyallyl monocarbonate, benzoyl peroxide, hydrogen peroxide and ammonium persulfate.

There is also no particular limitation on the reaction vessel used in the polymerization reaction. Further, the polymerization reaction can be performed with the use of a polymerization solvent. As the polymerization solvent, preferred are those that do not interfere with the radical polymerization process. Typical examples of the polymerization solvent are: ester solvents such as ethyl acetate and n-butyl acetate; ketone solvents such as acetone and methyl isobutyl ketone; hydrocarbon solvents such as toluene and cyclohexane; and alcohol solvents such as methanol, isopropyl alcohol and ethylene glycol monomethyl ether. Water, ether solvents, cyclic ether solvents, fluorocarbon solvents and aromatic solvents are also usable. These solvents can be used solely or in combination of two or more thereof. A molecular weight adjusting agent such as mercaptan may be used in combination. The reaction temperature of the copolymerization reaction is set as appropriate depending on the kind of the radical polymerization initiator or radical initiating source and is generally preferably in the range of 20 to 200° C., more preferably 30 to 140° C.

As a technique for removing water or the organic solvent from the obtained fluorine-containing polymer solution or dispersion, it is feasible to adopt reprecipitation, filtration, distillation by heating under a reduced pressure or the like.

In the resist composition, any known photoacid generator can be used in combination with the photoacid generator according to the present invention. It is feasible to select and use any one of acid generators for chemically amplified resist compositions. Examples of the acid generator are bissulfonyldiazomethanes, nitrobenzyl derivatives, onium salts, halogen-containing triazine compounds, cyano-containing oximesulfonate compounds and other oximesulfonate compounds. These photoacid generators can be used solely or in combination of two or more thereof. The total amount of the photoacid generators used, including the photoacid generator according to the present invention, is generally in the range of 0.5 to 20 parts by mass per 100 parts by mass of the resist composition. If the total amount of the photoacid generators is less than 0.5 parts by mass, the resin composition unfavorably results in insufficient pattern formation. If the total amount of the photoacid generators exceeds 20 parts by mass, it is difficult to prepare the resin composition into a uniform solution. Further, the resin composition unfavorably tends to become low in storage stability if the total amount of the photoacid generators exceeds 20 parts by mass. The photoacid generator according to the present invention is generally contained by 1 to 100 parts by mass, preferably 10 to 100 parts by mass, more preferably 30 to 100 parts by mass, in 100 parts by mass of the total photoacid generator content.

[Solvent]

In the resist composition, an organic solvent is used as the solvent. There is no particular limitation on the organic solvent as long as the fluorine-containing polymer compound is soluble in the organic solvent. Examples of the organic solvent are: ketones such as acetone, methyl ethyl ketone, cyclohexanone, methyl isoamyl ketone and 2-heptanone; polyhydric alcohols and derivatives thereof, such as monomethyl ether, monoethyl ether, monopropyl ether, monobutyl ether or monophenyl ether of ethylene glycol, ethylene glycol monoacetate, diethylene glycol, diethylene glycol monoacetate, propylene glycol, propylene glycol monoacetate, propylene glycol monomethyl ether, propylene glycol monomethyl etheracetate (PGMEA), dipropylene glycol or dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improvement in ease of application. These solvents can be used solely or in combination of two or more thereof. The amount of the solvent is controlled in such a manner that the content of the solid matter such as base resin is 0.1 to 10 mass %. More specifically, the concentration of the resist composition is controlled in such a manner that the resulting resist film is 10 to 500 μm in thickness depending on the coating conditions and is in general of the order of 1 to 5 wt %.

[Basic Compound]

In the present invention, the basic compound is preferably contained as an optional component in the resist composition so as to serve as a quencher or to obtain improvements in resist pattern shape and post exposure stability.

There can be used any known basic compounds such as primary, secondary and tertiary aliphatic amines, aromatic amines, heterocyclic amines, nitrogen-containing compounds with hydroxyphenyl group, alcoholic nitrogen-containing compounds and amide derivatives. Among others, secondary and tertiary aliphatic amines, aromatic amines and heterocyclic amines are preferred.

The aliphatic amine can be an alkylamine or alkylalcoholamine obtained by replacing at least one hydrogen atom of ammonia ($NH_3$) with an alkyl or hydroxyalkyl group of up to 12 carbon atoms. Specific examples of the aliphatic amine are: monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine; and alkylalcoholamines such as diethanolamine, triethanolamine, diisopropanolamine, triisopropanolamine, di-n-octanolamine and tri-n-octanolamine. Above all, alkylacoholamines and trialkylamines are preferred. More preferred are alkylalcoholamines. Among the alkylalcoholamines, triethanolamine and triisopropanolamine are particularly preferred.

Other examples of the basic compound are: aromatic or heterocyclic amines such as aniline, aniline derivatives e.g. N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoluidine, heterocyclic amines e.g. 1,5-diazabicyclo[4.3.0]non-5-ene, 1,8-diazabicyclo[5.4.0]undec-7-ene, 1,4-diazabicyclo[2.2.2]octane, 4-dimethylaminopyridine, hexamethylenetetramine and 4,4-dimethylimidazoline, and hindered amines e.g. bis(1,2,2,6,6-pentamethyl-4-piperidyl)sebacate; and alcoholic nitrogen-containing compounds such as 2-hydroxypyridine, aminocresol, 2,4-quinolinediole, 3-indole methanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, and 1-[2-(2-hydroxyethoxy)ethyl]piperazine.

The above basic compounds can be used solely or in combination of two or more thereof.

The amount of the basic compound used is generally 0.01 to 5 parts by mass per 100 parts by mass of the base resin.

Further, an organic carboxylic acid or a phosphorus oxo acid or derivative thereof may be added an optional component to the resist composition in order to prevent sensitivity deterioration caused by the addition of the basic compound and to obtain improvements in resist pattern shape and post exposure stability. The acid compound can be used solely or in combination with the basic compound.

Suitable examples of the organic carboxylic acid are malonic acid, citric acid, malic acid, succinic acid, benzoic acid and salicylic acid.

Suitable examples of the phosphorus oxo acid or its derivative are: phosphoric acids and ester derivatives thereof, such as phosphoric acid, di-n-butyl phosphate and diphenyl phosphate; phosphonic acids and ester derivatives thereof, such as phosphonic acid, dimethyl phosphonate, di-n-butyl phosphonate, phenylphosphonic acid, diphenyl phosphonate and dibenzyl phosphonate; and phosphinic acids or ester derivatives thereof, such as phosphinic acid and phenylphosphinic acid. Among others, phosphonic acid is particularly preferred.

[Cross-Linking Agent]

There can be used, in the negative resist composition, any known cross-linking agent for chemically amplified negative resist compositions.

More specifically, the cross-linking agent can be any compound formed by reacting an amino-containing compound, such as melamine, acetoguanamine, benzoguanamine, urea, ethylene urea, propylene urea or glycoluril, with formaldehyde or a mixture of formaldehyde and lower alcohol and thereby substituting a hydrogen atom of the amino group with a hydroxymethyl group or a lower alkoxymethyl group.

The cross-linking agents using melamine, urea, alkylene urea e.g. ethylene urea, propylene urea etc. and glycoluril are herein referred to as "melamine-based cross-linking agent", "urea-based cross-linking agent", "alkylene urea-based cross-linking agent" and "glycoluril-based cross-linking agent", respectively. The cross-linking agent is preferably at least one kind selected from the group consisting of melamine-based cross-linking agents, urea-based cross-linking agents, alkylene urea-based cross-linking agents and glycoluril-based cross-linking agents. Particularly preferred are glycoluril-based cross-linking agents.

Specific examples of the melamine-based cross-linking agent are hexamethoxymethylmelamine, hexaethoxymethylmelamine, hexapropoxymethylmelamine and hexabutoxymethylmelamine. Among others, hexamethoxymethylmelamine is preferred.

Specific examples of the urea-based cross-linking agent are bismethoxymethylurea, bisethoxymethylurea, bispropoxymethylurea and bisbutoxymethylurea. Among others, bismethoxymethylurea is preferred.

Specific examples of the alkylene urea-based cross-linking agents are: ethylene urea-based cross-linking agents such as mono- and/or di-hydroxymethylated ethylene urea, mono- and/or di-methoxymethylated ethylene urea, mono- and/or di-ethoxymethylated ethylene urea, mono- and/or di-propoxymethylated ethylene urea and mono- and/or di-butoxymethylated ethylene urea; propylene urea-based cross-linking agents such as mono- and/or di-hydroxymethylated propylene urea, mono- and/or di-methoxymethylated propylene urea, mono- and/or di-ethoxymethylated propylene urea, mono- and/or di-propoxymethylated propylene urea and mono- and/or di-butoxymethylated propylene urea; 1,3-di(methoxymethyl)-4,5-dihydroxy-2-imidazolidinone; and 1,3-di(methoxymethyl)-4,5-dimethoxy-2-imidazolidinone.

Specific examples of the glycoluril-based cross-linking agents are mono-, di-, tri- and/or tetra-hydroxymethylated glycoluril, mono-, di-, tri- and/or tetra-methoxymethylated glycoluril, mono-, di-, tri- and/or tetra-ethoxymethylated glycoluril, mono-, di-, tri- and/or tetra-propoxymethylated glycoluril and mono-, di-, tri- and/or tetra-butoxymethylated glycoluril.

One kind of cross-linking agent component, or two or more kinds of cross-linking agent components in combination, can be used. The total amount of the cross-linking agent used is preferably 3 to 30 parts by mass, more preferably 3 to 25 parts by mass, most preferably 5 to 20 parts by mass, per 100 parts by mass of the base resin in the negative resist composition. When the total amount of the cross-linking agent is larger than or equal to the above-specified lower limit value, the resist composition can form sufficient cross-linking for good resist pattern. The resist composition can show good storage stability and can be prevented from deteriorating in sensitivity with time when the total amount of the cross-linking agent is smaller than or equal to the above-specified upper limit value.

[Surfactant and Others]

The surfactant, preferably either one or two or more kinds of fluorine- and/or silicon-based surfactants (fluorine-based surfactant, silicon-based surfactants and surfactant containing both of fluorine and silicon atoms) can be contained in the resist composition.

The addition of such a surfactant into the resist composition is effective for use with an exposure light source of 250 nm or less wavelength, notably 220 nm or less wavelength, and for pattern formation with a narrower pattern line width. The resist composition can attain good sensitivity and resolution and form a good resist pattern with less adhesion/development failures.

The additive resin is not particularly limited as long as the additive resin can be dissolved in the solvent used and has compatibility with the other components of the resist composition. The additive resin functions as a plasticizer, a stabilizer, a viscosity improver, a leveling agent, an antifoaming agent, a compatibilizer, a primer etc.

[Pattern Formation Method]

In the present invention, the resist composition can be used for resist pattern formation by a conventional photoresist technique. For example, the resist composition is first prepared in solution form, applied to a substrate such as a silicon wafer by e.g. a spinner and dried to form a photosensitive film. The thus-formed photosensitive film is irradiated with high-energy radiation or electron beam by e.g. an exposure device through a desired mask pattern, and then, subjected to heating. Subsequently, the exposed photosensitive film is developed with an alkaline developer such as 0.1 to 10 mass % tetramethylammoniumhydroxide solution. It is possible by the above method to form a resist pattern according to the mask pattern. As mentioned above, various additives compatible with the resist composition, such as additive resin, quencher, plasticizer, stabilizer, coloring agent, surfactant, viscosity improver, leveling agent, antifoaming agent, compatibilizer, primer, antioxidant etc., can be contained as desired.

There is no particular limitation on the high-energy radiation used in the present invention. It is particularly effective to use high-energy radiation of 300 nm or less wavelength, such as near-ultraviolet radiation (wavelength: 380 to 200 nm) or vacuum-ultraviolet radiation (far-ultraviolet radiation, VUV, wavelength: 200 to 10 nm) e.g. $F_2$ excimer laser, KrF excimer laser or ArF excimer laser, extreme-ultraviolet radiation (EUV, wavelength: 10 nm or shorter) e.g. synchrotron radiation, soft X-ray, X-ray, γ-ray, or electron beam. The names of the above electromagnetic waves are only for the sake of convenience. The light source is selected according to the wavelength because the physical and chemical properties of the electromagnetic wave depend on the wavelength of the electromagnetic wave. It is thus effective in the present pattern formation method to use an exposure device having a light source capable of generating such high-energy radiation of 300 nm or less wavelength of electron beam. The vacuum-ultraviolet radiation of 10 to 14 nm wavelength (sometimes called EUV or soft X-ray in the field of lithography) is preferably used. Further, it is effective to adopt a liquid immersion exposure device which uses a medium causing less absorption of high-energy radiation, such as water or fluorinated solvent, in a part of optical path and enables more efficient fine processing in terms of numerical aperture and effective wavelength. The resist composition is suitable for use in even such an exposure device.

In liquid immersion lithography using the liquid immersion exposure device, it is feasible to perform an exposure step by applying ArF excimer laser of 193 nm wavelength and inserting water or any liquid medium other than water, having a higher refractive index than air, between the substrate to which the resist composition has been applied and projection lens.

EXAMPLES

Hereinafter, the present invention will be described in more detail below by way of the following synthesis examples, working examples and comparative examples. It should be noted that the following working examples are illustrative and are not intended to limit the present invention thereto.

Synthesis Example 1

Triphenylsulfonium 2-[1-Ethoxycarbonyl-1-(1-adamantane)carbonyloxy-2,2,2-trifluoroethoxy]-1,1-difluoroethanesulfonate

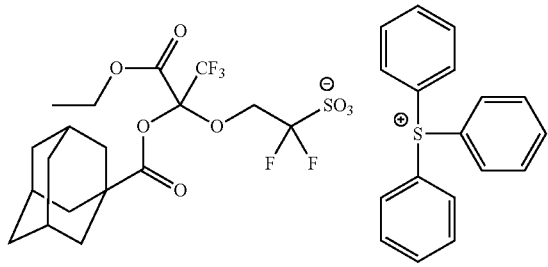

(PAG-1)

First, 5.0 g of triphenylsulfonium 2-hydroxy-1,1-difluoroethanesulfonate in white solid form (purity: 62.2%; equivalent to 7.3 mmol) was dissolved by stirring into 35 g of chloroform. The resulting solution was admixed with 1.46 g (equivalent to 8.55 mmol) of ethyltrifluoromethyl pyruvate and subjected to reaction for 3 hours at room temperature. This reaction solution was concentrated under a reduced pressure, followed by adding thereto 26.5 g of acetonitrile to dissolve the reaction intermediate by stirring. The dissolved solution was admixed with 1.56 g (equivalent to 9.56 mmol) of 1-adamantanecarboxylic acid chloride and 1.06 g (equivalent to 10.47 mmol) of triethylamine. The resulting mixture was stirred for 3 hours at room temperature and subjected to separation with the addition of 30 g of chloroform and 50 g of ion-exchanged water. The separated organic layer was washed once with 50 g of aqueous $NaHCO_3$ solution and further washed four times with 50 g of ion-exchanged water. After that, the organic layer was concentrated and then subjected to recrystallization with 50 g of ethyl acetate. By this, 1.3 g of the target compound was obtained in white solid form with a yield of 21%.

Properties of Triphenylsulfonium 2-[1-ethoxycarbonyl-1-(1-adamantane)carbonyloxy-2,2,2-trifluoroethoxy]-1,1-difluoroethanesulfonate $^1$H NMR (measurement solvent: deuterated chloroform, reference material: tetramethylsilane): δ=7.76-7.67 (m, 15H; $Ph_3S^+$), 4.61 (t, 2H, J=16.0 Hz), 4.26 (q, 2H, J=8.0 Hz), 2.00 (m, 3H, 1-Ad), 1.93 (m, 6H, 1-Ad), 1.69 (m, 6H, 1-Ad).

$^{19}$F NMR (measurement solvent: deuterated chloroform, reference material: trichlorofluoromethane): δ=−79.0 (s, 3F), −115.7 (m, 2F).

Synthesis Example 2

Triphenylsulfonium 4-[1-Ethoxycarbonyl-1-(1-adamantane)carbonyloxy-2,2,2-trifluoroethoxy]-1,1,2,2-tetrafluorobutanesulfonate

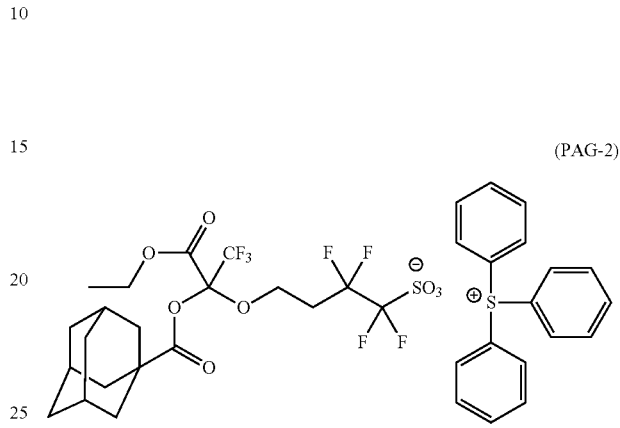

(PAG-2)

In a 1-L side-arm flask, 317.5 g of 33 mass % acetonitrile solution of triphenylsulfonium 4-hydroxy-1,1,2,2-tetrafluorobutanesulfonate (solute: 104.7 g, equivalent to 0.21 mol) was placed and admixed with 49.7 g (equivalent to 0.29 mol) of ethyltrifluoromethyl pyruvate. The resulting solution was subjected to reaction for 3 hours at room temperature. This reaction was sampled and analyzed by $^{19}$F NMR to confirm that the triphenylsulfonium 4-hydroxy-1,1,2,2-tetrafluorobutanesulfonate as the raw material was consumed. Subsequently, 46.1 g (equivalent to 0.28 mol) of 1-adamantanecarboxylic acid chloride and 0.47 g (equivalent to 0.0039 mol) of dimethylaminopyridine were added to the reaction solution and mixed by stirring. Further, a solution of 29.6 g (equivalent to 0.29 mol) of triethylamine in 100 g of acetonitrile was slowly added through a dropping funnel to the reaction solution over 1 hour. After the completion of the dropping, the resulting solution was stirred for 3 hours at room temperature and subjected to separation/washing with the addition of 200 g of chloroform and 200 g of 1% sodium hydrogencarbonate water. The separated organic layer was washed four times with 200 g of ion-exchanged water and concentrated. The thus-obtained viscous liquid was washed three times with 100 g of diisopropyl ether, dissolved in 200 g of acetone, and then, subjected to crystallization at room temperature with the addition of 50 g of diisopropyl ether. The crystallization product was filtered out and dried under a reduced pressure. By this, the target compound (white solid) was obtained in an amount of 162.2 g (equivalent to 0.198 mol, yield: 92%).

Properties of Triphenylsulfonium 4-[1-ethoxycarbonyl-1-(1-adamantane)carbonyloxy-2,2,2-trifluoroethoxy]-1,1,2,2-tetrafluorobutanesulfonate $^1$H NMR (measurement solvent: deuterated chloroform, reference material: tetramethylsilane): δ=7.69-7.62 (m, 15H; $Ph_3S^+$), 4.16 (q, 2H, J=8.0 Hz), 4.00 (m, 2H), 2.57 (m, 2H), 1.93 (m, 3H, 1-Ad), 1.82 (m, 6H, 1-Ad), 1.61 (m, 6H, 1-Ad), 1.27 (t, 3H, J=8.0 Hz).

Synthesis Example 3

Triphenylsulfonium 6-[1-Ethoxycarbonyl-1-(1-adamantane)carbonyloxy-2,2,2-trifluoroethoxy]-1,1,2,2-tetrafluorohexanesulfonate (PAG-3)

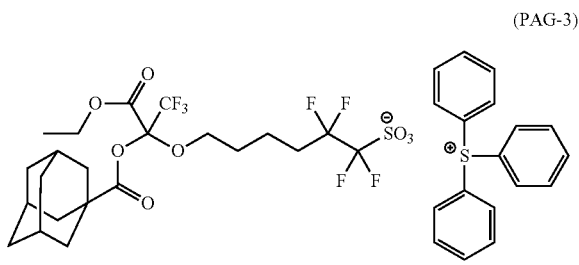

In a 500-mL side-arm flask, 146.4 g of 33 mass % acetonitrile solution of triphenylsulfonium 6-hydroxy-1,1,2,2-tetrafluorohexanesulfonate (solute: 48.3 g, equivalent to 56.9 mmol) was placed and admixed with 11.6 g (equivalent to 68.3 mmol) of ethyltrifluoromethyl pyruvate. The resulting solution was subjected to reaction for 3 hours at room temperature. This reaction was sampled and analyzed by $^{19}$F NMR to confirm that the triphenylsulfonium 6-hydroxy-1,1,2,2-tetrafluorohexanesulfonate as the raw material was consumed. Subsequently, 14.1 g (equivalent to 71.1 mmol) of 1-adamantanecarboxylic acid chloride and 0.14 g (equivalent to 1.14 mmol) of dimethylaminopyridine were added to the reaction solution and mixed by stirring. Further, a solution of 7.43 g (equivalent to 73.4 mmol) of triethylamine in 30 g of acetonitrile was slowly added through a dropping funnel to the reaction solution over 1 hour. After the completion of the dropping, the resulting solution was stirred for 3 hours at room temperature and subjected to separation/washing with the addition of 130 g of chloroform and 130 g of 1% sodium hydrogencarbonate water. The separated organic layer was washed four times with 130 g of ion-exchanged water and concentrated. The thus-obtained viscous liquid was washed three times with 100 g of diisopropyl ether, dissolved in 40 g of methyl ethyl ketone, and then, subjected to crystallization at room temperature with the addition of 250 g of diisopropyl ether. The crystallization product was filtered out and dried under a reduced pressure. By this, the target compound (white solid) was obtained in an amount of 40.5 g (purity: 99%, yield: 83%).

Properties of Triphenylsulfonium 6-[1-ethoxycarbonyl-1-(1-adamantane)carbonyloxy-2,2,2-trifluoroethoxy]-1,1,2,2-tetrafluorohexanesulfonate $^{1}$H NMR (measurement solvent: deuterated chloroform, reference material: tetramethylsilane): δ=7.69-7.62 (m, 15H; Ph$_3$S$^+$), 4.32 (q, 2H, J=8.0 Hz), 4.03 (m, 2H), 2.24 (m, 2H), 1.95 (m, 3H, 1-Ad), 1.78 (m, 6H, 1-Ad), 1.61 (m, 6H, 1-Ad), 1.57 (m, 2H), 1.43 (m, 2H), 1.25 (t, 3H, J=8.0 Hz).
$^{19}$F NMR (measurement solvent: deuterated chloroform, reference material: trichlorofluoromethane): δ=−79.6 (s, 3F), −112.4 (m, 2F), −118.0 (m, 2F).

$^{19}$F NMR (measurement solvent: deuterated chloroform, reference material: trichlorofluoromethane): δ=−79.2 (s, 3F), −112.8 (m, 2F), −118.7 (m, 2F).

Example 1

Measurements were made on the solubility of the fluorine-containing sulfonic acid onium salts according to the present invention, such as triphenylsulfonium 2-[1-ethoxycarbonyl-1-(1-adamantane)carbonyloxy-2,2,2-trifluoroethoxy]-1,1-difluoroethanesulfonate (PAG-1), triphenylsulfonium 4-[1-ethoxycarbonyl-1-(1-adamantane)carbonyloxy-2,2,2-trifluoroethoxy]-1,1,2,2-tetrafluorobutanesulfonate (PAG-2) and triphenylsulfonium 6-[1-ethoxycarbonyl-1-(1-adamantane)carbonyloxy-2,2,2-trifluoroethoxy]-1,1,2,2-tetrafluorohexanesulfonate (PAG-3), and conventional onium salts such as triphenylsulfonium (1-adamantyl)methoxycarbonyldifluoromethanesulfonate (PAG-C1) and triphenylsulfonium 2-(1-adamantane)carbonyloxy-1,1-difluoroethanesulfonate (PAG-C2) in various resist solvents.

The structures and abbreviations of the conventional onium salt photoacid generators used in this example are indicated below.

PAG-C1

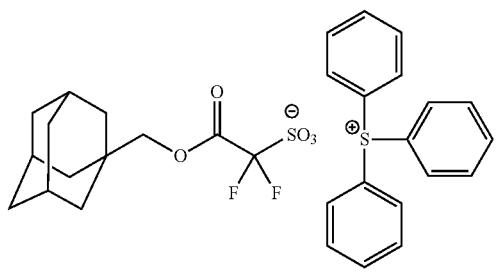

PAG-C2

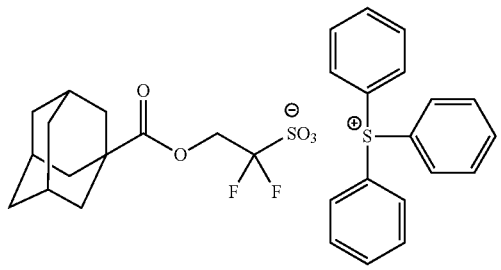

The solubility measurement results are indicated in TABLE 1.

TABLE 1

| Solvent | PAG-1 | PAG-2 | PAG-3 | PAG-C1 | PAG-C2 |
|---|---|---|---|---|---|
| PGMEA | 1 | 33 | 50 | 0.3 | 0.3 |
| Cyclohexanone | 33 | 50 | 65 | 3 | 3 |
| 2-Butanone | 33 | 50 | 75 | 3 | 3 |

It has been shown that each of the fluorine-containing sulfonic acid onium salts according to the present invention was much higher in solubility than the conventional onium salts.

[Production of Resins]

The structures and abbreviations of polymerizable monomers used in the following polymerization examples, working examples and comparative examples are indicated below. (The polymerizable monomers PAG-1, PAG-2, PAG-C1 and PAG-C2 were the same as mentioned above.)

(A-1)
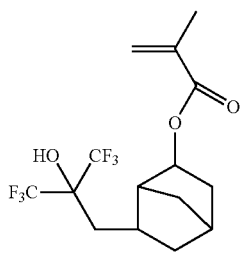
(A-2)
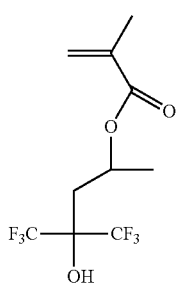
(A-3)
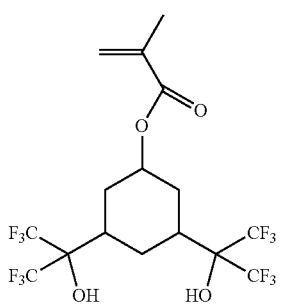
(A-4)
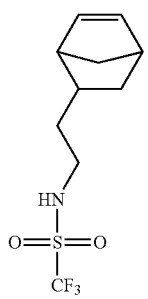
(A-5)
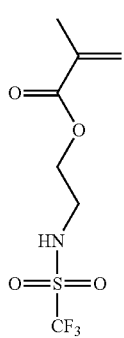
-continued
(A-6)
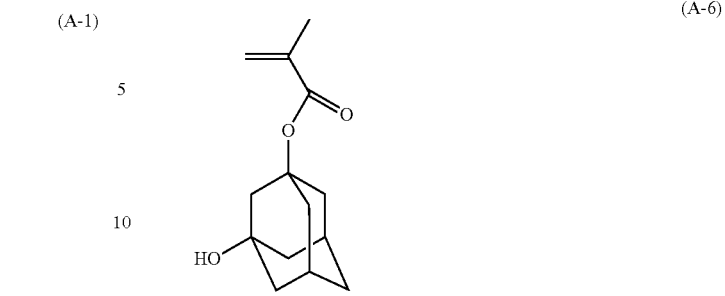
(B-1)
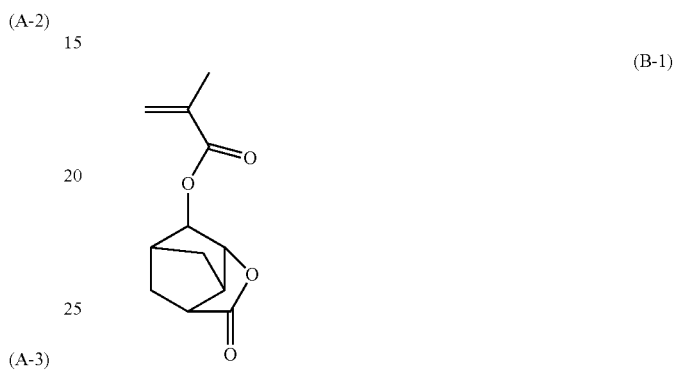
(B-2)
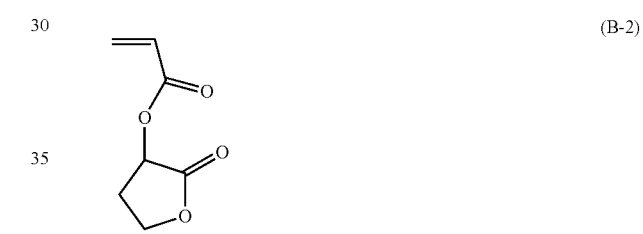
(C-1)
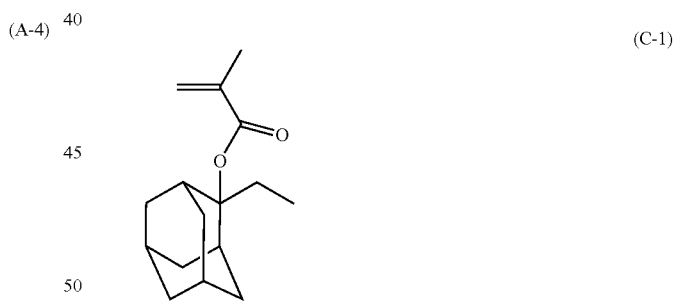
(C-2)
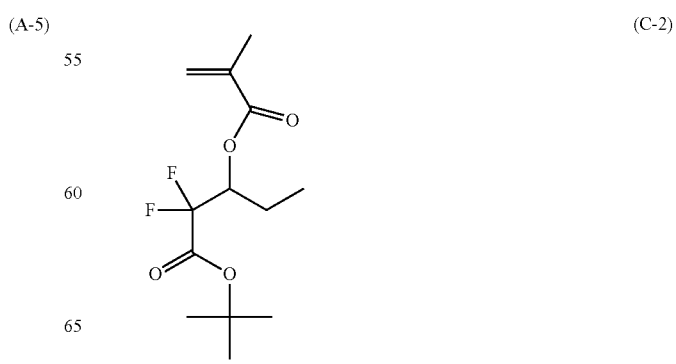

Polymerization Example P-1

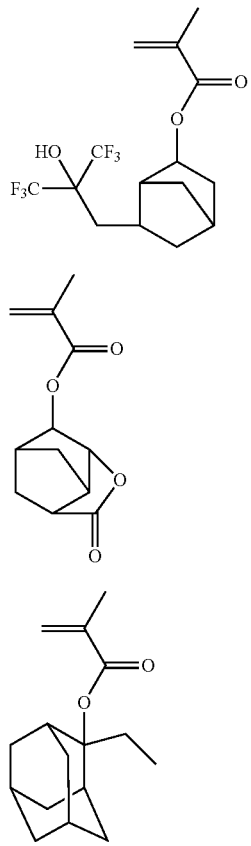

(A-1)

(B-1)

(C-1)

A monomer solution was prepared by dissolving 16.3 g (15 mol %) of compound (A-1), 30.2 g (45 mol %) of compound (B-1) and 30.0 g (40 mol %) of compound (C-1) in 300 g of 2-butanone and adding thereto 3.40 g of dimethyl 2,2'-azobis (2-methylpropionate). On the other hand, 100 g of 2-butanone was placed in a 1000-ml three-neck flask. The flask was then purged with nitrogen for 30 minutes and heated to 80° C. while stirring the content of the flask. The previously prepared monomer solution was dropped into the flask through a dropping funnel over 3 hours. Assuming the initiation of the dropping as a polymerization initiation time, the polymerization reaction was performed for 6 hours. After the completion of the polymerization reaction, the resulting polymerization solution was cooled by water to about 25° C. and put into 2 kg of methanol to precipitate a white powdery substance. The white powdery substance was filtered out of the solution.

The filtered white powdery substance was washed twice with 400 g of methanol in slurry form, filtered, and then, dried at 50° C. for 17 hours. By this, a polymer was obtained in white powder form (59.2 g). The mass-average molecular weight (Mw) of the polymer was 7,600. It was confirmed by $^{13}$C-NMR analysis that the polymer was in the form of a copolymer having repeating units derived from the compounds (A-1), (B-1) and (C-1) at a content ratio of 14.6:45.3: 40.1 (mol %). The thus-obtained copolymer was named as "Resin (P-1)".

Polymerization Examples P-2 to P-8

Resins (P-2 to P-8) were produced in the same manner as in Polymerization Example P-1. The kinds and contents of the copolymerization monomers, the mole ratio of the repeating units derived from the respective monomers and the mass-average molecular weight (Mw) of the produced resins are indicated in TABLE 2.

TABLE 2

| Polym- erization Example | Raw material composition | | | | | |
|---|---|---|---|---|---|---|
| | Monomer 1 | | Monomer 2 | | Monomer 3 | |
| Resin | Kind | mol % | Kind | mol % | Kind | mol % |
| P-1 | A-1 | 15 | B-1 | 45 | C-1 | 40 |
| P-2 | A-2 | 20 | B-1 | 45 | C-1 | 35 |
| P-3 | A-3 | 15 | B-1 | 45 | C-1 | 40 |
| P-4 | A-4 | 5 | B-1 | 45 | C-1 | 50 |
| P-5 | A-5 | 20 | B-1 | 45 | C-1 | 35 |
| P-6 | A-1 | 15 | B-1 | 45 | C-2 | 40 |
| P-7 | A-6 | 25 | B-1 | 35 | C-1 | 40 |
| P-8 | A-2 | 60 | B-2 | 15 | A-6 | 25 |

| Polym- erization Example | Mole ratio of repeating units in resin | | | Molecular weight |
|---|---|---|---|---|
| Resin | Monomer 1 | Monomer 2 | Monomer 3 | Mw |
| P-1 | 14 | 45 | 41 | 7,600 |
| P-2 | 19 | 46 | 35 | 8,800 |
| P-3 | 15 | 45 | 40 | 8,300 |
| P-4 | 5 | 46 | 49 | 8,000 |
| P-5 | 20 | 46 | 34 | 8,100 |
| P-6 | 15 | 46 | 39 | 7,500 |
| P-7 | 26 | 36 | 28 | 7,600 |
| P-8 | 61 | 16 | 23 | 9,100 |

Examples 2 to 33 and Comparative Examples 1 to 24

Resist compositions were each prepared by mixing the above-produced resin with a solvent, additives and the photoacid generator (PAG) according to the present invention, that is, 2-[1-ethoxycarbonyl-1-(1-adamantane)carbonyloxy-2,2,2-trifluoroethoxy]-1,1-difluoroethanesulfonate (PAG-1), triphenylsulfonium 4-[1-ethoxycarbonyl-1-(1-adamantane) carbonyloxy-2,2,2-trifluoroethoxy]-1,1,2,2-tetrafluorobutanesulfonate (PAG-2) or triphenylsulfonium 6-[1-ethoxycarbonyl-1-(1-adamantane)carbonyloxy-2,2,2-trifluoroethoxy]-1,1,2,2-tetrafluorohexanesulfonate (PAG-3) or the conventional photoacid generator (PAG), that is, triphenylsulfonium (1-adamantyl)methoxycarbonyldifluoromethanesulfonate (PAG-C1) or triphenylsulfonium 2-(1-adamantane)carbonyloxy-1,1-difluoroethanesulfonate (PAG-C2). The prepared resist compositions were tested for the solubility of the photoacid generator (PAG). The test results are indicated in TABLE 3.

The component ratios of the prepared resist compositions are indicated in TABLES 3 and 4. Further, resist solutions were prepared by filtering the resist compositions with 0.2-µm membrane filters, respectively. The resist solutions using the conventional photoacid generators PAG-C1 and PAG-C2, except those of Comparative Examples 2 and 8, were not used for resist film formation and patterning because the filter was clogged with insoluble matter during the filtration in each case.

The kinds of the solvent, the basic compound and the cross-linking agent used in each example are indicated below.
Solvent:
S-1: Propylene glycol monomethyl ether acetate (PGMEA)
S-2: Cyclohexanone
Basic compound:
O-1: N,N-Dibutylaniline
O-2: 2,6-Diisopropylaniline
O-3: Diazabicyclo[4.3.0]nonene Cross-Linking Agent:
NIKALAC MX-270 (glycoluril-based cross-linking agent, manufactured by Sanwa Chemical Co., Ltd.)

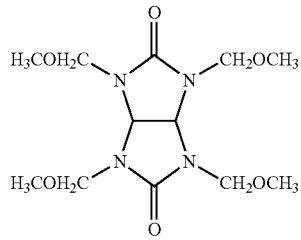

[Pattern Formation]

Each of the above-obtained resist solutions was spin-coated on a silicon wafer substrate to form a resist film of 250 nm thickness. The resist film was prebaked at 110° C., exposed to 248-nm ultraviolet radiation through a photomask, and then, subjected to post exposure baking treatment at 120° C. After that, the resist film was developed with 2.38 mass % aqueous tetramethylammoniumhydroxide solution for 1 minute at 23° C. It was possible to obtain a high-resolution pattern from each of the resist solution except that of Comparative Example 2. There were seen no failures such as poor substrate adhesion, poor film formation, development failure and poor etching resistance. The photoacid generator PAG-C1 was completely dissolved such that a clean rectangular pattern was formed from the resist solution only in the case of using the specific resin as in Comparative Example 8. The component ratio and evaluation results of the resist solutions are indicated in TABLES 3 and 4.

TABLE 3

| Example | Resin 1 Kind | Resin 1 parts by mass | PAG Kind | PAG parts by mass | Additive |
|---|---|---|---|---|---|
| 2  | P-1 | 40 | PAG-1 | 5  | O-2 |
| 3  | P-2 | 40 | PAG-1 | 5  | O-3 |
| 4  | P-3 | 40 | PAG-1 | 5  | O-3 |
| 5  | P-4 | 40 | PAG-1 | 5  | O-3 |
| 6  | P-5 | 40 | PAG-1 | 5  | O-1 |
| 7  | P-6 | 40 | PAG-1 | 5  | O-1 |
| 8  | P-7 | 40 | PAG-1 | 5  | O-1 |
| 9  | P-8 | 40 | PAG-1 | 5  | cross-linking agent O-1 |
| 10 | P-1 | 40 | PAG-1 | 20 | O-2 |
| 11 | P-2 | 40 | PAG-1 | 20 | O-3 |
| 12 | P-3 | 40 | PAG-1 | 20 | O-3 |
| 13 | P-4 | 40 | PAG-1 | 20 | O-3 |
| 14 | P-5 | 40 | PAG-1 | 20 | O-1 |
| 15 | P-6 | 40 | PAG-1 | 20 | O-1 |
| 16 | P-7 | 40 | PAG-1 | 20 | O-1 |
| 17 | P-8 | 40 | PAG-1 | 20 | cross-linking agent O-1 |
| 18 | P-1 | 40 | PAG-2 | 20 | O-2 |
| 19 | P-2 | 40 | PAG-2 | 20 | O-3 |
| 20 | P-3 | 40 | PAG-2 | 20 | O-3 |
| 21 | P-4 | 40 | PAG-2 | 20 | O-3 |
| 22 | P-5 | 40 | PAG-2 | 20 | O-1 |
| 23 | P-6 | 40 | PAG-2 | 20 | O-1 |
| 24 | P-7 | 40 | PAG-2 | 20 | O-1 |
| 25 | P-8 | 40 | PAG-2 | 20 | cross-linking agent O-1 |
| 26 | P-1 | 40 | PAG-3 | 20 | O-2 |
| 27 | P-2 | 40 | PAG-3 | 20 | O-3 |
| 28 | P-3 | 40 | PAG-3 | 20 | O-3 |
| 29 | P-4 | 40 | PAG-3 | 20 | O-3 |
| 30 | P-5 | 40 | PAG-3 | 20 | O-1 |
| 31 | P-6 | 40 | PAG-3 | 20 | O-1 |
| 32 | P-7 | 40 | PAG-3 | 20 | O-1 |
| 33 | P-8 | 40 | PAG-3 | 20 | cross-linking agent O-1 |

| Example | Solvent Kind | parts by mass | PAG solubility | Pattern shape |
|---|---|---|---|---|
| 2  | S-1 | 400 | completely dissolved | clean rectangular shape |
| 3  | S-1 | 400 | completely dissolved | clean rectangular shape |
| 4  | S-1 | 400 | completely dissolved | clean rectangular shape |
| 5  | S-1 | 400 | completely dissolved | clean rectangular shape |
| 6  | S-1 | 400 | completely dissolved | clean rectangular shape |
| 7  | S-1 | 400 | completely dissolved | clean rectangular shape |
| 8  | S-1 | 400 | completely dissolved | clean rectangular shape |
| 9  | S-1 | 400 | completely dissolved | clean rectangular shape |
| 10 | S-2 | 400 | completely dissolved | clean rectangular shape |
| 11 | S-2 | 400 | completely dissolved | clean rectangular shape |
| 12 | S-2 | 400 | completely dissolved | clean rectangular shape |
| 13 | S-2 | 400 | completely dissolved | clean rectangular shape |
| 14 | S-2 | 400 | completely dissolved | clean rectangular shape |

TABLE 3-continued

| | | | | |
|---|---|---|---|---|
| 15 | S-2 | 400 | completely dissolved | clean rectangular shape |
| 16 | S-2 | 400 | completely dissolved | clean rectangular shape |
| 17 | S-2 | 400 | completely dissolved | clean rectangular shape |
| 18 | S-1 | 400 | completely dissolved | clean rectangular shape |
| 19 | S-1 | 400 | completely dissolved | clean rectangular shape |
| 20 | S-1 | 400 | completely dissolved | clean rectangular shape |
| 21 | S-1 | 400 | completely dissolved | clean rectangular shape |
| 22 | S-1 | 400 | completely dissolved | clean rectangular shape |
| 23 | S-1 | 400 | completely dissolved | clean rectangular shape |
| 24 | S-1 | 400 | completely dissolved | clean rectangular shape |
| 25 | S-1 | 400 | completely dissolved | clean rectangular shape |
| 26 | S-1 | 400 | completely dissolved | clean rectangular shape |
| 27 | S-1 | 400 | completely dissolved | clean rectangular shape |
| 28 | S-1 | 400 | completely dissolved | clean rectangular shape |
| 29 | S-1 | 400 | completely dissolved | clean rectangular shape |
| 30 | S-1 | 400 | completely dissolved | clean rectangular shape |
| 31 | S-1 | 400 | completely dissolved | clean rectangular shape |
| 32 | S-1 | 400 | completely dissolved | clean rectangular shape |
| 33 | S-1 | 400 | completely dissolved | clean rectangular shape |

Basic compound: 0.4 parts by mass,
Cross-linking agent: 4 parts by mass
Solvent: S-1: Propylene glycol monomethyl ether acetate (PGMEA), S-2: Cyclohexanone
Basic compound: O-1: N,N-Dibutylaniline, O-2: 2,6-Diisopropylaniline, O-3: Diazabicyclo[4.3.0]nonene
Cross-linking agent: NIKALAC MX-270 (glycoluril-based cross-linking agent, manufactured by Sanwa Chemical Co., Ltd.)

TABLE 4

| Comparative Example | Resin 1 Kind | parts by mass | PAG Kind | parts by mass | Additive |
|---|---|---|---|---|---|
| 1 | P-1 | 40 | PAG-C1 | 5 | O-2 |
| 2 | P-2 | 40 | PAG-C1 | 5 | O-3 |
| 3 | P-3 | 40 | PAG-C1 | 5 | O-3 |
| 4 | P-4 | 40 | PAG-C1 | 5 | O-3 |
| 5 | P-5 | 40 | PAG-C1 | 5 | O-1 |
| 6 | P-6 | 40 | PAG-C1 | 5 | O-1 |
| 7 | P-7 | 40 | PAG-C1 | 5 | O-1 |
| 8 | P-8 | 40 | PAG-C1 | 5 | cross-linking agent O-1 |
| 9 | P-1 | 40 | PAG-C1 | 20 | O-2 |
| 10 | P-2 | 40 | PAG-C1 | 20 | O-3 |
| 11 | P-3 | 40 | PAG-C1 | 20 | O-3 |
| 12 | P-4 | 40 | PAG-C1 | 20 | O-3 |
| 13 | P-5 | 40 | PAG-C1 | 20 | O-1 |
| 14 | P-6 | 40 | PAG-C1 | 20 | O-1 |
| 15 | P-7 | 40 | PAG-C1 | 20 | O-1 |
| 16 | P-8 | 40 | PAG-C1 | 20 | cross linking agent O-1 |
| 17 | P-1 | 40 | PAG-C2 | 20 | O-2 |
| 18 | P-2 | 40 | PAG-C2 | 20 | O-3 |
| 19 | P-3 | 40 | PAG-C2 | 20 | O-3 |
| 20 | P-4 | 40 | PAG-C2 | 20 | O-3 |
| 21 | P-5 | 40 | PAG-C2 | 20 | O-1 |
| 22 | P-6 | 40 | PAG-C2 | 20 | O-1 |
| 23 | P-7 | 40 | PAG-C2 | 20 | O-1 |
| 24 | P-8 | 40 | PAG-C2 | 20 | cross linking agent O-1 |

| Example | Solvent Kind | parts by mass | PAG solubility | Pattern shape |
|---|---|---|---|---|
| 1 | S-1 | 400 | high insoluble content | — |
| 2 | S-1 | 400 | some insoluble content | slightly distorted shape |
| 3 | S-1 | 400 | high insoluble content | — |
| 4 | S-1 | 400 | high insoluble content | — |
| 5 | S-1 | 400 | high insoluble content | — |
| 6 | S-1 | 400 | high insoluble content | — |
| 7 | S-1 | 400 | high insoluble content | — |
| 8 | S-1 | 400 | completely dissolved | clean rectangular shape |
| 9 | S-2 | 400 | high insoluble content | — |
| 10 | S-2 | 400 | high insoluble content | — |
| 11 | S-2 | 400 | high insoluble content | — |
| 12 | S-2 | 400 | high insoluble content | — |
| 13 | S-2 | 400 | high insoluble content | — |
| 14 | S-2 | 400 | high insoluble content | — |
| 15 | S-2 | 400 | high insoluble content | — |
| 16 | S-2 | 400 | high insoluble content | — |
| 17 | S-1 | 400 | high insoluble content | — |
| 18 | S-1 | 400 | high insoluble content | — |
| 19 | S-1 | 400 | high insoluble content | — |
| 20 | S-1 | 400 | high insoluble content | — |
| 21 | S-1 | 400 | high insoluble content | — |
| 22 | S-1 | 400 | high insoluble content | — |
| 23 | S-1 | 400 | high insoluble content | — |
| 24 | S-1 | 400 | high insoluble content | — |

Basic compound: 0.4 parts by mass,
Cross-linking agent: 4 parts by mass
Solvent: S-1: Propylene glycol monomethyl ether acetate (PGMEA), S-2: Cyclohexanone
Basic compound: O-1: N,N-Dibutylaniline, O-2: 2,6-Diisopropylaniline, O-3: Diazabicyclo[4.3.0]nonene
Cross-linking agent: NIKALAC MX-270 (glycoluril-based cross-linking agent, manufactured by Sanwa Chemical Co., Ltd.)
—: The resist solution was not obtained due to clogging of the membrane filter caused by high insoluble content.

INDUSTRIAL APPLICABILITY

The resist composition according to the present invention can suitably be used in lithographic processes for semiconductor manufacturing.

The invention claimed is:

1. A resist composition comprising at least a base resin, a photoacid generator and a solvent, wherein the photoacid generator comprises a fluorine-containing sulfonic acid salt of the following general formula (4):

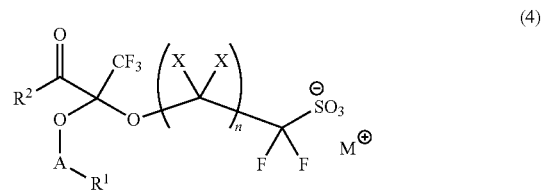

(4)

where X each independently represents a hydrogen atom or a fluorine atom; n represents an integer of 1 to 10; $R^1$ represents a hydrogen atom, a $C_1$-$C_{20}$ alkyl group, a $C_2$-$C_{20}$ alkenyl group or oxoalkyl group, or a $C_6$-$C_{18}$ aryl group or aralkyl group; any of hydrogen atoms on carbons in $R^1$ may be substituted with a substituent; $R^2$ represents either $R^A O$ or $R^B R^C N$; $R^A$, $R^B$ and $R^C$ each independently represents a hydrogen atom, a $C_1$-$C_{20}$ alkyl group, a $C_2$-$C_{20}$ alkenyl group, a $C_1$-$C_{20}$ oxoalkyl group, a $C_6$-$C_{18}$ aryl group, a $C_6$-$C_{18}$ aralkyl group, or a $C_3$-$C_{30}$ lactone group; $R^B$ and $R^C$ may be bonded to each other to form a 3- to 18-membered heterocyclic ring with a nitrogen atom (N) in $R^B R^C N$; any of hydrogen atoms on carbons in $R^A$, $R^B$ and $R^C$ may be substituted with a substituent; A represents any one of groups of the following formulas:

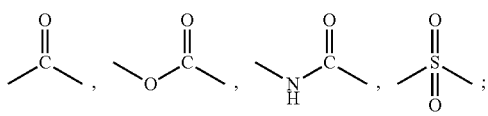

and $M^+$ represents a monovalent cation.

2. The resist composition according to claim 1, wherein the photoacid generator comprises a fluorine-containing sulfonic acid onium salt of the following general formula (2):

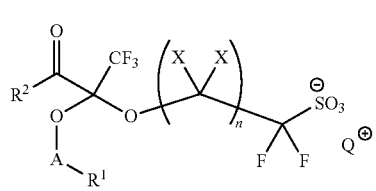

(2)

where X, n, A, $R^1$ and $R^2$ have the same meanings as in the general formula (4); and $Q^+$ represents a sulfonium cation of the following general formula (a) or an iodonium cation of the following general formula (b):

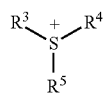

(a)

where $R^3$, $R^4$ and $R^5$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^3$, $R^4$ and $R^5$ may be bonded together to form a ring with a sulfur atom in the formula,

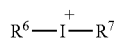

(b)

where $R^6$ and $R^7$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^6$ and $R^7$ may be bonded together to form a ring with an iodine atom in the formula.

3. The resist composition according to claim 2, wherein, in the general formula (2), —$(CX_2)_n$— is a repeating unit represented by —$(CH_2)_p$—$(CF_2)_q$— where p is an integer of 0 to 10; and q is an integer of 0 to 8.

4. The resist composition according to claim 3, wherein, in the general formula (2), —$(CX_2)_n$— is a repeating unit represented by —$(CH_2)_p$—$(CF_2)_q$— where p is an integer of 0 to 4; and q is 0 or 1.

5. The resist composition according to claim 2, wherein the base resin is a homopolymer of one kind of monomer, or a copolymer of two or more kinds of monomers, selected from the group consisting of acrylic esters, fluorine-containing acrylic esters, methacrylic esters, fluorine-containing methacrylic esters, styrenic compounds, fluorine-containing styrenic compounds, vinyl ethers, fluorine-containing vinyl ethers, allyl ethers, fluorine-containing allyl ethers, acrylamides, methacrylamides, vinyl esters, allyl esters, olefins, fluorine-containing olefins, norbornene compounds and fluorine-containing norbornene compounds.

6. The resist composition according to claim 5, wherein the base resin is insoluble or difficult to dissolve in a developer before exposure to high-energy radiation and is made soluble in a developer by the action of the photoacid generator as a result of exposure to high-energy radiation.

7. The resist composition according to claim 5, wherein the base resin is soluble in a developer before exposure to high-energy radiation and is made insoluble or difficult to dissolve in a developer by the action of the photoacid generator as a result of exposure to high-energy radiation.

8. A pattern formation method comprising: applying the resist composition according to claim 1 to a substrate; after heat treating the applied resist composition, exposing the applied resist composition to high-energy radiation of 300 nm or less wavelength through a photomask; and after heat treating the exposed resist composition as needed, developing the exposed resist composition with a developer.

9. The pattern formation method according to claim 8, wherein the exposing is performed by liquid immersion lithography using ArF excimer laser radiation of 193 nm wavelength and allowing insertion of water or any other liquid of higher refractive index than that of the air between the substrate to which the resist composition has been applied and projector lens.

10. A fluorine-containing sulfonic acid salt of the following general formula (4):

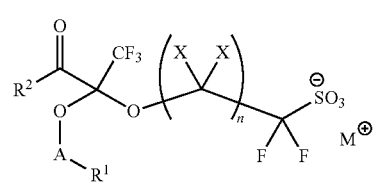

(4)

where X each independently represents a hydrogen atom or a fluorine atom; n represents an integer of 1 to 10; $R^1$ represents a hydrogen atom, a $C_1$-$C_{20}$ alkyl group, a $C_2$-$C_{20}$ alkenyl group or oxoalkyl group, or a $C_6$-$C_{18}$ aryl group or aralkyl group; any of hydrogen atoms on carbons in $R^1$ may be substituted with a substituent; $R^2$ represents either $R^A O$ or $R^B R^C N$; $R^A$, $R^B$ and $R^C$ each independently represents a hydrogen atom, a $C_1$-$C_{20}$ alkyl group, a $C_2$-$C_{20}$ alkenyl group, a $C_2$-$C_{20}$ oxoalkyl group, a $C_6$-$C_{18}$ aryl group, a $C_6$-$C_{18}$ aralkyl group, or a $C_3$-$C_{30}$ lactone group; $R^B$ and $R^C$ may be bonded to each other to form a 3- to 18-membered heterocyclic ring with a nitrogen atom (N) in $R^B R^C N$; any of hydrogen atoms on carbons in $R^A$, $R^B$ and $R^C$ may be substituted with a substituent; A represents any one of groups of the following formulas:

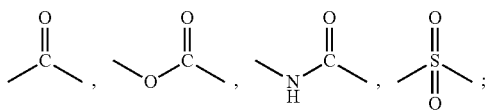

and M⁺ represents a monovalent cation.

11. The fluorine-containing sulfonic acid salt according to claim 10, wherein the fluorine-containing sulfonic acid salt is a fluorine-containing sulfonic acid onium salt of the following general formula (2):

(2)

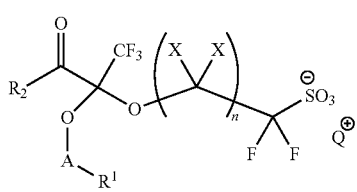

where X, n, A, $R^1$ and $R^2$ have the same meanings as in the general formula (4); and Q⁺ represents a sulfonium cation of the following general formula (a) or an iodonium cation of the following general formula (b):

(a)

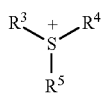

where $R^3$, $R^4$ and $R^5$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^3$, $R^4$ and $R^5$ may be bonded together to form a ring with a sulfur atom in the formula, (b)

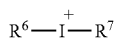

where $R^6$ and $R^7$ each independently represents a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^6$ and $R^7$ may be bonded together to form a ring with an iodine atom in the formula.

12. The fluorine-containing sulfonic acid salt according to claim 10, wherein, in the general formula (4), —$(CX_2)_n$— is a repeating unit represented by —$(CH_2)_p$—$(CF_2)_q$— where p is an integer of 0 to 10; and q is an integer of 0 to 8.

13. The fluorine-containing sulfonic acid salt according to claim 12, wherein, in the general formula (4), —$(CX_2)_n$— is a repeating unit represented by —$(CH_2)_p$—$(CF_2)_q$— where p is an integer of 0 to 4; and q is 0 or 1.

14. A photoacid generator comprising the fluorine-containing sulfonic acid salt according to claim 11.

\* \* \* \* \*